US011478480B2

(12) United States Patent
Bullock et al.

(10) Patent No.: US 11,478,480 B2
(45) Date of Patent: *Oct. 25, 2022

(54) FORMULATIONS OF 4-(7-HYDROXY-2-ISOPROPYL-4-OXO-4H-QUINAZOLIN-3-YL)-BENZONITRILE

(71) Applicant: NOVARTIS AG, Basel (CH)

(72) Inventors: Joseph Paul Bullock, Fort Worth, TX (US); Chinmay Maheshwari, Mason, OH (US); Quintus Medley, Wellesley, MA (US); Muneto Mogi, Waltham, MA (US); Michela Montecchi-Palmer, Fort Worth, TX (US); Kalliopi Stasi, Cambridge, MA (US)

(73) Assignee: Novartis AG, Basel (CH)

( * ) Notice: Subject to any disclaimer, the term of this patent is extended or adjusted under 35 U.S.C. 154(b) by 76 days.

This patent is subject to a terminal disclaimer.

(21) Appl. No.: 16/789,976

(22) Filed: Feb. 13, 2020

(65) Prior Publication Data

US 2020/0261457 A1    Aug. 20, 2020

Related U.S. Application Data

(60) Provisional application No. 62/806,705, filed on Feb. 15, 2019.

(51) Int. Cl.
| | | |
|---|---|---|
| *A61K 31/495* | (2006.01) | |
| *A61K 31/517* | (2006.01) | |
| *A61K 47/02* | (2006.01) | |
| *A61K 47/10* | (2017.01) | |
| *A61K 47/26* | (2006.01) | |
| *A61K 47/38* | (2006.01) | |
| *A61K 9/00* | (2006.01) | |

(52) U.S. Cl.
CPC ............ *A61K 31/517* (2013.01); *A61K 47/02* (2013.01); *A61K 47/10* (2013.01); *A61K 47/26* (2013.01); *A61K 47/38* (2013.01); *A61K 9/0048* (2013.01)

(58) Field of Classification Search
CPC .................................................. A61K 31/495
See application file for complete search history.

(56) References Cited

U.S. PATENT DOCUMENTS

| | | | | |
|---|---|---|---|---|
| 7,960,399 | B2 * | 6/2011 | Ritchie ................... | A61P 13/02 514/266.1 |
| 8,809,528 | B2 * | 8/2014 | Ritchie ................... | A61P 11/00 544/287 |
| 9,102,653 | B2 * | 8/2015 | Ritchie ................... | A61P 13/10 |
| 2015/0224131 | A1 | 8/2015 | Anton et al. | |
| 2015/0352176 | A1 * | 12/2015 | Takruri ................... | A61K 47/32 424/499 |
| 2020/0261456 | A1 * | 8/2020 | Medley ................... | A61K 45/06 |
| 2020/0390767 | A1 * | 12/2020 | Bullock ................... | A61K 9/10 |
| 2021/0275529 | A1 | 9/2021 | Medley et al. | |

FOREIGN PATENT DOCUMENTS

| | | | | |
|---|---|---|---|---|
| CN | 102875480 | A | 1/2013 | |
| EP | 2316420 | B1 | 2/2014 | |
| FR | 1367738 | A | 6/1963 | |
| FR | 1412615 | A | 10/1965 | |
| WO | 01/22936 | A1 | 4/2001 | |
| WO | 2005/120510 | A1 | 12/2005 | |
| WO | WO-2005120510 | A1 * | 12/2005 | ........... A61K 31/517 |
| WO | 2006/060618 | A2 | 6/2006 | |
| WO | 2007/056124 | A2 | 5/2007 | |
| WO | 2007/065662 | A2 | 6/2007 | |
| WO | 2007/065663 | A1 | 6/2007 | |
| WO | 2007/076087 | A2 | 7/2007 | |
| WO | 2007/090134 | A2 | 8/2007 | |
| WO | 2008/107390 | A1 | 9/2008 | |
| WO | 2008/140750 | A1 | 11/2008 | |
| WO | 2009/010529 | A1 | 1/2009 | |
| WO | 2009/081222 | A1 | 7/2009 | |
| WO | 2009/089057 | A1 | 7/2009 | |
| WO | 2009/090548 | A2 | 7/2009 | |
| WO | 2009/149239 | A1 | 12/2009 | |
| WO | 2010/023512 | A1 | 3/2010 | |
| WO | 2010/084050 | A2 | 7/2010 | |
| WO | 2011/120604 | A1 | 10/2011 | |
| WO | 2012/051036 | A1 | 4/2012 | |
| WO | 2014/152723 | A1 | 9/2014 | |
| WO | 2016/016908 | A1 | 2/2016 | |
| WO | 2016/123079 | A1 | 8/2016 | |
| WO | 2018/055524 | A1 | 3/2018 | |
| WO | 2018/055526 | A1 | 3/2018 | |
| WO | 2018/055527 | A1 | 3/2018 | |

OTHER PUBLICATIONS

Bhattacharya et al., "Studies on Transient Receptor Potential Vanilloid (TRPV) in human conjunctival epithelium," IOVS, (Jun. 2017) vol. 58(8):450; Meeting Info.: Annual Meeting of the Association-for-Research-in-Vision-and-Ophthalmology (ARVO). Baltimore, MD, USA. May 7-11, 2017, available at <https://iovs.arvojournals.org/article.aspx?articleid=2638626>, retrieved May 18, 2020 (4 pages).
Fier et al., "Reagent Design and Ligand Evolution for the Development of a Mild Copper-Catalyzed Hydroxylation Reaction," Org Lett. 19(11):3033-6 (2017).
Gonzalez et al., "SYL1001 Targeting TRPV1 Receptor for the Treatment of Ocular Pain associated to Dry Eye Syndrome," ARVO Annual Meeting Abstract Search and Program Planner, (May 2011) vol. 52(3844). Meeting Info.: Annual Meeting of the Association for Research in Vision and Ophthalmology (ARVO). Ft Lauderdale, FL, USA. May 1-5, 2011, available at <https://iovs.arvojournals.org/article.aspx?articleid=2355991>, retrieved May 18, 2020 (4 pages).

(Continued)

*Primary Examiner* — John S Kenyon
(74) *Attorney, Agent, or Firm* — Hong-Van Le

(57) ABSTRACT

The present invention provides formulations of 4-(7-hydroxy-2-isopropyl-4-oxo-4H-quinazolin-3-yl)-benzonitrile (compound I) and methods for treating ocular surface pain by administering such formulations. The present invention also provides methods for treating dry eye disease and ocular hyperemia by administering formulations of 4-(7-hydroxy-2-isopropyl-4-oxo-4H-quinazolin-3-yl)-benzonitrile.

11 Claims, 10 Drawing Sheets

(56) References Cited

OTHER PUBLICATIONS

Moreno-Montañés et al., "Tivanisiran, a Novel siRNA for the Treatment of Dry Eye Disease," Expert Opin Investig Drugs. 27(4):421-6 (2018).

Okada et al., "Systemic administration of TRPV4 antagonist suppresses corneal inflammation and scarring induced by alkali burning in mice," Investigative Ophthalmology and Visual Science, (Apr. 2014) 55(13):4683. Meeting Info: 2014 Annual Meeting of the Association for Research in Vision and Ophthalmology (ARVO). Orlando, FL, USA. May 4, 2014-May 8, 2014, available at <https://iovs.arvojournals.org/article.aspx?articleid=2270219>, retrieved May 18, 2020 (4 pages).

Novartis Institutes for BioMedical Research, "A randomized, vehicle-controlled, subject and investigator-masked, proof-of-concept study to evaluate the use of topical ocular SAF312 in the treatment of postoperative ocular pain in patients undergoing photorefractive keratectomy (PRK) surgery," Clinical Trial Protocol CSAF312X2201, published Apr. 11, 2019, available at <https://clinicaltrials.gov/ProvidedDocs/62/NCT02961062/Prot_000.pdf>, retrieved Apr. 21, 2020 (72 pages).

Biostatistics and Statistical Programming/Novartis Institutes for BioMedical Research, "A randomized, vehicle-controlled, subject and investigator-masked, proof-of-concept study to evaluate the use of topical ocular SAF312 in the treatment of postoperative ocular pain in patients undergoing photorefractive keratectomy (PRK) surgery," Statistical Analysis Plan, published Apr. 11, 2019, available at <https://clinicaltrials.gov/ProvidedDocs/62/NCT02961062/SAP_001.pdf>, retrieved Apr. 21, 2020 (14 pages).

Pubchem, "4-(7-Hydroxy-2-isopropyl-4-oxoquinazolin-3(4H)-YL)benzonitrile: C18H15N3O2-PubChem," available at <https://pubchem.ncbi.nlm.nih.gov/compounds/25138363#section=InChI>, retrieved on Apr. 21, 2020 (13 pages).

Florence, "Polymorph screening in pharmaceutical development—European Pharmaceutical Review," published on Aug. 19, 2010, available at <https://www.europeanpharmaceuticalreview.com/article/3659/polymorph-screening-in-pharmaceutical-development/>, retrieved Mar. 7, 2018 (13 pages).

Dermer et al., "A Review of Management Strategies for Nociceptive and Neuropathic Ocular Surface Pain," Drugs. 80 (6):547-71 (2020).

Sarhan et al., "Synthesis of Furoquinazoline Derivatiives of Expected Antibacterial Activity," Egypt J Pharm Sci. 33 (3-4):631-8 (1992).

International Search Report and Written Opinion for PCT/IB2020/051211, dated May 4, 2020 (17 pages).

History of Changes for Study: NCT02961062, Study of SAF312 as an Eye Drop for Treatment of Eye Pain Following Photorefractive Keratectomy (PRK) Surgery, submitted on Nov. 8, 2016, available at <https://clinicaltrials.gov/ct2/history/NCT02961062?A=1&B=1&C=merged>, retrieved on Jul. 23, 2020 (6 pages).

History of Changes for Study: NCT02961062, Study of SAF312 as an Eye Drop for Treatment of Eye Pain Following Photorefractive Keratectomy (PRK) Surgery, submitted on Jul. 23, 2017, available at <https://clinicaltrials.gov/ct2/history/NCT02961062?A=2&B=2&C=merged>, retrieved on Jul. 23, 2020 (6 pages).

History of Changes for Study: NCT02961062, Study of SAF312 as an Eye Drop for Treatment of Eye Pain Following Photorefractive Keratectomy (PRK) Surgery, submitted on Oct. 10, 2017, available at <https://clinicaltrials.gov/ct2/history/NCT02961062?A=3&B=3&C=merged>, retrieved on Jul. 23, 2020 (6 pages).

History of Changes for Study: NCT02961062, Study of SAF312 as an Eye Drop for Treatment of Eye Pain Following Photorefractive Keratectomy (PRK) Surgery, submitted on Oct. 19, 2017 available at <https://clinicaltrials.gov/ct2/history/NCT02961062?A=4&B=4&C=merged>, retrieved on Jul. 23, 2020 (6 pages).

History of Changes for Study: NCT02961062, Study of SAF312 as an Eye Drop for Treatment of Eye Pain Following Photorefractive Keratectomy (PRK) Surgery, submitted on Dec. 5, 2017, available at <https://clinicaltrials.gov/ct2/history/NCT02961062?A=5&B=5&C=merged>, retrieved on Jul. 23, 2020 (6 pages).

History of Changes for Study: NCT02961062, Study of SAF312 as an Eye Drop for Treatment of Eye Pain Following Photorefractive Keratectomy (PRK) Surgery, submitted on Feb. 25, 2018, available at <https://clinicaltrials.gov/ct2/history/NCT02961062?A=6&B=6&C=merged>, retrieved on Jul. 23, 2020 (6 pages).

History of Changes for Study: NCT02961062, Study of SAF312 as an Eye Drop for Treatment of Eye Pain Following Photorefractive Keratectomy (PRK) Surgery, submitted on Jun. 6, 2018, available at <https://clinicaltrials.gov/ct2/history/NCT02961062?A=7&B=7&C=merged>, retrieved on Jul. 23, 2020 (6 pages).

History of Changes for Study: NCT02961062, Study of SAF312 as an Eye Drop for Treatment of Eye Pain Following Photorefractive Keratectomy (PRK) Surgery, submitted on Mar. 21, 2019 available at <https://clinicaltrials.gov/ct2/history/NCT02961062?A=7&B=7&C=merged>, retrieved on Jul. 23, 2020 (14 pages).

Trial Record for Study: NCT02961062, Study of SAF312 as an Eye Drop for Treatment of Eye Pain Following Photorefractive Keratectomy (PRK) Surgery, available at <https://clinicaltrials.gov/ct2/show/NCT02961062?term=NCT02961062&draw=2&rank=1>, retrieved on Jul. 28, 2020 (6 pages).

Updated International Search Report and Written Opinion for PCT/IB2020/051211, dated Feb. 2, 2021 (19 pages).

PubChem Substance Record for saf312, available at <https://pubchem.ncbi.nlm.nih.gove/substance/341696399> available Sep. 13, 2017 (1 page).

* cited by examiner

Quadrants S: Superior; N: nasal; I: inferior; T: temporal

FORMULATIONS OF 4-(7-HYDROXY-2-ISOPROPYL-4-OXO-4H-QUINAZOLIN-3-YL)-BENZONITRILE

REFERENCE TO RELATED APPLICATIONS

The application claims priority to U.S. Provisional Application No. 62/806,705, which is incorporated herein in its entirety.

FIELD OF THE INVENTION

The present disclosure relates to formulations of 4-(7-Hydroxy-2-isopropyl-4-oxo-4H-quinazolin-3-yl)-benzonitrile (Formula I) and methods for treating ocular surface diseases using same as well as methods for reducing ocular surface pain.

BACKGROUND OF THE INVENTION

The ocular surface, particularly the cornea, is densely innervated by sensory nerves. The activity of corneal nerves can be modified by inflammation caused by a number of factors, such as osmotic stress and tissue damage, as well as nerve injuries of the ocular surface. Ocular surface symptoms are the alarm system to indicate an imbalanced ocular surface homeostasis resulting in chronic ocular surface pain due to continuous stimuli causing stress and sensitization of the ocular surface.

Patients suffering from ocular surface pain, particularly chronic ocular surface pain have a significant decline in quality of life. In utility studies to date, the burden of severe chronic ocular surface pain has been likened to moderate to severe angina, dialysis, or disabling hip fracture. Severe chronic ocular surface pain as also been associated with depression and suicidal ideation. In many patients, the ocular surface pain remains unresolved despite treatment of the underlying pathology (e.g., recent trauma or surgery, infection, or inflammation). Moreover, treatments that are used for short term management of ocular pain (e.g., non-steroidal anti-inflammatory drugs, steroids, antibiotics) cannot be used for long term therapy. Thus, there is a long-felt and unmet need for safe, effective formulations for the symptomatic treatment of ocular surface pain when there are no other options to improve patients' quality of life, or to supplement current treatments.

While topical administration of aqueous compositions is non-invasive and very convenient, it remains a challenge to formulate hydrophobic compounds into stable, aqueous formulations. Agglomeration can be particularly troublesome for the hydrophobic ophthalmic drugs, which are particularly prone to agglomeration within aqueous topical ophthalmic compositions. Agglomeration may cause stability and potentially other quality issues for the compositions, and may arise from other interactions of drugs and excipients.

In view of the above, it would be particularly desirable to provide an ophthalmic composition, which can be dosed topically for the treatment of ocular surface conditions, particular the treatment of ocular surface pain.

SUMMARY OF THE INVENTION

In some embodiments, described herein is an aqueous formulation that includes:

4-(7-Hydroxy-2-isopropyl-4-oxo-4H-quinazolin-3-yl)-benzonitrile (compound I) or a salt, co-crystal, or polymorph thereof, and one or more excipients selected from the group consisting of a surfactant, a suspending agent, a tonicity agent, a buffer, a salt, and a preservative.

In some embodiments, the 4-(7-Hydroxy-2-isopropyl-4-oxo-4H-quinazolin-3-yl)-benzonitrile (compound I) or a salt, co-crystal, or polymorph thereof is present in the formulation as a suspension. In alternative or additional embodiments, the 4-(7-Hydroxy-2-isopropyl-4-oxo-4H-quinazolin-3-yl)-benzonitrile (compound I) or a salt, co-crystal, or polymorph thereof is present in the formulation in an amount of about 0.5% w/v to about 3.5% w/v.

In some embodiments, described herein is an aqueous formulation that includes:

4-(7-Hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, present as a suspension in the formulation, a surfactant, a suspending agent, and one or more excipients selected from the group consisting of a tonicity agent, a buffer, a salt, and a preservative.

In some embodiments, the invention described herein is a formulation that includes:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, a non-ionic surfactant;

a suspending agent;

a tonicity agent;

a buffer;

a salt; and optionally, a preservative.

In some embodiments, the present disclosure relates to a formulation, comprising:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, a surfactant selected from the group consisting of non-ionic, anionic, cationic surfactants, and combinations thereof;

a suspending agent;

a tonicity agent;

a buffer;

optionally, a salt;

optionally, a preservative; and water in quantity sufficient (qs) to 100%.

In some embodiments, the formulation includes a non-ionic surfactant. In some embodiments of the formulations described herein, the non-ionic surfactant is selected from the group consisting of a polysorbate surfactant, a block copolymer of ethylene oxide, propylene oxide surfactant, poloxamer, tyloxapol, and combinations thereof.

In some embodiments of the formulations described herein, the non-ionic surfactant is tyloxapol, which present in an amount at least about 0.001% w/v, at least about 0.01% w/v, at least about 0.02% w/v, least about 0.03% w/v, or at least about 0.04% w/v, and no more than about 1% w/v, no more than about 0.5% w/v, no more than about 0.3% w/v, or no more than about 0.2% w/v, no more than about 0.1% w/v, or no more than about 0.08% w/v. In some embodiments, the tyloxapol is present in an amount of about 0.03% w/v to 0.08% w/v, or about 0.05% w/v.

In some embodiments of the formulations described herein, the non-ionic surfactant is poloxamer in an amount of about 15 to about 20% w/v of the formulation.

In some embodiments of the formulations described herein, the suspending agent is selected from the group consisting of carbomer, hydroxypropyl methyl cellulose (hypromellose), polyethylene glycol, and combinations thereof. In some embodiments, the suspending agent is carbomer, present in the formulation in an amount of at least about 0.05% w/v, at least about 0.1% w/v, or at least about 0.2% w/v, and no greater than about 1.0% w/v, no greater than about 0.6% w/v, or no greater than about 0.5%. In some embodiments, the carbomer is present in the formulation in an amount of 0.1% w/v to about 0.3% w/v, or about 0.2% w/v.

In some embodiments of the formulations described herein, the suspending agent is hydroxypropyl methyl cellulose present in the formulation in an amount of at least about 0.05% w/v, at least about 0.1% w/v, or at least about 0.25% w/v, and less than about 1.8% w/v, less than about 1.0% w/v, less than about 0.8% w/v, or less than about 0.6% w/v. In some embodiments, the suspending agent is a polyethylene glycol (PEG) having molecular weight of from about 200 to about 20,000 Da. In some embodiments, the suspending agent is PEG400, at a concentration of from about 4% w/v to about 9% w/v, about 5% w/v to about 8% w/v, or about 7% w/v, or PEG6000 at a concentration of from about 1% w/v to about 4% w/v, about 1% w/v to about 3% w/v, or about 2% w/v.

In some embodiments of the formulations described herein, the suspending agent is substantially all carbomer homopolymer Type B.

In some embodiments of the formulations described herein, the tonicity agent is selected from the group consisting of polyols.

In some embodiments of the formulations described herein, the polyol is selected from the group selected from mannitol, glycerin, xylitol, sorbitol and propylene glycol, and combinations thereof. In some embodiments, the polyol is present in an amount from about 0.05% w/v to about 10% w/v, from about 0.1% to about 8% w/v, from about 0.1% to about 7% w/v, from about 0.1% to about 5% w/v. In particular embodiments, the polyol is mannitol or glycerin, present in the formulation in an amount of from about 0.1% w/v to about 5% w/v, or about 0.2% w/v, about 0.3% w/v, about 0.4% w/v, about 0.5% w/v, about 1% w/v, about 2% w/v, about 2.5% w/v, about 3.0% w/v, about 3.5% w/v, about 4.0% w/v, about 4.5% w/v, or about 5% w/v.

In some embodiments of the formulations described herein, the buffer is selected from the group consisting of acetate, ascorbate, borate, hydrogen carbonate, carbonate, citrate, edetate (EDTA) gluconate, lactate, phosphate, propionate and TRIS (tromethamine). In particular embodiments, the buffer is phosphate or TRIS.

In some embodiments of the formulations described herein, the salt is sodium chloride or potassium chloride.

In some embodiments of the formulations described herein, the suspending agent is carbopol (carbomer homopolymer Type B) and amount of sodium chloride is adjusted to an amount to provide a viscosity of the formulation of about 20 cP to about 200 cP, when using spindle CP-42 at 60 rpm at about 25° C. In some embodiments, the sodium chloride is present in an amount from about 0.01% w/v to about 0.5% w/v, from about 0.02% w/v to about 0.4% w/v, from about 0.03% w/v to about 0.3% w/v, from about 0.04% w/v to about 0.2% w/v, from about 0.05% w/v to about 0.1% w/v, or about 0.05% w/v.

In some embodiments of the formulations described herein, the pH of the formulation is about 5.5 to about 8.0. In some embodiments, the pH of the formulation is from about 6.0 to about 8.0, about 6.0, or about 7.4. In some embodiments, the pH of the formulation is about 5.0 to about 8.0, about 5.5 to about 7.5, about 5.0 to about 7.4, about 5.5 to about 7.4, about 6.0 to about 8.0, about 6.5 to about 8.0, about 6.0 to about 7.4, or about 6.5 to about 7.4.

In some embodiments the formulations described herein further include an additional agent selected from the group consisting of cyclodextrins in an amount of at least about 1.5 w/v %, at least about 3.0 w/v %, at least about 3.5 w/v % or at least about 4.5 w/v %, but no greater than about 10.0 w/v %, no greater than about 8.0% w/v, no greater than about 6.5 w/v %, or no greater than about 5.5 w/v. In some embodiments, the cyclodextrin is hydroxypropyl β-cyclodextrin or sulfoalkylether β-cyclodextrin in an amount of about 5% w/v of the formulation.

In some embodiments, the present disclosure is related to a formulation, comprising:

the compound I or a salt, co-crystal, or polymorph thereof, is in an amount of about 0.5% w/v to about 2.5% w/v, the a non-ionic surfactant is tyloxapol, poloxamer, or combinations thereof, in an amount of from about 0.01 to 0.2% w/v;

the a suspending agent is hydroxypropyl methyl cellulose, polyethylene glycol or carbomer homopolymer Type B;

the a tonicity agent is at least one polyol in an amount of from about 0.05% w/v to about 10% w/v;

the buffer is edetate, phosphate, borate, or combinations thereof a salt; and water qs to 100%; and the pH is in the range of from about 5.5 to about 8.0.

In some embodiments, the present disclosure is related to a formulation, comprising:

compound I or a salt, co-crystal, or polymorph thereof, is present in an amount of about 0.5% w/v, about 1.0% w/v, about 1.5% w/v, about 2.0% w/v, or about 2.5% w/v, a non-ionic surfactant, which is tyloxapol in an amount of about 0.04 w/v to about 0.06% w/v, poloxamer in an amount of about 0.005-0.12% w/v, or combinations thereof;

a suspending agent, which is hydroxypropyl methyl cellulose in an amount of from about 0.1% w/v to about 0.8 w/v %, polyethylene glycol in an amount of from about 2% w/v to about 8% w/v, carbomer homopolymer Type B in an amount from about 0.05% w/v to about 0.5% w/v, or combinations thereof;

a tonicity agent which is mannitol or glycerin in an amount of from about 0.1% w/v to about 5% w/v;

a buffer which is edetate, phosphate, borate, tromethamine, or combinations thereof;

sodium chloride in an amount of from 0.01% w/v to about 1% w/v; and water qs to 100%; and having a pH is in the range of from about 5.5 to about 8.0.

In some embodiments, the present disclosure is related to a formulation, comprising:

a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v, about 1.0% w/v, about 1.5% w/v, about 2.0% w/v, or about 2.5% w/v, tyloxapol in an amount of about 0.04 w/v to about 0.06% w/v;

carbomer homopolymer Type B in an amount from about 0.05% w/v to about 0.4% w/v;

glycerin in an amount of from about 0.5% w/v to about 5% w/v;

a buffer selected from the group consisting of edetate, phosphate, borate, tomethamine, and combinations thereof;

sodium chloride in an amount of from 0.01% w/v to about 1% w/v; and water qs to 100%;

wherein the formulation has a pH in the range of from about 5.5 to about 8.0.

In some embodiments of the formulations described herein, compound I is in polymorphic form B.

In some embodiments, the present disclosure is related to a formulation, comprising:

a suspension of polymorphic form B of 4-(7-Hydroxy-2-isopropyl-4-oxo-4H-quinazolin-3-yl)-benzonitrile (compound I), in an amount of about 0.5% w/v, about 1.0% w/v, about 1.5% w/v, about 2.0% w/v, or about 2.5% w/v, tyloxapol in an amount of about 0.04 w/v to about 0.06% w/v;

carbomer homopolymer Type B in an amount from about 0.05% w/v to about 0.4% w/v;

glycerin in an amount of from about 0.5% w/v to about 5% w/v;

a buffer selected from edetate, phosphate, borate, tomethamine, or combinations thereof;

sodium chloride in an amount of from 0.01% w/v to about 1% w/v; and water qs to 100%;

wherein the formulation has a pH in the range of from about 5.5 to about 8.0.

In some embodiments, the formulation comprises:
compound I in an amount of about 0.5% w/v, about 1.0% w/v, about 1.5% w/v, about 2.0% w/v, or about 2.5% w/v,
about 0.05% w/v of tyloxapol;
about 0.2% w/v of carbomer homopolymer Type B;
about 2.0% of glycerin;
a tromethamine buffer; and
hydrochloric acid to adjust pH to about 6.4 to about 8.4;
about 0.05% w/v of sodium chloride; and
water qs to 100%;
wherein the formulation does not include a preservative.

In some embodiments of the formulations described herein, the polymorphic form B of compound I is is characterized by an X-ray diffraction pattern having three or more peaks at 2θ values selected from 9.3, 10.6 and 14.4.+−.0.2° 2θ.

In some embodiments, the formulations described herein have a viscosity of about 20 cP to about 200 cP.

In some embodiments, the formulations described herein have an osmolality of about 200 to about 450 milliosmoles per kilogram (mOsm/kg).

In some embodiments of the formulations described herein, the $D_{90}$ of compound (diameter at which 90% of compound I is comprised of smaller particles) is below about 10 μm, below about 8 μm, below about 6 μm, below about 4 μm, below about 3 μm, or about 2 μm. In some embodiments, the $D_{50}$ of compound I in the formulation (diameter at which 50% of compound I is comprised of smaller particles) is below about 10 μm, below about 8 μm, below about 6 μm, below about 4 μm, below about 3 μm, below about 2 μm, or about 1 μm. In some embodiments, the $D_{10}$ of compound I in the formulation (diameter at which 10% of compound I is comprised of smaller particles) is below about 5 μm, below about 4 μm, below about 3 μm, below about 2 μm, below about 1 μm, or about 0.3 μm.

In some embodiments of the formulations described herein the formulation exhibits settling of less than about 10%, less than about 8%, less than about 7%, less than about 6%, less than about 5%, less than about 4%, less than about 3%, or less than about 2% after storage at room temperature for six months.

In some embodiments of the formulations described herein, the amount of compound I in the formulation is at least 90% of the initial amount after about 6 months, after about 8 months, about 10 months, about 12 months, about 15 months, or about 18 months of storage under refrigeration.

In some embodiments of the formulations described herein, the amount of compound I in the formulation at least about 91%, at least about 92%, at least about 93%, at least about 94%, at least about 95%, at least 96%, at least about 97% or at least about 98% of the initial amount after about 18 months of storage under refrigeration.

In some embodiments of the formulations described herein, the formulation comprises no more than about 10% of a degradation product after 6 months under refrigeration, wherein the degradation product has a relative retention time of 1.23, compared to compound I, when analyzed by HPMC using a gradient 0.1% trifluoroacetic acid (TFA) water/acetonitrile mobile phase.

In some embodiments of the formulations described herein, no more than about 10% of compound I in the formulation degrades upon storage for 12 weeks at 40° C.

In some embodiments, the present disclosure is related to a method of making a formulation, comprising mixing an amount of 4-(7-Hydroxy-2-isopropyl-4-oxo-4H-quinazolin-3-yl)-benzonitrile (compound I) or a salt, co-crystal, or polymorph thereof, a non-ionic surfactant;

a suspending agent;

a tonicity agent;

a buffer;

a salt;

optionally, a preservative; and water qs to 100%, and adjusting the pH to a range of from about 5.5 to about 8.0.

In some embodiments, the method of making the formulations disclosed herein include the addition of compound I as a stock suspension. In some embodiments, the stock suspension is milled to achieve a desired particle size of compound I. In some embodiments, the $D_{90}$ of compound I in the formulation (diameter at which 90% of compound I is comprised of smaller particles) is below about 10 μm, below about 8 μm, below about 6 μm, below about 4 μm, below about 3 μm, or about 2 μm. In some embodiments, the $D_{50}$ of compound I in the formulation (diameter at which 50% of compound I is comprised of smaller particles) is below about 10 μm, below about 8 μm, below about 6 μm, below about 4 μm, below about 3 μm, below about 2 μm, or about 1 μm. In some embodiments, the $D_{10}$ of compound I in the formulation (diameter at which 10% of compound I is comprised of smaller particles) is below about 5 μm, below about 4 μm, below about 3 μm, below about 2 μm, below about 1 μm, or about 0.3 μm.

In one embodiment, the present disclosure provides a method of treating ocular surface pain in a subject in need thereof, comprising ocularly administering an effective amount of 4-(7-Hydroxy-2-isopropyl-4-oxo-4H-quinazolin-3-yl)-benzonitrile (Formula I) having structure:

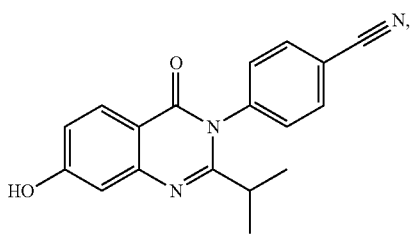

Formula I or a salt, solvate, polymorph, or co-crystal thereof to the subject.

In some embodiments, the ocular surface pain is episodic or acute pain. In some embodiments, the ocular surface pain is chronic ocular surface pain (COSP), lasting for at least about three months.

In some embodiments, the compound of formula I is administered to the cornea of the subject. In some embodiments, compound of formula I is administered to the subject at a concentration of about 0.5% w/v to about 3.5% w/v, about 0.5% w/v to about 2.5% w/v, or about 0.5% w/v to about 1.5% w/v, about 0.5% to about 3.0% w/v, about 1.0% to about 2.5% w/v, about 1.5% to about 3.0% w/v, or about 0.5% to about 2.5% w/v. In particular embodiments, the compound of formula I is administered at a concentration of about 0.5% w/v, about 1.0% w/v, about 1.5% w/v, about 2.0% w/v, about 2.5% w/v, about 3.0% w/v, or about 3.5% w/v.

In some embodiments of the methods to treat ocular surface pain described herein, the COSP is associated with dry eye disease. In some embodiments, the administration results in a decrease in the symptoms of dry eye disease. In particular embodiments, the administration results in a decrease in the ocular pain associated with dry eye disease. In some embodiments, the administration results in reduced incidence of at least about 10% in one or more of ocular dryness, ocular discomfort, ocular hyperemia, ocular burning or stinging, grittiness or foreign body sensation, or photophobia.

In some embodiments of the methods to treat ocular surface pain described herein, the subject suffers from one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, patients recovering from neurotrophic keratitis, or ocular pain persisting for at least three months after photorefractive keratectomy (PRK) surgery or laser-assisted in situ keratomileusis (LASIK) surgery.

In some embodiments, the methods to treat ocular surface pain described herein include administering an additional therapeutic agent to the subject.

In some embodiments of the methods to treat ocular surface pain described herein, the administration of compound I to the subject results in a reduction in a pain score of at least about 3, at least about 4, at least about 5, at least about 6, at least about 7, at least about 8, at least about 9 or at least about 10, compared to a placebo, when measured on a visual analog scale (VAS). In further embodiments, the administration of compound I to the subject results in a reduction in the subject's pain score of at least about 6, at least about 7, at least about 8, at least about 9 or at least about 10, compared to a placebo, when measured on the VAS.

In some embodiments of the methods to treat ocular surface pain described herein, the administration of compound I to the subject results in a reduction in the subject's pain of at least about 10%, at least about 15%, at least about 20%, or at least about 25%, compared to a placebo. In some embodiments, the reduction in the pain score arises from the difference in pain scores prior to and after administration of compound I to the subject. In some embodiments of the methods described herein, the administration of compound I to the subject the reduction in pain score occurs within about half hour after administration of compound I to the subject.

In some embodiments of the methods to treat ocular surface pain described herein, the administration of compound I to the subject results in a reduction in hyperemia in the subject of at least about 1, at least about 2, at least about 3, at least about 4, or at least about 5, on the McMonnies scale.

In some embodiments of the methods to treat ocular surface pain described herein, the administration of compound I to the subject results in a reduction in pain score within about half hour, within about 1 hour, within about 2 hours, or within about 4 hours after administration of compound I to the subject.

In some embodiments of the methods described herein, the administration of compound I to the subject the administration results in a reduction in hyperemia in the subject of at least about 1, at least about 2, at least about 3, at least about 4, or at least about 5, on the McMonnies scale.

In some embodiments of the methods described herein, the administration of compound I to the subject the administration does not result in a change in one or more of best corrected visual acuity, intraocular pressure, slit-lamp biomicroscopy, dilated eye exam, blink rate, or tear production, compared to a placebo.

In some embodiments of the methods described herein, the compound of formula I is administered in the form of a formulation described herein. In some embodiments of the methods described herein, the formulation is administered for at least about one, about two, or about three months. In some embodiments, the formulation is administered one to four times daily.

In some embodiments, the disclosure is related to a formulation as described herein for use in the treatment of ocular surface pain. In some embodiments, the ocular surface pain is acute or episodic ocular surface pain. In some embodiments, the ocular surface pain is chronic ocular surface pain lasting for at least 1 month, at least 2 months, or at least 3 months.

In some embodiments, the present disclosure relates to a method of reducing ocular surface pain in a subject in need thereof, comprising ocularly administering 4-(7-Hydroxy-2-isopropyl-4-oxo-4H-quinazolin-3-yl)-benzonitrile (Formula I) having structure:

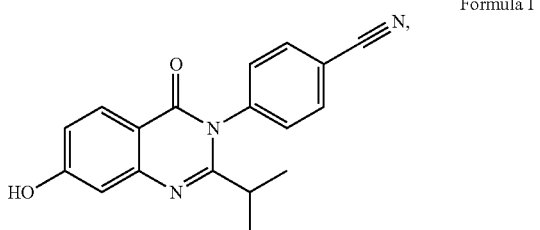

Formula I or a salt, solvate, polymorph, or co-crystal thereof to the subject.

In some embodiments, the ocular surface pain is acute or episodic ocular surface pain. In some embodiments, the ocular surface pain is chronic ocular surface pain lasting for at least 1 month, at least 2 months, or at least 3 months. In some embodiments, the COSP is associated with dry eye disease.

In some embodiments of the methods to reduce ocular pain described herein, the COSP is associated with dry eye disease. In some embodiments of the methods to reduce ocular surface pain described herein, the administration of compound I to the subject results in a decrease in the symptoms of dry eye disease.

In some embodiments of the methods to reduce ocular surface pain described herein, the administration of compound I to the subject results in a decrease in the ocular pain associated with dry eye disease. In some embodiments of the methods described herein, the administration of compound I to the subject results in reduced incidence of at least about 10% in one or more of ocular dryness, ocular discomfort, ocular hyperemia, ocular burning or stinging, grittiness or foreign body sensation, or photophobia.

In some embodiments, the subject in need of reducing ocular surface pain suffers from one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In some embodiments, the subject suffers from ocular pain persisting for at least three months after photorefractive keratectomy (PRK) surgery or laser-assisted in situ keratomileusis (LASIK) surgery.

In some embodiments, the methods to reduce ocular surface pain described herein include administering an additional therapeutic agent to the subject.

In some embodiments of the methods to reduce ocular surface pain described herein, the administration of compound I to the subject results in a reduction in the subject's pain score of at least about 3 as compared to a pain score prior to administration of the compound, when measured on a visual analog scale (VAS). In some embodiments of the methods described herein, the administration of compound I to the subject results in a reduction in a pain score of at least about 3, at least about 4, at least about 5, at least about 6, at least about 7, at least about 8, at least about 9 or at least about 10, compared to a placebo, when measured on a visual analog scale (VAS). In some embodiments of the methods described herein, the administration of compound I to the subject results in a reduction in the subject's pain score of at least about 6, at least about 7, at least about 8, at least about 9 or at least about 10, compared to a placebo, when measured on the VAS. In other embodiments, the reduction in pain score occurs after about 7 days of administration of compound I to the subject. In some embodiments, the reduction in pain score occurs after about 14 days of administration of compound I to the subject.

In some embodiments of the methods to reduce ocular surface pain described herein, the administration of compound I to the subject results in a reduction in the subject's pain of at least about 10%, at least about 15%, at least about 20%, or at least about 25%, compared to a placebo. In some embodiments of the methods described herein, the reduction in the pain score arises from the difference in pain scores prior to and after administration of compound I to the subject. In other embodiments, the reduction in pain score occurs after about 7 days of administration of compound I to the subject. In some embodiments, the reduction in pain score occurs after about 14 days of administration of compound I to the subject.

In some embodiments of the methods to reduce ocular surface pain described herein, the administration of compound I to the subject results in a reduction in hyperemia in the subject of at least about 1, at least about 2, at least about 3, at least about 4, or at least about 5, on the McMonnies scale.

In some embodiments of the methods described herein, the compound of formula i is administered as a formulation as described herein.

In some embodiments, the present disclosure relates to a method of reducing ocular hyperemia in a subject in need thereof, comprising ocularly administering 4-(7-hydroxy-2-isopropyl-4-oxo-4H-quinazolin-3-yl)-benzonitrile (Formula I) having structure:

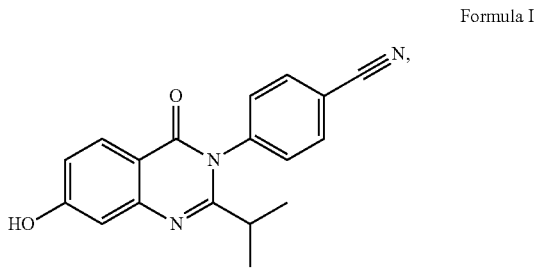 [SMILES: CC(C)c1nc2cc(O)ccc2c(=O)n1-c1ccc(C#N)cc1]

Formula I or a salt, solvate, polymorph, or co-crystal thereof to the subject; wherein the compound of formula I is administered at a concentration of about 0.5% w/v to about 3.5% w/v, about 0.5% w/v to about 2.5% w/v, or about 0.5% w/v to about 1.5 w/v, about 0.5% to about 3.0% w/v, about 1.0% to about 2.5% w/v, about 1.5% to about 3.0% w/v, or about 0.5% to about 2.5% w/v.

In some embodiments of the methods described herein, the reduction in ocular hyperemia is at least about 1, at least about 2, at least about 3, at least about 4, or at least about 5, on the McMonnies scale.

In some embodiments, the administration of compound I results in reduced incidence of at least about 10% in one or more of ocular dryness, ocular discomfort, ocular burning or stinging, grittiness or foreign body sensation, or photophobia.

In some embodiments of the methods described herein, the subject suffers from one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, patients recovering from neurotrophic keratitis, or ocular pain persisting for at least three months after photorefractive keratectomy (PRK) surgery or laser-assisted in situ keratomileusis (LASIK) surgery.

Some embodiments of the methods described herein to reduce ocular hyperemia further include administering an additional therapeutic agent to the subject.

In some embodiments of the methods described herein, the compound of formula I is administered as a formulation as described herein.

In some embodiments, the present disclosure relates to a method of treating or reducing ocular surface pain in a subject in need thereof, comprising administering to the subject a formulation comprising a compound 4-(7-hydroxy-2-isopropyl-4-oxo-4H-quinazolin-3-yl)-benzonitrile (compound I) having structure:

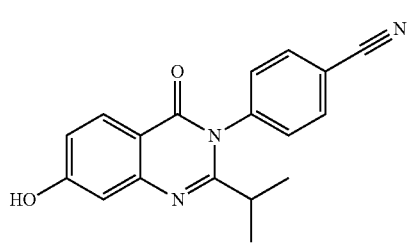 [SMILES: CC(C)c1nc2cc(O)ccc2c(=O)n1-c1ccc(C#N)cc1]

wherein the formulation results in a rabbit corneal Cmax compound I of about 1.5 to about 3 times conjunctival Cmax, wherein Cmax is the maximum concentration of compound I in the specified tissue after administration of a single dose. In some embodiments, the compound I is administered as a formulation as described herein.

In some embodiments, the present disclosure relates to a method of treating or reducing ocular surface pain in a subject in need thereof, comprising administering to the subject a formulation comprising a compound 4-(7-hydroxy-2-isopropyl-4-oxo-4H-quinazolin-3-yl)-benzonitrile (compound I) having structure:

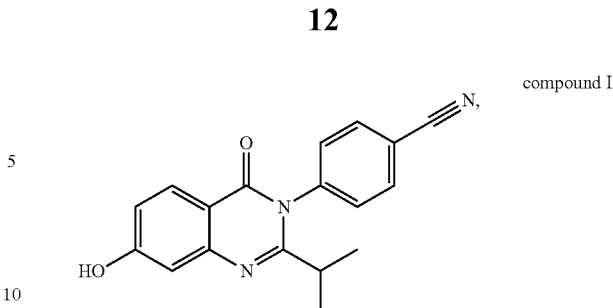

wherein the formulation results in a Cmax of compound I in a rabbit cornea of about 500 times the Cmax of compound I in plasma, wherein Cmax is the maximum concentration of compound I in the specified tissue after administration of a single dose. In some embodiments, the compound I is administered as a formulation as described herein.

Specific preferred embodiments of the invention will become evident from the following more detailed description of certain preferred embodiments and the claims.

BRIEF DESCRIPTION OF THE DRAWINGS

In FIG. 1A, the formulation with percent of compound I at about 70% of original at 12 weeks is the formulation of compound I as a solution. In FIG. 1B, the formulation with percent of compound I at about 20% of original at 12 weeks is the formulation of compound I as a solution.

FIG. 5A provides the results from question 4: 24 hr Eye Pain When Most Painful (pain level), FIG. 5B provides results from Question 5: 24 hr Eye Pain When Least Painful (pain level), and FIG. 5C provides results from Question 6 24 hr Eye Pain On Average (pain level). For each of FIGS. 5A, 5B, and 5C, the dashed line with "x" represents vehicle, and the solid line with circles (o) represents compound I.

FIG. 6A provides results from Question 22: How Often Eye Pain With Redness (%). FIG. 6B provides results from Question 23: How Often Eye Pain With Burning (%). FIG. 6C provides results from Question 24: How Often Eye Pain With Sensitivity (%). FIG. 6D provides results from Question 25: How Often Eye Pain With Tearing (%). For each of FIGS. 6A, 6B, 6C, and 6D, the dashed line with "x" represents vehicle, and the solid line with circles (o) represents compound I.

DETAILED DESCRIPTION

Figure 1A:
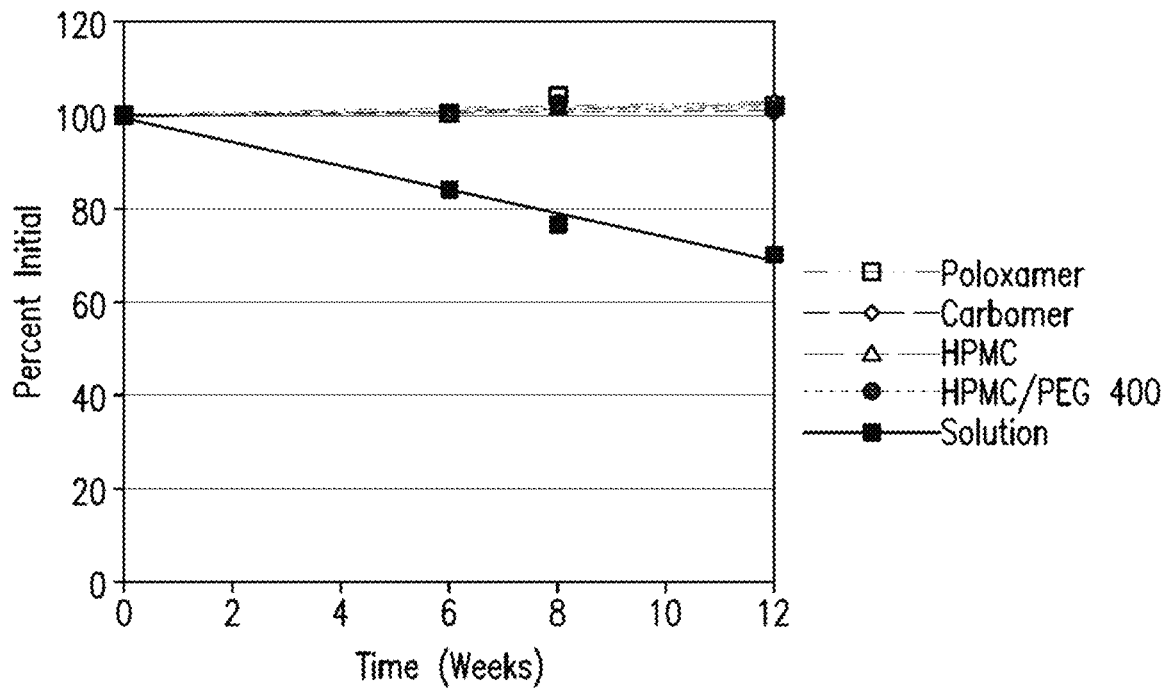
FIG. 1A shows the percent of compound I in the exploratory formulations described in Table 2 through 12 weeks at room temperature.

"TRPV1 receptor" refers to the Transient Receptor Potential Vanilloid 1 that has been characterized through molecular cloning and pharmacology. See e.g., Caterina M J, et al., *Nature* 1997; 389:816-824. TRPV1 receptor activity is measured as described in WO2005/120510, hereby incorporated by reference in its entirety.

The language "effective amount" of the compounds described herein, refers to that amount of a therapeutic compound necessary or sufficient to perform its intended function within a mammal. An effective amount of the therapeutic compound can vary according to factors such as the amount of the causative agent already present in the mammal, the age, sex, and weight of the mammal, and the ability of the therapeutic compounds of the present disclosure to treat the ocular surface disorder and/or symptoms thereof in the mammal.

The phrase "ophthalmically compatible" refers to formulations, polymers and other materials and/or dosage forms which are suitable for use in contact with the ocular tissues of human beings and animals without excessive toxicity, irritation, allergic response, or other problem or complication, commensurate with a reasonable benefit/risk ratio.

As used herein, the term "treat", "treating" or "treatment" in connection to a disease or disorder refers in some embodiments, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder or symptom thereof.

As used herein, the term "subject" or "patient" refers to human and non-human mammals, including but, not limited to, primates, rabbits, pigs, horses, dogs, cats, sheep, and cows. In particular embodiments, a subject or patient is a human. In some embodiments, the term "patient" or "subject" refers to a human being who is diseased with the condition (i.e., disease or disorder) described herein and who would benefit from the treatment. As used herein, a subject is "in need of" a treatment if such subject (patient) would benefit biologically, medically or in quality of life from such treatment. In particular embodiments, the subject is an adult human of at least about 18 years of age. In some embodiments, the subject is an adult human from about 18 years of age to about 75 years of age. In some embodiments, the subject is a child of up to about 18 years of age.

As used herein, "ocular surface" refers to the outer surface of the eye, which anatomically comprises the cornea (with epithelium, bowman layer, stroma, descement membrane, endothelium), conjunctiva, cul de sac, and the corneo-scleral junction, i.e., limbus.

As used herein, ocular administration includes administration to all parts of the eye including all parts of the ocular surface such as the cornea, conjunctiva, the cul de sac and the corneo-scleral junction, i.e., limbus.

As used herein, "pain" refers to constant or intermittent sensation of actual pain described as but not limited to stabbing, dull, sharp, or ache. Pain may also refer to similar related descriptors such as but not limited to burning, stinging, grittiness, foreign body sensation, dryness, sandy, tired, itchy, irritated, sensitivity to light.

As used herein, "ocular surface pain" refers to pain on the surface of the eye, e.g., cornea. Ocular pain may be nociceptic pain, which is generally caused by external physical or chemical damaging stimuli such as corneal surgery, inflammation, or other damage to the corneal surface. Ocular pain may also result from neuropathic pain, which may occur due to direct damage to the neurons of the body, resulting in messages of pain being sent to the central nervous system and brain regardless of the presence of noxious stimuli. As used herein "ocular surface pain" includes both nociceptic pain and neuropathic pain.

As used herein, the term "visual analog scale" (VAS) is a measure of pain intensity where a subject typically marks a place on a scale that aligns with their level of pain. The pain is marked in a range of "no pain" (score of 0) and "pain as bad as it could be" or "worst imaginable pain" (score of 100). See e.g., Hawker, et al., *Arthritis Care & Research* 63(11), pp. S240-S252 (November 2011). There are several other well-designed pain scales that may be used to help assess the extent of pain. The numerical rating scale (NRS) is often used, in which subjects use numbers to rate pain. The number scale may be from 1-10, or 1-100. The Wong-Baker FACES Pain Scale combines pictures and numbers for pain ratings. It can be used in children over the age of 3 and in adults. Six faces depict different expressions, ranging from happy to extremely upset. Each is assigned a numerical rating between 0 (smiling) and 10 (crying). The Verbal Pain Intensity Scale uses wordings on a scale to rate pain intensity: No Pain/Mild Pain/Moderate Pain/Severe Pain Very Severe Pain/Worst Possible Pain.

The Eye Sensation Scale is a specific pain scale was developed to measure ophthalmic pain severity. See Caudle L. E. et al., Optom Vis Sci. 2007 August; 84(8):752-62. In this scale, pain, discomfort or light sensitivity is typically measured by 5 category labels of "extreme," "severe," "moderate," "mild," or "none."

The Ocular Pain Assessment Survey (OPAS) is a quantitative, multidimensional questionnaire, specifically designed for assessment of corneal and ocular surface pain and Quality of Life (QoL) changes. The OPAS assesses pain intensity, frequency of eye and non-eye pain, QoL changes, aggravating factors, associated factors, and symptomatic relief quantitative, allowing for monitoring of treatment responses. See Qazi et al., *Ophthalmology* July 123(7):1458-1468 (2016).

As used herein, the term "Visual Tasking Questionnaire" refers to a questionnaire that asks the subject to subjectively rate how much difficulty they have conducting certain activities that require a fixed or prolonged stare that may exacerbate ocular pain. The questionnaire also asks about coping mechanisms associated with the difficulties they experience during visual tasking activities.

As used herein, ocular hyperemia refers to redness of the ocular surface. Ocular hyperemia may be a clinical marker for inflammation and/or ocular irritation. Ocular hyperemia may be measured using the McMonnies scale, at values from 0 to 5, based on standard photographs.

As used herein, "placebo" refers to an ophthalmic formulation that includes all the components of the administered drug composition without the drug.

As used herein, the term "about" refers to a range of values+10% of a specified value.

As used herein, "Compound of formula I," "Compound I," "Formula I," and "compound I" are used interchangeably and mean a compound that has the name 4-(7-hydroxy-2-isopropyl-4-oxo-4H-quinazolin-3-yl)-benzonitrile, the structure shown below, and can be synthesized using procedures known in the art and described in WO2005/120510 and U.S. Pat. No. 8,349,852 ("Quinazolinone derivatives useful as vanilloid antagonists") to Chen et al., both of which are hereby incorporated by reference in their entireties.

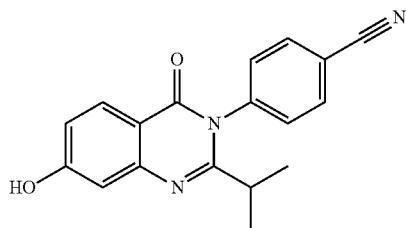

Compound I may be used in amorphous or crystalline forms. Additionally or alternatively, various crystalline and polymorphic forms of Compound (I) may be used. As used herein, "polymorphic forms" or "polymorphs" of compound (I) is intended to encompass crystalline hydrates or other crystalline solvates of compound (I).

Any chemical formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen, carbon, nitrogen, and oxygen, such as $^3H$, $^{11}C$, $^{13}C$, $^{14}C$, and $^{15}N$. Accordingly, it should be understood that methods of the present invention can or may involve compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$) reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. Isotopically-labeled compounds can generally be prepared by conventional techniques known to those skilled in the art, e.g., using an appropriate isotopically-labeled reagents in place of the non-labeled reagent previously employed.

The present invention encompasses embodiments that include all pharmaceutically acceptable salts of the compounds useful according to the invention provided herein. As used herein, "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts of the parent compound formed, for example, from non-toxic inorganic or organic acids. The pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, $17^{th}$ ed., Mack Publishing Company, Easton, Pa., 1985, p. 1418 and *Journal of Pharmaceutical Science*, 66, 2 (1977), each of which is incorporated herein by reference in its entirety. For example, preferred pharmaceutically acceptable salts include, but are not limited to, mineral or organic acid salts of basic residues such as amines. For example, the salt can be a hydrochloride salt. Other examples of suitable salts can be found in U.S. Pat. No. 8,349,852, the content of which is hereby incorporated by its entirety.

The phrase "pharmaceutically acceptable" as employed herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Unless indicated otherwise, all ingredient concentrations are presented in units of % weight/volume (% w/v). As is commonly understood, the % w/v value refers to the amount of the particular component or ingredient in the formulation. It is commonly understood that equivalent concentrations can be expressed in different units. For example, a concentration of 0.1% w/v can also be expressed as a 1 mg/ml solution.

Unless otherwise specified, the weight or dosage referred to herein for the compound of formula I is the weight or dosage of the compound itself, not that of a salt or prodrug thereof, which can be different to achieve the intended therapeutic effect. For example, the weight or dosage of a corresponding salt of a compound suitable for the methods, compositions, or combinations disclosed herein may be calculated based on the ratio of the molecular weights of the salt and compound itself.

The present invention provides formulations of the compound of formula I. In some embodiments, the formulations are aqueous suspensions of a compound of formula I. In some embodiments, the suspension includes the compound of formula I at a concentration of from about 0.5% to about 1.5% w/v, about 0.5% to about 2.5% w/v, about 0.5% to about 3.5% w/v, about 0.5% to about 3.0% w/v, about 1.0% to about 2.5% w/v, about 1.5% to about 3.0% w/v, about 0.5% to about 2.5% w/v. In some embodiments, the concentration of the compound of formula I in a formulation for topical ocular use is at least about 0.5% w/v, at least about 1.0% w/v, at least about 1.5% w/v, at least about 2.0% w/v, or at least about 2.5% w/v. In some embodiments, the concentration of the compound of formula I in a formulation for topical use is no more than about 5.0% w/v, no more than about 4.5% w/v, no more than about 4.0% w/v, no more than about 3.5% w/v, or no more than about 3.0% w/v. In particular embodiments, the concentration of the compound of formula I in a formulation for topical use is about 0.5% w/v, about 1.0% w/v, about 1.5% w/v, about 2.0% w/v, about 2.5% w/v, about 3.0% w/v, or about 3.5% w/v. Expressed in units of mg/ml, in some embodiments, compound of formula I is administered to the subject at a concentration of about 5 mg/ml to about 35 mg/ml, about 5 mg/ml to about 25 mg/ml, or about 5 mg/ml to about 15 mg/ml, about 5 mg/ml to about 30 mg/ml, about 10 mg/ml to about 25 mg/ml, about 15 mg/ml to about 30 mg/ml, or about 5 mg/ml to about 25 mg/ml. In some embodiments, the concentration of the compound of formula I in a formulation for topical use is at least about 5 mg/ml, at least about 10 mg/ml, at least about 15 mg/ml, at least about 20 mg/ml, or at least about 25 mg/ml. In some embodiments, the concentration of the compound of formula I in a formulation for topical use is no more than about 50 mg/ml, no more than about 45 mg/ml, no more than about 40 mg/ml, no more than about 35 mg/ml, or no more than about 30 mg/ml. In particular embodiments, the compound of formula I is administered at a concentration of about 5 mg/ml, about 10 mg/ml, about 15 mg/ml, about 20 mg/ml, about 25 mg/ml, about 30 mg/ml, or about 35 mg/ml.

In some embodiments, the compound of formula is present as polymorph form B, as described in U.S. Pat. No. 8,349,852, incorporated by reference herein. In some embodiments, polymorph B is characterized by an X-ray diffraction pattern having three or more peaks at 2θ values selected from 9.3, 10.6 and 14.4±0.2° 2θ, when recorded using CuK$_\alpha$ radiation. In some embodiments, polymorph B is characterized by an X-ray diffraction pattern having three or more peaks at 2θ values selected from 9.3, 10.6, 14.4, 15.5, 17.9, 19.9, 23.4±0.2° 2θ, when recorded using CuK$_\alpha$ radiation. In some embodiments, polymorph B is characterized by an X-ray diffraction pattern having three or more peaks at 2θ values selected from 9.3, 10.6, 12.8, 14.4, 15.5, 17.9, 19.9, 21.3, 23.4, and 28.0±0.2° 2θ, when recorded using CuK$_\alpha$ radiation.

In some embodiments of the formulations described herein, the D$_{90}$ of compound I in the formulation (diameter at which 90% of compound I is comprised of smaller particles) is below about 10 μm, below about 8 μm, below about 6 μm, below about 4 μm, below about 3 μm, or about 2 μm. In some embodiments, the D$_{50}$ of compound I in the formulation (diameter at which 50% of compound I is comprised of smaller particles) is below about 10 μm, below about 8 μm, below about 6 μm, below about 4 μm, below about 3 μm, below about 2 μm, or below about 1 μm. In some embodiments, the D$_{10}$ of compound I in the formulation (diameter at which 10% of compound I is comprised of smaller particles) is below about 5 μm, below about 4 μm, below about 3 μm, below about 2 μm, below about 1 pin, or about 0.3 μm.

In some embodiments, the formulation further includes at least one ophthalmically acceptable excipient.

In some embodiments, the formulations include an ophthalmically acceptable surfactant. In some embodiments, the surfactant is an anionic surfactant. In specific embodiments, the anionic surfactant is selected from $C_{10}$-$C_{22}$alkylsulfates, $C_{10}$-$C_{22}$alkyl(oligooxyalkylene)sulfates, $C_4$-$C_{22}$ alkyl sulfosuccinate esters, $C_{10}$-$C_{22}$acylsarcosinatesand $C_{10}$-$C_{22}$ alkylcarboxylates; wherein oligooxyalkylene moieties have from one to five oxy-$C_1$-$C_6$ alkylene moieties, e.g., oxyethylene moieties. The anionic surfactants may have a countercation is selected from alkali metal, e.g., sodium, $C_1$-$C_3$ alkylammonium, tri($C_1$-$C_3$ alkanol)ammonium, e.g., triethanolammonium, di($C_1$-$C_3$ alkanol)ammonium and ammonium cations. The concentration of anionic surfactant in the formulation is from about 0.005 to 0.1 g/L, or 0.005 to 0.05 g/L. In some embodiments, the surfactant is a cationic surfactant. Non-limiting examples of cationic surfactants include alkylamine salts, alkylamine polyoxyethylene adduct, a fatty acid triethanolamine monoester salt, acyl aminoethyl diethylamine salts, fatty acid polyamine condensates, alkyl imidazolines, 1-acyl aminoethyl-2-alkyl imidazoline, 1-hydroxyethyl-2-alkyl imidazoline, include chlorhexidine or the like salts thereof, chlorhexidine or a salt thereof, e.g., chlorhexidine gluconate. In some embodiments, the cationic surfactant is present in the formulation in an amount of from about 0.001 to about 5% w/v, or about 0.001 to about 1% w/v, or about 0.001 to about 0.1% w/v, or about 0.001 to about 0.01% w/v, or about 0.001 to about 0.005% w/v.

In specific embodiments, the surfactant is a non-ionic surfactant. In some embodiments, the non-ionic surfactant is a polysorbate surfactant, a block copolymer of ethylene oxide and propylene oxide surfactant (e.g., a pluronic or tetronic surfactant), poloxamer, tyloxapol, or combinations thereof. Tyloxapol is a nonionic liquid polymer of the alkyl aryl polyether alcohol type. Poloxamers are nonionic triblock copolymers composed of a central hydrophobic chain of polyoxypropylene (poly(propylene oxide)) flanked by two hydrophilic chains of polyoxyethylene (poly(ethylene oxide)). In particular embodiments, the non-ionic surfactant is tyloxapol. In some embodiments, the tyloxapol is present in an amount at least about 0.001% w/v, at least about 0.01% w/v, at least about 0.02% w/v, at least about 0.03% w/v, at least about 0.04% w/v, and no more than about 1% w/v, no more than about 0.5% w/v, no more than about 0.3% w/v, or no more than about 0.2% w/v, no more than about 0.1% w/v, or no more than about 0.08% w/v. In particular embodiments, the non-ionic surfactant is tyloxapol, present in an amount of about 0.03% w/v to 0.08% w/v, or about 0.05% w/v. In particular embodiments, the surfactant is substantially all tyloxapol.

In some embodiments, the formulations include about 15-20% w/v of a poloxamer surfactant. In some embodiments, the formulations include about 15, about 15.5%, about 16%, about 16.5%, about 17%, about 17.5%, about 18%, about 18.5%, about 19%, about 19.5%, or about 20% w/v of poloxamer. In particular embodiments, the formulations include about 17% to about 18% w/v, or about 17.5% w/v poloxamer. In yet particular embodiments, the poloxamer is Poloxamer 407. In particular embodiments, the surfactant is substantially all tyloxapol.

In some embodiments, the formulations include a suspending agent. In some embodiments, the suspending agent is a carbomer, hydroxypropyl methyl cellulose (hypromellose), polyethylene glycol, or combinations thereof. Carbomers are carboxyvinyl polymers that have a network of cross-linked polymer chains. The polymers are often characterized as having carboxylic acid functional groups and preferably contain from 2 to 7 carbon atoms per functional group. Carbomers, i.e. synthetic high-molecular-weight polymers of acrylic acid that are crosslinked e.g. with allyl sucrose or allyl ethers of pentaerythritol, particularly water-soluble and water-swellable carbomers. Carbomers are available under the trade name CARBOPOL® from various suppliers In particular embodiments, the carbomer is carbomer homopolymer Type B. In particular embodiments, the carbomer is CARBOPOL® 934P (Carbomer 934P), 940 or 974P. In some embodiments, the suspending agent is carbomer and is present in the formulation in an amount of at least about 0.05% w/v, at least about 0.1% w/v, or at least about 0.2% w/v, and no greater than about 1.0% w/v, no greater than about 0.6% w/v, or no greater than about 0.5%. In particular embodiments, the suspending agent is carbomer, and is present in the formulation in an amount of 0.1% w/v to about 0.3% w/v, or about 0.2% w/v.

In some embodiments, the suspending agent is hydroxypropyl methyl cellulose. In particular embodiments, the hydroxypropyl methyl cellulose is present in the formulation in an amount of at least about 0.05% w/v, at least about 0.1% w/v, or at least about 0.25% w/v, and less than about 1.8% w/v, less than about 1.0% w/v, less than about 0.8% w/v, or less than about 0.6% w/v. In some embodiments, the hydroxypropyl methyl cellulose is present in the formulation in an amount of from about 0.1% w/v to about 0.8 w/v %; from about 0.1% w/v to about 0.6% w/v; from about 0.25% w/v to about 0.8% w/v; from about 0.4% w/v to about 0.6% w/v.

In some embodiments, the suspending agent is a polyethylene glycol (PEG) having molecular weight of at least about 200 Da. In some embodiments, the PEG has a molecular weight of at least about 400, 1,000, 2,000, 3,000, 4,000, 6,000, or about 10,000 Da. In some embodiments, the suspending agent is a polyethylene glycol (PEG) having molecular weight of from about 200 to about 20,000 Da. In some embodiments, the PEG has a molecular weight of about 400, 1,000, 2,000, 3,000, 4,000, 6,000, or about 10,000 Da. In some embodiments, the PEG is present in the formulation in an amount of at least 1% w/v, at least about 2% w/v, at least about 3% w/v, and less than about 10% w/v, less than about 9% w/v, or less than about 8% w/v. In particular embodiments, the suspending agent is PEG400 at a concentration of from about 4% w/v to about 9% w/v, about 5% w/v to about 8% w/v, or about 7% w/v. In particular embodiments, the suspending agent is PEG6000 at a concentration of from about 1% w/v to about 4% w/v, about 1% w/v to about 3% w/v, or about 2% w/v.

In particular embodiments, the suspending agent is a combination of more than one suspending agent. In other embodiments, the suspending agent is substantially all carbomer.

In some embodiments, the suspending agent can provide the desired viscosity of the formulation. Without being bound by theory, it is believed that suspending agents may increase the viscosity of the formulation. A formulation with appropriate viscosity is beneficial in maintaining compound I in a suspended state in the formulation without settling and caking. In some embodiments, the formulation viscosity is from about 10 to about 200 cP (centipoise), from about 20 cP to about 200 cP, or from about 20 cP to about 150 cP. In some embodiments, the formulation viscosity is at least about 10 cP, 20 cP, 50 cP, 100 cP, or at least about 150 cP. Viscosity measurements for the formulations are measured using a Brookfield viscometer using spindle CP-42 at either 3 rpm or 60 rpm. Viscosity is typically measured at room temperature, i.e., 25° C.

In some embodiments, the formulation includes a tonicity agent. In some embodiments, the tonicity agent is a polyol. As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. In some embodiments, the tonicity agent is a polyol such as sugars, sugar alcohols and sugar acids, including, but not limited to: mannitol, glycerin, xylitol, sorbitol and propylene glycol, or combinations thereof. In particular embodiments, the composition includes mannitol, glycerin or a combination thereof. In some embodiments, the amount of polyol in the formulation is from about 0.05% w/v to about 10% w/v, from about 0.1% to about 8% w/v, from about 0.1% to about 7% w/v, from about 0.1% to about 5% w/v. In particular embodiments, the tonicity agent is mannitol or glycerin, which is present in the formulation in an amount of from 0.1% w/v to about 5% w/v, or about 0.2% w/v, about 0.3% w/v, about 0.4% w/v, about 0.5% w/v, about 1% w/v, about 2% w/v, about 2.5% w/v, about 3.0% w/v, about 3.5% w/v, about 4.0% w/v, about 4.5% w/v, or about 5% w/v. In particular embodiments, the tonicity agent is mannitol. In particular embodiments, the tonicity agent is glycerin.

In some embodiments, the formulation includes a buffer. Non limiting examples of buffer substances include acetate, ascorbate, borate, hydrogen carbonate, carbonate, citrate, edetate (EDTA) gluconate, lactate, phosphate, propionate and TRIS (tromethamine) buffers. In particular embodiments, the buffer is a phosphate buffering system. In particular embodiments, the buffer is a tromethamine buffer. The amount of buffer substance added is, typically, that necessary to ensure and maintain a physiologically tolerable pH range. In some embodiments, the pH range is in the range of from about 4 to about 9, from about 4.5 to about 8.5, from about 5.0 to about 8.0, from about 5.5 to about 8.0, from about 6.4 to about 8.4. In some embodiments, the pH is about 6.0. In particular embodiments, the pH is about 7.4. In some embodiments, the pH of the formulation is about 5.0 to about 8.0, about 5.5 to about 7.5, about 5.0 to about 7.4, about 5.5 to about 7.4, about 6.0 to about 8.0, about 6.5 to about 8.0, about 6.0 to about 7.4, or about 6.5 to about 7.4.

In some embodiments, the formulation includes a salt. In some embodiments, salt is sodium chloride, potassium chloride, calcium chloride, or magnesium chloride. In particular embodiments, the salt is sodium chloride. In particular embodiments, the salt is present in an amount of at least about 0.01% w/v, at least about 0.02% w/v, at least about 0.03% w/v, at least about 0.04% w/v, and no more than about 0.5% w/v, no more than about 0.4% w/v, no more than about 0.3% w/v, no more than about 0.2% w/v, or no more than about 0.1% w/v. In particular embodiments, the salt is present in an amount of from about 0.01% w/v to about 0.5% w/v, from about 0.02% w/v to about 0.4% w/v, from about 0.03% w/v to about 0.3% w/v, from about 0.04% w/v to about 0.2% w/v, from about 0.05% w/v to about 0.1% w/v. In particular embodiments, the salt is sodium chloride and is present in the formulation in an amount of about 0.02% to about 0.07% w/v, or about 0.05% w/v.

In some embodiments, the formulations described herein have an osmolality of about 200 to about 450 milliosmoles per kilogram (mOsm/kg), about 200 to about 400 mOsm/kg, about 200 to about 300 mOsm/kg, or about 240 to about 360 mOsm/kg.

In some embodiments, the formulation may also be self-preserved and does not include a preservative. In other embodiments, the formulation includes a preservative. In some embodiments, the preservative includes, without limitation, polyhexylmethylene biguanidine (PHMB), polymeric quaternary ammonium compound (e.g., polyquatemium-1), chlorine containing preservatives such as benzalkonium chloride (BAK), chlorite preservatives or others.

In some embodiments, the preservative is polymeric quaternary ammonium compounds that are ophthalmically acceptable. Compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.). In particular embodiments, the polymeric ammonium compound is polyquatemium 1, otherwise known as POLYQUAD® or ONAMERM® with a number average molecular weight between 2,000 to 30,000. In still particular embodiments, the number average molecular weight is between 3,000 to 14,000.

When used, the polymeric quaternary ammonium compound is generally used in an amount that is greater than about 0.00001 w/v %, greater than about 0.0003 w/v %, or greater than about 0.0007 w/v % of the formulation. Moreover, the polymeric quaternary ammonium compound, when used in the formulation, is generally used at a concentration that is less than about 0.03 w/v %, less than about 0.003 w/v %, or less than about 0.0015 w/v % of the formulation. In some embodiments, the concentration of polymeric quaternary ammonium compound in the formulation are as follows: greater than about 0.0003 w/v % but less than about 0.003 w/v %; greater than about 0.0003 w/v % but less than about 0.0015 w/v %; greater than about 0.0007 w/v % but less than about 0.003 w/v %; and greater than about 0.0007 w/v % but less than about 0.0015 w/v %. In particular embodiments, the formulation includes polyquartemium 1 at a concentration of about 0.001% w/v.

In some embodiments, the formulation includes BAK at a concentration that is at least about 0.0005 w/v %, about 0.001 w/v %, or greater than about 0.007 w/v % of the formulation, and at a concentration that is less than about 0.1 w/v %, less than about 0.02 w/v %, or less than about 0.0035 w/v % of the ophthalmic composition. It is specifically contemplated that any of the lower limits on the concentration of BAK may be used in conjunction with any of the upper limits on the concentrations of BAK. In particular embodiments, the concentration of BAK in the composition are as follows: greater than about 0.001 w/v % but less than about 0.02 w/v %; greater than about 0.001 w/v % but less than about 0.0035 w/v %; greater than about 0.007 w/v % but less than about 0.02 w/v %; and greater than about 0.007 w/v % but less than about 0.0035 w/v %.

In some embodiments, described herein is an aqueous formulation that includes:
4-(7-hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v,
and one or more excipients selected from the group consisting of a surfactant, a suspending agent, a tonicity agent, a buffer, a preservative, a salt, and a preservative.

In some embodiments, described herein is an aqueous formulation that includes:
4-(7-hydroxy-2-isopropyl-4-oxo-4H-quinazolin-3-yl)-benzonitrile (compound I) or a salt, co-crystal, or polymorph thereof, present as a suspension in the formulation, in an amount of about 0.5% w/v to about 3.5% w/v,
and one or more excipients selected from the group consisting of a surfactant, a suspending agent, a tonicity agent, a buffer, a preservative, a salt, and a preservative.

In some embodiments, described herein is an aqueous formulation that includes:
4-(7-hydroxy-2-isopropyl-4-oxo-4H-quinazolin-3-yl)-benzonitrile (compound I) or a salt, co-crystal, or polymorph thereof, present as a suspension in the formulation,
and one or more excipients selected from the group consisting of a surfactant, a suspending agent, a tonicity agent, a buffer, a preservative, a salt, and a preservative.

In some embodiments, described herein is an aqueous formulation that includes:
a suspension of 4-(7-hydroxy-2-isopropyl-4-oxo-4H-quinazolin-3-yl)-benzonitrile (compound I) or a salt, co-crystal, or polymorph thereof,
and one or more excipients selected from the group consisting of a surfactant, a suspending agent, a tonicity agent, a buffer, a preservative, a salt, and a preservative.

In some embodiments, described herein is an aqueous formulation that includes:
4-(7-hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, present as a suspension in the formulation
a surfactant,
a suspending agent,
and one or more excipients selected from the group consisting of a tonicity agent, a buffer, a preservative, a salt, and a preservative.

In some embodiments, the invention described herein is a formulation that includes:
4-(7-hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v, present as a suspension in the formulation,
a non-ionic surfactant;
a suspending agent;
a tonicity agent;
a buffer;
a salt; and
optionally, a preservative.

In some embodiments, the invention described herein is a formulation that includes:
a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v,
a non-ionic surfactant;
a suspending agent;
a tonicity agent;
a buffer;
a salt;
optionally, a preservative; and
water qs to 100%.

In some embodiments, the invention described herein is a formulation that includes:
a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v to about 2.5% w/v,
a non-ionic surfactant selected from tyloxapol, poloxamer, or combinations thereof in an amount of from about 0.01 to 0.2% w/v;
a suspending agent selected from hydroxypropyl methyl cellulose, polyethylene glycol or carbomer homopolymer Type B;
a tonicity agent selected from polyols in an amount of from about 0.05% w/v to about 10% w/v;

a buffer selected from edetate, phosphate, borate, or combinations thereof;
a salt; and
water qs to 100%; and
a pH in the range of from about 5.5 to about 8.0.

In some embodiments, the invention described herein is a formulation that includes:
a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v, about 1.0% w/v, about 1.5% w/v, about 2.0% w/v, or about 2.5% w/v,
a non-ionic surfactant selected from tyloxapol in an amount of about 0.04 w/v to about 0.06% w/v, poloxamer in an amount of about 0.005-0.12% w/v, or combinations thereof;
a suspending agent selected from hydroxypropyl methyl cellulose in an amount of from about 0.1% w/v to about 0.8 w/v %, polyethylene glycol in an amount of from about 2% w/v to about 8% w/v, carbomer homopolymer Type B in an amount from about 0.05% w/v to about 0.5% w/v, or combinations thereof;
a tonicity agent selected from mannitol or glycerin in an amount of from about 0.1% w/v to about 5% w/v;
a buffer selected from edetate, phosphate, borate, tromethamine, or combinations thereof;
sodium chloride in an amount of from 0.01% w/v to about 1% w/v;
water qs to 100% and
a pH in the range of from about 5.5 to about 8.0.

In some embodiments, the invention described herein is a formulation that includes:
a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v, about 1.0% w/v, about 1.5% w/v, about 2.0% w/v, or about 2.5% w/v,
tyloxapol in an amount of about 0.04 w/v to about 0.06% w/v;
carbomer homopolymer Type B in an amount from about 0.05% w/v to about 0.4% w/v;
glycerin in an amount of from about 0.5% w/v to about 5% w/v;
a buffer selected from edetate, phosphate, borate, tomethamine, or combinations thereof;
sodium chloride in an amount of from 0.01% w/v to about 1% w/v;
water qs to 100% and
a pH in the range of from about 5.5 to about 8.0.

In some embodiments, the invention described herein is a formulation that includes:
a suspension of polymorphic form B of 4-(7-Hydroxy-2-isopropyl-4-oxo-4H-quinazolin-3-yl)-benzonitrile (compound I), in an amount of about 0.5% w/v, about 1.0% w/v, about 1.5% w/v, about 2.0% w/v, or about 2.5% w/v,
tyloxapol in an amount of about 0.04 w/v to about 0.06% w/v;
carbomer homopolymer Type B in an amount from about 0.05% w/v to about 0.4% w/v;
glycerin in an amount of from about 0.5% w/v to about 5% w/v;
a buffer selected from edetate, phosphate, borate, tomethamine, or combinations thereof;
sodium chloride in an amount of from 0.01% w/v to about 1% w/v;
water qs to 100% and
a pH in the range of from about 5.5 to about 8.0.

In some embodiments, the invention described herein is a formulation that includes:
a suspension of polymorphic form B of 4-(7-Hydroxy-2-isopropyl-4-oxo-4H-quinazolin-3-yl)-benzonitrile (compound I), in an amount of about 0.5% w/v, about 1.0% w/v, about 1.5% w/v, about 2.0% w/v, or about 2.5% w/v,
about 0.05% w/v of tyloxapol;
about 0.2% w/v of carbomer homopolymer Type B;
about 2.0% of glycerin;
a tromethamine buffer;
about 0.05% w/v of sodium chloride; and
water qs to 100% and
a pH in the range of from about 6.4 to about 8.4;
wherein the formulation does not include a preservative.

In some embodiments, acids or bases such as hydrochloric acid, sodium hydroxide, or combinations thereof are used to adjust pH of the formulation. In particular embodiments, hydrochloric acid is used to adjust pH to about 6.0, or about 7.4.

In some embodiments, the formulations described herein are aqueous, that is, they include at least about 90%, at least about 92%, or at least about 95% water.

Without being bound by theory, it is believed that the viscosity of formulations with carbomer homopolymer Type B increases as the pH is adjusted from acidic to neutral, but the viscosity decreases with increasing ionic strength. The present inventors found that using tromethamine as the buffer increases pH without substantial increases in ionic strength. Without further being bound by theory, the inventors also found that glycerin is able adjust the tonicity of the formulation without increasing its ionic strength. Glycerin is also well-tolerated and non-irritating and also serves as a humectant and an additional viscosity agent.

Without being bound by any particular theory, the present inventors also found that inclusion of a surfactant in the formulation acts as a wetting agent for the compound of formula I, thereby providing adequate wetting of the particles of compound I while decreasing the potential for irritation and foaming and aiding in redispersibility of the suspension.

In some embodiments, the formulations described herein further include additional components. In particular embodiments, the formulation includes a cyclodextrin derivative, for example, β-cyclodextrin derivative, γ-cyclodextrin derivative or a combination thereof. In particular embodiments, the cyclodextrin is a hydroxypropyl β-cyclodextrin or sulfoalkylether β-cyclodextrin. When present, the cyclodextrin derivative may be present in an amount of at least about 1.5 w/v %, at least about 3.0 w/v %, at least about 3.5 w/v % or at least about 4.5 w/v, but no greater than about 10.0 w/v %, no greater than about 8.0% w/v, no greater than about 6.5 w/v %, or no greater than about 5.5 w/v. In particular embodiments, the formulation includes about 5% w/v of either hydroxypropyl β-cyclodextrin or sulfoalkylether β-cyclodextrin.

In some embodiments, the formulations of the invention may include an additional therapeutic agent in addition to compound (I). Further therapeutic agents may include, for instance, other compounds and antibodies useful for treating ocular surface disorders. A non-limiting list of such agents incudes nonsteroidal anti-inflammatory drugs such as ketorolac, nepafenac, bromfenac, corticosteroids; drugs for dry eye disease such as cyclosprine, lifitegrast, or other TRPV1 inhibitors. In particular embodiments, the additional therapeutic agent is an ophthalmic steroid such as dexamethasone, fluocinolone, loteprednol, difluprednate, fluorometholone, prednisolone, prednisone, medrysone, triamcinolone, betamethasone, rimexolone, or pharmaceutically acceptable salts thereof. Further non-limiting examples of such additional therapeutic agents that may be included in the pharmaceutical composition include Xiidra® (lifitegrast), Restasis® (cyclosporine), minocycline, doxycycline, or other tetracycline antibiotics. Other examples include keratolytic agents such as selenium disulfide, salicylic acid, glycolic acid etc., or pharmaceutically acceptable salts thereof.

In some embodiments, the formulation is stored at refrigerated temperatures (e.g., 4° C.). In some embodiments, the formulation is warmed to room temperature prior to administration.

In some embodiments, the suspension is packaged in a single dose container. In some embodiments, the formulation is packaged in a multi-dose container.

The formulations described herein are delivered to the surface of the eye one to six times a day, depending on the routine discretion of the skilled clinician. In some embodiments, the formulations are administered, one, two, three, or four times a day.

In some embodiments, the formulation exhibits settling of less than about 10% after storage at room temperature for six months. In some embodiments, the formulation exhibits settling of less than about 8%, less than about 7%, less than about 6%, less than about 5%, less than about 4%, less than about 3%, or less than about 2% after storage at room temperature for six months. Settling behavior is measured by methods commonly known to those of skill in the art, for example as described herein.

In some embodiments, the amount of compound I in the formulation is at least 90% of the initial amount after about 6 months of storage under refrigeration (e.g., about 4° C.). In some embodiments, the amount of compound I in the formulation is at least about 90% of the initial amount after about 8 months, about 10 months, about 12 months, about 15 months, or about 18 months of storage under refrigeration. In some embodiments, the amount of compound I in the formulation is at least about 91%, at least about 92%, at least about 93%, at least about 94%, at least about 95%, at least 96%, at least about 97% or at least about 98% of the initial amount after about 6 months of storage under refrigeration (e.g., about 4° C.). In some embodiments, the amount of compound I in the formulation at least about 91%, at least about 92%, at least about 93%, at least about 94%, at least about 95%, at least 96%, at least about 97% or at least about 98% of the initial amount after about 18 months of storage under refrigeration. The amount of compound I in the formulation is measured using methods commonly known to those of skill in the art, for example, HPLC, LC/MS, etc.

In some embodiments, the formulation comprises no more than about 10% of a degradation product after 6 months under refrigeration, wherein the degradation product has a relative retention time of 1.23, compared to compound I, when analyzed by HPMC using a gradient 0.1% trifluoroacetic acid (TFA) water/acetonitrile mobile phase. In some embodiments, the formulation comprises no more than about 9%, no more than about 8%, no more than about 7%, no more than about 6%, no more than about 5%, no more than about 4%, no more than about 3%, or no more than about 2% of a degradation product after 6 months under refrigeration.

In some embodiments, no more than about 10% of compound I in the formulation degrades upon storage for 12 weeks at 40° C. In particular embodiments, no more than about 9%, no more than about 8%, no more than about 7%, no more than about 6%, no more than about 6%, no more than about 5%, no more than about 4%, no more than about 3%, no more than about 2% of compound I in the formulation degrades upon storage for 12 weeks at 40° C.

In some embodiments, the pharmaceutical formulations of the invention may include an additional therapeutic agent in addition to Compound (I). Further therapeutic agents may include, for instance, other compounds and antibodies useful for treating ocular surface disorders. A non-limiting list of such agents incudes nonsteroidal anti-inflammatory drugs such as ketorolac, nepafenac, bromfenac, corticosteroids; drugs for dry eye disease such as cyclosporine, lifitegrast, autologous serum, or other TRPV1 inhibitors. In particular embodiments, the additional therapeutic agent is an ophthalmic steroid such as dexamethasone, fluocinolone, loteprednol, difluprednate, fluorometholone, prednisolone, prednisone, medrysone, triamcinolone, betamethasone, rimexolone, or pharmaceutically acceptable salts thereof. Further non-limiting examples of such additional therapeutic agents that may be included in the pharmaceutical composition include Xiidra® (lifitegrast), Restasis® (cyclosporine), minocycline, doxycycline, or other tetracycline antibiotics. Other examples include keratolytic agents such as selenium disulfide, salicylic acid, glycolic acid etc., or pharmaceutically acceptable salts thereof.

Methods of Making

In some embodiments, the present invention is a method of making the pharmaceutical formulations of compound I.

In some embodiments, the formulation is prepared by mixing an amount of 4-(7-hydroxy-2-isopropyl-4-oxo-4H-quinazolin-3-yl)-benzonitrile (compound I) or a salt, co-crystal, or polymorph thereof, and one or more excipients selected from the group consisting of a surfactant, a suspending agent, a tonicity agent, a buffer, a preservative, a salt, and a preservative.

In some embodiments, the formulation is prepared by mixing an amount of 4-(7-Hydroxy-2-isopropyl-4-oxo-4H-quinazolin-3-yl)-benzonitrile (compound I) or a salt, co-crystal, or polymorph thereof,
    a non-ionic surfactant;
    a suspending agent;
    a tonicity agent;
    a buffer;
    a salt;
    optionally, a preservative; and
    water qs to 100%, and
    adjusting the pH to a range of from about 5.5 to about 8.0.

In some embodiments, the compound I is added as a stock suspension in water, optionally with the surfactant. In some embodiments, the compound I is present in an amount of 10% in the stock suspension. In alternative or additional embodiments, the stock suspension of compound I further includes 0.2% tyloxapol. In some embodiments, the stock suspension of compound I is milled to achieve a desired particle size of compound I. In some embodiments, the $D_{90}$ of compound I in the formulation (diameter at which 90% of compound I is comprised of smaller particles) is below about 10 μm, below about 8 μm, below about 6 μm, below about 4 μm, below about 3 μm, or about 2 μm. In some embodiments, the $D_{50}$ of compound I in the formulation (diameter at which 50% of compound I is comprised of smaller particles) is below about 10 μm, below about 8 μm, below about 6 μm, below about 4 μm, below about 3 μm, below about 2 μm, or about 1 μm. In some embodiments, the $D_{10}$ of compound I in the formulation (diameter at which 10% of compound I is comprised of smaller particles) is below about 5 μm, below about 4 μm, below about 3 μm, below about 2 μm, below about 1 μm, or about 0.3 μm.

In some embodiments, a 10% w/v slurry of compound I is jar milled on a roller mill at about 60 rpm for about 2 hours or about 3 hours.

In particular embodiments, the non-ionic surfactant, the suspending agent, the tonicity agent, buffer, and salt are as noted supra. In some embodiments, the formulation does not include a preservative.

An exemplary method of manufacture of a 1.5% w/v compound I suspension is described below:
1. Tare a clean, dry glass Schott bottle with a polybutylene terephthalate, PTFE-lined cap and a magnetic stir bar.
2. Add the batch quantity of compound I vehicle (including suspending agent, tonicity agent, surfactant, and salt, and pH adjusted to final pH) to the bottle. Seal and steam sterilize the compounding vessel ($F_0 \geq 30$).
3. Transfer the vessel to a horizontal laminar flow workbench and allow to cool.
4. Aseptically weigh and add the batch quantity of sterile 10% compound I/0.2% surfactant to the compounding vessel. Adjust to final batch weight, if necessary, with sterile (either steam sterilized or aseptically filtered) Purified Water qs and stir until uniform.
5. Aseptically fill the 1.5% suspension into sterile dispensing bottles. Insert suspension tips and tighten screw-on closures to seat tips and seal.
6. Remove filled units from laminar flow workbench and label. Measure the final pH and osmolality values.

Methods of Use

Without being bound by theory, it is hypothesized that blockers of the Transient Receptor Potential Vanilloid 1 (TRPV1) receptor may be useful in the treatment of pain, e.g., chronic pain.

Accordingly, in some embodiments, the invention provides a method of treating ocular surface pain in a subject in need thereof, said method includes administering to the subject an effective amount of compound (I), or a pharmaceutically acceptable salt, solvate, or co-crystal thereof. In some embodiments, the invention provides a method of reducing ocular surface pain in a subject in need thereof, said method includes administering to the subject an effective amount of compound (I), or a pharmaceutically acceptable salt, solvate, or co-crystal thereof. In some embodiments, the invention provides for the use of the compound of formula I, or a pharmaceutically acceptable salt, solvate, or co-crystal thereof, in the treatment of ocular surface pain. In some embodiments, the compound of formula I is in polymorphic form B. In particular embodiments, the methods described herein are carried out by administering the formulations of compound I described supra. Thus, the invention provides a method of treating ocular surface pain by administering a formulation of compound I as described herein. In particular embodiments, the method is the administration of a formulation that includes compound I as polymorph B.

In some embodiments, the subject suffers from episodic or acute ocular pain. In some embodiments, the subject suffers from chronic ocular surface pain, which lasts for at least three months. In some embodiments, the subject suffers from chronic ocular surface pain, which lasts for at least two months. In some embodiments, the subject suffers from chronic ocular surface pain, which lasts for at least one month. In some embodiments, the subject suffers from chronic ocular surface pain, which lasts for at least four months. In some embodiments, the subject suffers from chronic ocular surface pain, which lasts for at least five months. Thus, in some embodiments, the invention provides a method of treating chronic ocular surface pain in a subject by administering to the subject an effective amount of compound of formula I, or a salt, solvate, polymorph, or co-crystal thereof. In some embodiments, the invention provides a method of reducing chronic ocular surface pain in a subject by administering to the subject an effective amount of compound of formula I, or a salt, solvate, polymorph, or co-crystal thereof. The invention provides for the use of the compound of formula I, or a pharmaceutically acceptable salt, solvate, polymorph, or co-crystal thereof, in the treatment of chronic ocular surface pain. In some embodiments, the compound of formula I is in a formulation as described herein. In particular embodiments, the method is the administration of a formulation that includes compound I as polymorph B.

In some embodiments, the formulation is administered to the ocular surface of the subject, e.g., any part of the cornea, conjunctiva, or to the cul de sac of the eye.

In some embodiments, the invention provides for the administration of the compound of formula I to a subject in need thereof in a ophthalmically compatible formulation at a concentration of about 0.5% w/v to about 3.5% w/v. In some embodiments, concentrations for administration range from about 0.5% to about 3.5% w/v, about 0.5% to about 2.5% w/v, about 0.5% to about 1.5% w/v, about 0.5% to about 3.0% w/v, about 1.0% to about 2.5% w/v, about 1.5% to about 3.0% w/v, about 0.5% to about 2.5% w/v. In some embodiments, the concentration of the compound I in an ophthalmically compatible formulation is at least about 0.5% w/v, at least about 1.0% w/v, at least about 1.5% w/v, at least about 2.0% w/v, or at least about 2.5% w/v. In some embodiments, the concentration of the compound of formula I in a formulation for topical use is no more than about 5.0% w/v, no more than about 4.5% w/v, no more than about 4.0% w/v, no more than about 3.5% w/v, or no more than about 3.0% w/v. In particular embodiments, the concentration of the compound of formula I in a formulation for topical use is about 0.5% w/v, about 1.0% w/v, about 1.5% w/v, about 2.0% w/v, about 2.5% w/v, about 3.0% w/v, or about 3.5% w/v. In some embodiments, the dose per administration per eye is from about 0.15 to about 1.15 mg, or about 0.15 mg, 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1.0 mg, about 1.05 mg, about 1.1 mg, or about 1.15 mg. In some embodiments, the dose per administration per eye is about 0.18 mg, about 0.37 mg, about 0.55 mg, about 0.74 mg, or about 0.92 mg. In some embodiments, the total daily dose per eye is about 0.5 to about 3.5 mg, or about 0.5 mg, about 1.0 mg, about 1.5 mg, about 2.0 mg, about 2.5 mg, about 3.0 mg, or about 3.5 mg. In some embodiments, the compound of formula I is administered to the subject one to six times a day, e.g., one, two, three, or four times a day. In some embodiments, the compound of formula I is administered to the subject for a period of at least about one month, at least about two months, or at least about three months. In some embodiments, the compound of formula I is administered to the subject for a period of at least about 12 weeks.

In some embodiments, the ocular surface pain or the chronic ocular surface pain is associated with one or more of dry eye disease, Sjogren's Syndrome, conjunctivitis (including keratoconjunctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis.

In particular embodiments, the ocular surface pain or the chronic ocular surface pain is associated with dry eye disease or Sjogren's Syndrome. In some embodiments of the methods described herein, the subject suffers from ocular pain persisting for at least three months after photorefractive keratectomy (PRK) surgery or laser-assisted in situ keratomileusis (LASIK) surgery.

In some embodiments, the subject suffers from conjunctivitis, subconjunctival hemorrhage, subconjunctival scarring, conjunctival membranes, conjunctival ulceration, superficial punctate epithelial erosions, epithelial defects, lid margin ulceration, lid margin keratinization, symblepharon, ankyloblepharon, trichiasis, anterior blepharitis, punctal auto-occlusion, meibomian gland disease, corneal opacification, dry eye, districhiasis, limbal stem cell failure, or corneal vascularization.

In some embodiments, the administration of compound of formula I results in a reduction in the subject's ocular pain, compared to a placebo. In some embodiments, the reduction in the subject's ocular pain is at least about 3 when measured on a VAS score, compared to a placebo. In some embodiments, the administration results in a reduction in the subject's ocular pain of at least about 4, at least about 5, at least about 6, at least about 7, at least about 8, at least about 9, or at least about 10, when measured on the VAS score, compared to a placebo. In some embodiments, the administration results in a reduction in the subject's pain of at least about 10%, at least about 15%, at least about 20%, or at least about 25%, compared to a placebo, about one hour, about 2 hours, or about 2-4 hours after the administration. In some embodiments, the administration results in a reduction in the subject's pain, when measured after 7 days of administration of the compound of formula I. In some embodiments, the administration results in a reduction in the subject's pain, when measured after 14 days of administration of the compound of formula I.

In some embodiments, the administration of the compound of formula I results in a reduction in the subject's pain of at least about 2 compared to a placebo, as measured by the VAS score, about half hour after the administration.

In some embodiments, the reduction in pain score arises from the difference in pain scores prior to and after administration of compound I to the subject. In some embodiments, the reduction in pain score as measured by the VAS, arises from the difference in VAS scores prior to and after administration of compound I to the subject. In some embodiments, the reduction in VAS score occurs within about half hour after administration of compound I to the subject. In some embodiments, the reduction in pain score occurs within about 1 hour, about 2 hours, about 3 hours, about 4 hours, about 5 hours, or about 6 hours after administration of compound I to the subject. In some embodiments, the administration results in a reduction in the subject's pain, when measured after 7 days of administration of the compound of formula I. In some embodiments, the administration results in a reduction in the subject's pain, when measured after 14 days of administration of the compound of formula I.

In some embodiments, the administration of the compound of formula I results in an improved score on at least one question of the OPAS of at least about 10%, at least about 20%, or at least about 30%.

In some embodiments, the administration of the compound of formula I results in an improved score on at least one question of the Visual Tasking Questionnaire of at least about 10%, at least about 20%, or at least about 30%.

In some embodiments, the administration of the compound of formula I results in reduced ocular hyperemia (redness of the eye), compared to placebo. In particular embodiments, the administration of the compound of formula I results in reduced grade 1, grade 2, grade 3, or grade 4 hyperemia compared to placebo. In some embodiments, the administration results in a reduction in ocular hyperemia score of at least about 1, at least about 2, at least about 3, at least about 4, or at least about 5, on the McMonnies scale.

Thus, in some embodiments, the present invention relates to a method of treating or reducing ocular hyperemia in a subject in need thereof, comprising administering to the subject an effective amount of compound of formula I, or a salt, solvate, polymorph, or co-crystal thereof. In some embodiments, the administration of compound I results in a reduction in ocular hyperemia of at least 1, at least 2, at least 3, at least 4, or at least 5 on the McMonnies scale. In some embodiments, the invention provides for the use of the compound of formula I, or a pharmaceutically acceptable salt, solvate, or co-crystal thereof, in the treatment or reduction of ocular hyperemia. In some embodiments, the invention provides for the administration of the compound of formula I to a subject in need thereof in a ophthalmically compatible formulation at a concentration of about 0.5% w/v to about 3.5% w/v. In some embodiments, concentrations for administration range from about 0.5% to about 3.5% w/v, about 0.5% to about 2.5% w/v, about 0.5% to about 1.5% w/v, about 0.5% to about 3.0% w/v, about 1.0% to about 2.5% w/v, about 1.5% to about 3.0% w/v, about 0.5% to about 2.5% w/v. In particular embodiments, the concentration of the compound of formula I in a formulation for topical use is about 0.5% w/v, about 1.0% w/v, about 1.5% w/v, about 2.0% w/v, about 2.5% w/v, about 3.0% w/v, or about 3.5% w/v. In some embodiments, the dose per administration per eye is from about 0.15 to about 1.15 mg, or about 0.15 mg, 0.2 mg, about 0.25 mg, 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1.0 mg, about 1.05 mg, about 1.1 mg, or about 1.15 mg. In some embodiments, the dose per administration per eye is about 0.18 mg, about 0.37 mg, about 0.55 mg, about 0.74 mg, or about 0.92 mg. In some embodiments, the total daily dose per eye is about 0.5 to about 3.5 mg, or about 0.5 mg, about 1.0 mg, about 1.5 mg, about 2.0 mg, about 2.5 mg, about 3.0 mg, or about 3.5 mg. In some embodiments, the compound of formula I is administered to the subject one to six times a day, e.g., one, two, three, or four times a day. In some embodiments, the compound of formula I is administered to the subject for a period of at least about one month, at least about two months, or at least about three months. In particular embodiments, the compound of formula I is administered in a formulation described herein.

In some embodiments, the ocular hyperemia is associated with one or more of dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In particular embodiments, the ocular hyperemia is associated with dry eye disease. In some embodiments of the methods described herein, the ocular hyperemia persists for at least three months after photorefractive keratectomy (PRK) surgery or laser-assisted in situ keratomileusis (LASIK) surgery.

In some embodiments, the ocular surface pain or chronic ocular surface pain is associated with dry eye disease. In some embodiments, the administration of the compound of formula I results in a a decrease in the symptoms of dry eye disease. Dry eye disease is generally understood to be a complex, multifactorial condition characterized by inflammation of the ocular surface and lacrimal glands and reductions in the quality and/or quantity of tears. It is believed that up to 30% of dry eye disease patients suffer from ocular surface pain that may be chronic, i.e., lasting at least 12 weeks or three months. Thus, in some embodiments, the invention results in a decrease of at least about 10% in the symptoms of dry eye disease, including one or more of ocular dryness, ocular discomfort, ocular hyperemia, ocular burning or stinging, grittiness or foreign body sensation, or photophobia.

In some embodiments, the invention relates to a method of treating dry eye disease in a subject in need thereof, comprising administering to the subject an effective amount of compound of formula I, or a salt, solvate, polymorph, or co-crystal thereof. In some embodiments, the invention relates to a method of treating dry eye disease in a subject in need thereof, comprising administering to the subject an effective amount of compound of formula I, or a salt, solvate, polymorph, or co-crystal thereof, wherein the compound of formula I is safe for administration over a period of at least 2 months, at least 3 months, at least 4 months, or at least 5 months. In particular embodiments, the invention provides for the use of the compound of formula I, or a pharmaceutically acceptable salt, solvate, or co-crystal thereof, in the treatment of dry eye disease. In some embodiments, the invention results in a decrease of at least about 10%, at least about 15%, at least about 20%, or at least about 30% in the symptoms of dry eye disease, including one or more of ocular dryness, ocular discomfort, ocular hyperemia, ocular burning or stinging, grittiness or foreign body sensation, or photophobia. In some embodiments, the invention provides for the administration of the compound of formula I to a subject in need thereof in a ophthalmically compatible formulation at a concentration of about 0.5% w/v to about 3.5% w/v. In some embodiments, concentrations for administration range from about 0.5% to about 3.5% w/v, about 0.5% to about 2.5% w/v, about 0.5% to about 1.5% w/v, about 0.5% to about 3.0% w/v, about 1.0% to about 2.5% w/v, about 1.5% to about 3.0% w/v, about 0.5% to about 2.5% w/v. In particular embodiments, the concentration of the compound of formula I in a formulation for topical use is about 0.5% w/v, about 1.0% w/v, about 1.5% w/v, about 2.0% w/v, about 2.5% w/v, about 3.0% w/v, or about 3.5% w/v. In some embodiments, the dose per administration per eye is from about 0.15 to about 1.15 mg, or about 0.15 mg, 0.2 mg, about 0.25 mg, 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1.0 mg, about 1.05 mg, about 1.1 mg, or about 1.15 mg. In some embodiments, the dose per administration per eye is about 0.18 mg, about 0.37 mg, about 0.55 mg, about 0.74 mg, or about 0.92 mg. In some embodiments, the total daily dose per eye is about 0.5 to about 3.5 mg, or about 0.5 mg, about 1.0 mg, about 1.5 mg, about 2.0 mg, about 2.5 mg, about 3.0 mg, or about 3.5 mg. In some embodiments, the compound of formula I is administered to the subject one to six times a day, e.g., one, two, three, or four times a day. In some embodiments, the compound of formula I is administered to the subject for a period of at least about one month, at least about two months, or at least about three months. In some embodiments, the compound of formula I is administered as a formulation described herein.

In some embodiments of the methods described herein, the administration of the compound of formula I does not result in a change (e.g., of less than 5% difference, less than 4% difference, or less than 3% difference) in one or more of best corrected visual acuity, slit-lamp biomicroscopy, dilated eye exam, blink rate, tear production, or intraocular pressure compared to a placebo. In some embodiments of the methods described herein, the administration of compound of formula I does not result in a delay in wound healing compared to a placebo in a patient in need thereof. Patient Population In specific embodiments, a subject to be treated by methods provided herein suffers from an ocular surface disorder. Non-limiting examples of ocular surface disorders include chronic ocular surface pain (COSP), dry eye disease, Sjogren's Syndrome, conjunctivitis (including keratoconjuctivitis, vernal keratoconjunctivitis, allergic conjunctivitis), Map-Dot-Fingerprint Dystrophy, acanthamoeba, fibromyalgia, Meibomian gland dysfunction, thyroid eye disease, rosacea, ptosis, keratoconus, ocular pain syndrome, Steven-Johnson's syndrome, corneal epitheliopathies, corneal neuropathies (including LASIK induced corneal neuropathies), corneal dystrophies (including recurrent corneal dystrophies), epithelial basement membrane dystrophy, corneal erosions or abrasions (including recurrent corneal erosions or abrasions), ocular surface diseases, blepharitis, graft vs host disease, meibomitis, glaucoma, conjunctivochalasis, keratopathis (including herpetic keratopathy, filamentary keratopathy, band or bullous keratopathy, exposure keratopathy), keratitis (including herpes simplex virus keratitis), iritis, episclentis, corneal surgery, multiple sclerosis, trichiasis, pterygium, neuralgia, xerophthalmia, or patients recovering from neurotrophic keratitis. In some embodiments, the subject suffers from ocular pain persisting for at least three months after photorefractive keratectomy (PRK) surgery or laser-assisted in situ keratomileusis (LASIK) surgery.

In certain embodiments, methods provided herein is for treating, or reducing, ocular surface pain, such as acute ocular surface pain.

In certain embodiments, methods provided herein is for treating, or reducing, ocular surface pain, such as chronic ocular surface pain (COSP). In particular aspects, COSP is characterized as persistent ocular surface pain (e.g., persistent severe ocular surface pain) that can distract from, or can interfere with, regular daily activities. In specific aspects, COSP can result in poor quality of life, and can persist for at least 1 month, at least 2 months, at least 3 months, at least 4 months, at least 5 months, or at least 6 months. In some aspects, COSP can persist for at least about 2 months or at least about 3 months. In other aspects, COSP can persist for at least 3 months or at least 4 months. In particular aspects, subject with COSP remain symptomatic despite adherence to other therapies indicated for their underlying disease (e.g., an ocular surface disorder such as dry eye disease or Sjogren's Syndrome).

In some embodiments, the subject to be treated suffers from ocular neuropathic pain (ONP). ONP is a spectrum of disorders of ocular pain that may be caused by damage or disease affecting the nerves, e.g., corneal nerves. Symptoms of ONP may include one or more of eye pain, sensitivity to light, hyperalgesia or dysesthesia (abnormal sensations) such as a sensation of dryness, stinging, or foreign body, pain from normally non-painful stimuli (allodynia). Gabapentin and other neuropathic pain medications may be used to blunt sensory nerve stimulation or the perception of nerve stimulation.

In some embodiments, the subject to be treated suffers from exposure keratopathy. EK is damage to the cornea that occurs primarily from prolonged exposure of the ocular surface to the outside environment. EK can lead to ulceration, microbial keratitis, and permanent vision loss from scarring. Patients at risk for EK include those who suffer from conditions that interfere with the ability to protect the cornea; either by incomplete eyelid closure (e.g., lagophthalmos, proptosis, lid malposition), inadequate blink reflex, inadequate blink rate (for example, caused by a neurologic disease, e.g., Parkinson disease, a neuromuscular disease) and/or decreased protective lubrication of the cornea. Symptoms of EK include foreign body sensation, burning, increased tearing, and intermittent blurry vision (from an unstable tear film), pain and photophobia. Standard treatments include the use of frequent artificial tears with nightly lubricating ointment, punctal plugs.

In some embodiments, the subject to be treated suffers from keratoconjuctivitis. Keratoconjuctivitis is an inflammatory process that involves both the conjunctiva and the cornea. Superficial inflammation of the cornea (keratitis) occurs commonly in association with viral and bacterial conjunctivitis, for example in adults. The following types of keratoconjuctivitis are distinguished based on the potential cause of inflammation:

Keratoconjunctivitis sicca is cause by the inflammation due to dryness;
Vernal keratoconjunctivitis (VKC) occurres seasonally, considered to be due to allergens;
Atopic keratoconjunctivitis is one manifestation of atopy;
Epidemic keratoconjunctivitis or adenoviral keratoconjunctivitis is caused by an adenovirus infection;
Infectious bovine keratoconjunctivitis (IBK) is a disease affecting cattle caused by the bacteria *Moraxella bovis;*
Pink eye in sheep and goat is mostly caused by *Chlamydophila pecorum;*
Superior limbic keratoconjunctivitis is thought to be caused by mechanical trauma;
Keratoconjunctivitis photoelectrica (arc eye) means inflammation caused by photoelectric UV light.

In some embodiments, the subject to be treated suffers from dry eye. The term "dry eye" as used herein, refers to inadequate tear production and/or abnormal tear composition. Dry eye syndrome disease (DEDS), also known as dry eye syndrome, keratoconjunctivitis sicca or keratitis sicca, or tear dysfunction syndrome, or burning eye syndrome results from deficiency of any of the tear film layers. Dry eye is a multifactorial disease of the tears and ocular surface that results in symptoms of discomfort, visual disturbance, and tear—film instability with potential damage to the ocular surfaceocular surface characterized by loss of homeostasis of the tear film, and accompanied by ocular symptoms, in which tear film instability and hyperosmolarity, ocular surface inflammatoin and damage, and neuro-sensory abnormalities play etiological roles (Craig J P, et al., *The Ocular Surface* 2017; 15:276-83). It may be accompanied by increased osmolarity of the tear film and inflammation of the ocular surface. Dry eye disorder may range from mild to moderate to severe forms. Symptoms of dry eye syndrome disease include gritty, foreign body sensations, burning, photophobia, and decreased visual acuity, tearing, stinging, itching, sandy or gritty feeling, discharge, frequent blinking, mattering or caking of the eyelashes (usually worse upon waking), redness, blurry or fluctuating vision (made worse when reading, computer, watching television, driving, or playing video games), light-sensitivity, eye pain and/or headache, heavy eye lids, eye fatigue. Causes of dry eye disease include, but are not limited to, the following: idiopathic, congenital alacrima, xerophthalmia, lacrimal gland ablation, and sensory denervation; collagen vascular diseases, including rheumatoid arthritis, Wegener's granulomatosis, and systemic lupus erythematosus; Sjogren's Syndrome and autoimmune diseases associated with Sjogren's syndrome; abnormalities of the lipid tear layer caused by blepharitis or rosacea; abnormalities of the mucin tear layer caused by vitamin A deficiency; trachoma, diphtheric keratoconjunctivitis; mucocutaneous disorders; aging; menopause; and diabetes. Dry eye signs and/or symptoms as defined herein may also be provoked by other circumstances, including but not limited to the following: prolonged visual tasking; working on a computer; being in a dry environment; warm or cold wind or air flow; seasonal changes; ocular irritation; contact lenses, LASIK and other refractive surgeries; fatigue; and medications such as isotretinoin, sedatives, diuretics, tricyclic antidepressants, antihypertensives, oral contraceptives, antihistamines, nasal decongestants, beta-blockers, phenothiazines, atropine, and pain relieving opiates such as morphine.

Diagnostic testing for dry eye includes evaluation of cornea sensation (corneal hyperesthesia and/or reduced sensation may be present in severe and chronic dry eye disease) using, for example, a cotton tip applicator or more precisely with a Cochet-Bonnet esthesiometer; measuring tear break up time using, for example, a fluorescein-impregnated strip wet with non-preserved saline solution or more objective computerized methods without the need for fluorescein instillation; performing ocular surface staining, e.g., fluorescein sodium, rose bengal, lissamine green; performing Schirmer test (relatively insensitive for patients with mild dry eye), testing delayed tear clearance; tear meniscus height; measuring level of MMP-9 (MMP-9 has been shown to be elevated in the tears of patient with dry eye disease, and levels correlate with examination findings in patients with moderate to severe dry eye); measuring tear osmolarity and tear film interferometry; performing Sjo test (detection of SS-A (anti-Ro) and SS-B (anti-La) autoantibodies in serum, salivary gland protein 1 (SP-1), carbonic anhydrase 6 (CA6), and parotid secretory protein (PSP). SP-1, CA6, and PSP).

Artificial tears, lubricating ointments, corticosteroids (e.g., loteprednol 0.5% eyedrops four times a day) are used as an initial treatment. Prescription medicines include cyclosporine, lifitegrast, diquafosol, rebamepide, corticosteroids (e.g., loteprednol 0.5% eyedrops four times a day).

The term "tear film dysfunction" refers to a state when the tear film breaks down in different places on the cornea and conjunctiva, leading not only to symptoms of irritation, but also to unstable and intermittently changing vision. For example, dry eye syndrome disease is characterized by tear film dysfunction. The symptoms of tear film dysfunction include tearing, burning, stinging, itching, sandy or gritty feeling, scratchy or foreign-body sensation, discharge, frequent blinking, mattering or caking of the eyelashes (usually worse upon waking), redness, blurry or fluctuating vision (made worse when reading, computer, watching television, driving, or playing video games), light-sensitivity, eye pain and/or headache, heavy eye lids, eye fatigue.

Adenoviral keratoconjunctivitis, also known as Keratoconjunctivitis epidemica is a common and highly contagious viral infection of the eye. The clinical course of Adenoviral keratoconjunctivitis is divided into an acute phase with conjunctival inflammation of varying intensity with or without corneal involvement and a chronic phase with corneal opacities.

Vernal keratoconjunctivitis (VKC) is an atopic condition of the external ocular surface characterized by symptoms consisting of severe itching, photophobia, foreign body sensation, mucous discharge (often described as "ropy"), blepharospasm, and blurring of vision (Buckley, R. J., *Int Ophthalmol Clin,* 1988 28(4): p. 303-8; Kumar, S., *Acta Ophthalmologica,* 2009. 87(2): p. 133-147). It is typically bilateral but may be asymmetric in nature. It characteristically affects young males in hot dry climates in a seasonal manner; in 23% of patients may have a perennial form (Kumar, S., *Acta Ophthalmologica,* 2009. 87(2): p. 133-147; Bonini, S., et al., *Ophthalmology,* 2000. 107(6): p. 1157-63).

The signs of VKC can be divided into conjunctival, limbal and corneal signs:
- Conjunctival signs include diffuse conjunctival injection and upper tarsal giant papillae that are discrete>1 mm in diameter;
- Limbal signs include thickening and opacification of the limbal conjunctiva as well as gelatinous appearing and sometime confluent limbal papillae. Peri-limbal Horner-Trantas dots are focal white limbal dots consisting of degenerated epithelial cells and eosinophils (Buckley, R. J., *Int Ophthalmol Clin,* 1988. 28(4): p. 303-8);
- Corneal signs vary according to the severity of the disease process and include macro-erosions, corral ulcers and scars (Buckley, R. J., *Int Ophthalmol Clin,* 1988. 28(4): p. 303-8).

Active VKC patients (defined as moderate to severe ocular discomfort including photophobia, papillae on the upper tarsal conjunctiva, or limbal Horner-Trantas dots clearly recognizable at the time of the examination) showed significantly increased symptoms and signs of ocular surface disease. Inactive VKC patients (defined as no symptoms or mild discomfort, and absence of corneal abnormalities at the time of the examination) showed increased photophobia, conjunctival lissamine green staining and Schirmer test values, and reduced fluorescein break-up time (BUT) and corneal sensitivity. This syndrome seems to affect the ocular surface in all phases (active and quiescent), determining abnormalities in tear film stability, epithelial cells integrity, and corneal nerves function (Villani E. et al., *Medicine* (Baltimore). 2015 October; 94(42): e1648).

The following factors are thought to play a role in VKC: IgE mediate reaction via mast cell release; activated eosinophils, mononuclear cells and neutrophils as well as the CD4 T-helper-2 driven type IV hypersensitivity with immunomodulators such as IL-4, IL-5, and bFGF (Buckley, R. J., *Int Ophthalmol Clin,* 1988. 28(4): p. 303-8; Kumar, S., *Acta Ophthalmologica,* 2009. 87(2): p. 133-147; La Rosa, M., et al, *Ital J Pediatr,* 2013. 39: p. 18).

Treatment consists of cool compresses and lid scrubs, saline eyedrops, which may help to relieve symptoms, along with topical antihistamines, nonsteroidal anti-inflammatory drugs or corticosteroids, e.g., low-absorptions corticosteroids (fluoromethelone, loteprednol, remexolone, etc.), opical mast cell stabilizers (cromolyn sodium, nedocromil sodium, and lodoxamide), topical cyclosporin-A, or tacrolimus. See e.g., Oray, M. and E. Toker, *Cornea,* 2013. 32(8): p. 1149-54: Vichyanond, P. and P. Kosrirukvongs, *Curr Allergy Asthma Rep,* 2013. 13(3): p. 308-14; Barot, R K et al., *J Clin Diagn Res.* 2016 June; 10(6):NC05-9; Wan Q et al., *Ophthalmic Res.* 2018; 59(3):126-134.

Atopic keratoconjunctivitis (AKC) typically has an older age of onset in the 2nd to 5th decade, as opposed to onset prior to age 10 with VKC. Conjunctival involvement is classically on the upper tarsus in VKC and on the lower tarsus in AKC. AKC is typically more chronic in nature and more commonly results in scarring of the cornea and conjunctival cicatrization.

Sjogren's Syndrome (Sjogren's syndrome associated with dry eye) is a chronic inflammatory disorder characterized by exocrine gland dysfunction including the salivary and lacrimal glands that in many cases results in a severe dry eye. Primary symptoms are dry eyes (keratitis sicca or keratoconjunctivitis sicca) and dry mouth (xerostomia). Severe dry eyes can cause corneal pain, corneal scarring, ulceration, infection, and even perforation. The differential diagnosis includes conditions such as adult blepharitis, dry eye disease, and juvenile idiopathic arthritis uveitis, as well keratopathies, e.g., superficial punctate, filamentary, neurotrophic, exposure). Treatment of Sjogren's syndrome is aimed at maintaining the integrity of the tear film through preservation, augmentation, and/or replacement of the deficient tear secretion. Treatment of Sjogren's syndrome thus includes artificial tears and lubricating ointments; autologous serum eyedrops; oral omega-6 essential fatty acids; fluid-ventilated, gas permeable scleral lenses; topical corticosteroids; punctal occlusion to decrease tear drainage; a small lateral tarsorrhaphy; humidification of the environment; hydrophilic bandage lenses; bromhexine and 3-isobutyl 1-methylxanthine (IBMX) (augmentation of tear production/secretion); agents to stimulate muscarinic receptors (pilocarpine and cevimeline); immunosuppressive agents, e.g., methotrexate, antimalarials, cyclophosphamide, leflunomide, or tumor necrosis factor (TNF), e.g., infliximab, a monoclonal antibody to TNF-alpha; Cyclosporin A; the bandage contact lens.

Steven-Johnson's syndrome (SJS) is a dermatologic emergency or a type of severe skin reaction characterized by the presence of epidermal and mucosal bullous lesions involving less than 10% of the total body surface area. Early symptoms of SJS include fever and flu-like symptoms, which may precede or occur concurrently with the development of a macular rash involving the trunk and face. As the disease progresses, the macular rash coalesces, the involved areas develop bullae, and the epidermal layer eventually sloughs off. During the acute phase of SJS-TEN, 80% of patients will have ocular involvement.

The constellation of high fever (>102.2), malaise, arthralgia, a macular rash involving the trunk, neck and face, and recent history of new medication exposure or recently increased dosage of an existing medication are indicators used for diagnosis of SJS. A skin biopsy of an effected area can be performed for a confirmation of the diagnosis. Granulysin can be used as a marker for the diagnosis of SJS. The concentration of granulysin within bullous fluid correlates with the severity of the acute phase of SJS (Chung W H, et al. *Nat Med.* 2008; 14(12):1343-50).

Ocular manifestations in SJS include conjunctivitis, subconjunctival hemorrhage, subconjunctival scarring, conjunctival membranes, conjunctival ulceration, superficial punctate epithelial erosions, epithelial defects, lid margin ulceration, lid margin keratinization, symblepharon, ankyloblepharon, trichiasis, anterior blepharitis, punctal autoocclusion, meibomian gland disease, corneal opacification, dry eye, districhiasis, limbal stem cell failure, corneal vascularization. Eye treatment in SJS consists of saline eyedrops, preservative-free artificial tears and ointments to provide adequate lubrication and reduce epithelial injury. Patients with any corneal or conjunctival epithelial defects are treated with prophylactic topical antibiotics, preferably a fourth generation fluoroquinolone. Patients having mild or moderate ocular involvement (less than one-third lid margin involvement, conjunctival defects less than 1 cm at greatest diameter, and no corneal epithelial defects) are typically treated with topical moxifloxacin 0.5% four times a day, cyclosporine 0.05% twice daily, and topical steroids (prednisolone acetate 1% four to eight times a day or dexamethasone 0.1% twice daily). Patients having severe or extremely severe ocular involvement (greater than one-third lid margin involvement, conjunctival defects greater than 1 cm, and corneal epithelial defects) undergo an amniotic membrane (AM) grafting in addition to the treatments listed above.

In some embodiments, the subject to be treated suffers from corneal epithelipathy. Corneal epitheliopathy is a disease involving corneal epithelium, e.g., manifested in altered corneal epithelial barrier function.

In some embodiments, the subject to be treated suffers from corneal neuropathy or corneal neuralgia. Corneal neuropathy or corneal neuralgia is a disorder associated with corneal pain caused by the damaged nerve fibers in the cornea, the sensory fibers. One of the examples of corneal neuropathy is a LASIK induced corneal neuropathy. Corneal neuropathy generally could be identified and diagnosed through dry eye investigations. Though the causes and risk factors are unclear yet, patients with dry eye-like symptoms, increased corneal sensitivity and changes of corneal nerve morphology, but no signs of dryness may suffer from corneal neuropathy.

In some embodiments, the subject to be treated suffers from ocular surface disease or disorder. The term "ocular surface diseases" or "ocular surface disorders" encompasses disease entities as well as related symptoms that result from a variety of abnormalities, including abnormal lid anatomy or function, abnormal or altered tear production or composition, and related subclinical signs. Many diseases can cause ocular surface disorders. Patients with ocular surface disorders may exhibit clinical signs common to several diseases, and include chronic punctate keratopathy, filamentary keratopathy, recurrent corneal erosion, bacterial conjunctivitis, culture-negative conjunctivitis, cicatrising (scarring) conjunctivitis, persistent epithelial defect, infectious keratitis, corneal melt and ocular surface failure. The most common ocular surface disorders stem from tear-film abnormalities and/or lid-gland dysfunction ("blepharitis").

In some embodiments, the subject to be treated suffers from neurotrophic keratitis or neurotrophic keratopathy. Neurotrophic keratitis or neurotrophic keratopathy (NK) is a corneal degenerative disease characterized by a reduction or absence of corneal sensitivity. In NK, corneal innervation by trigeminal nerve is impaired. Since corneal sensory innervation is impaired in NK, patients do not commonly complain of ocular surface symptoms. However, blurred vision can be reported due to irregular epithelium or epithelial defects (PED), scarring, or edema. NK is usually graded in three different stages in accordance to the "Mackie classification". Stage II NK is defined by a recurrent or persistent epithelial defects, most commonly in the superior half of the cornea. One of the treatments that may be used in Stage II NK includes topical Nerve Growth Factor. Patients typically experience pain during treatment with NGF due to reforming of the nerves.

In some embodiments, the subject to be treated suffers from blepharitis. Blepharitis is an inflammatory condition of the eyelid margin, which can lead to permanent alterations in the eyelid margin or vision loss from superficial keratopathy, corneal neovascularization, and ulceration. According to anatomic location, blepharitis can be divided into anterior and posterior. Anterior blepharitis affects the eyelid skin, base of the eyelashes, and the eyelash follicles and includes the traditional classifications of staphylococcal and seborrheic blepharitis. Posterior blepharitis affects the meibomian glands and gland orifices, the primary cause being meibomian gland dysfunction. Symptoms of chronic blepharitis may include redness, burning sensation, irritation, tearing, eyelid crusting and sticking, and visual problems such as photophobia and blurred vision. Long-term management of symptoms may include daily eyelid cleansing routines and the use of therapeutic agents that reduce infection and inflammation. Treatment includes topical or systemic antibiotics e.g., bacitracin or erythromycin; oral antibiotics, e.g., tetracyclines (tetracycline, doxycycline, minocycline) or macrolides (erythromycin, azithromycin); topical steroids, e.g., corticosteroid, e.g., loteprednol etabonate, fluorometholone; topical combinations of an antibiotic and corticosteroid such as tobramycin/dexamethasone or tobramycin/loteprednol; topical cyclosporine 0.05%.

In some embodiments, the subject to be treated suffers from Meibomian gland dysfunction. The meibomian gland is a holocrine type of exocrine gland, at the rim of the eyelid inside the tarsal plate, responsible for the supply of meibum, an oily substance that prevents evaporation of the eye's tear film. Meibomian gland dysfunction (MGD), also known as meibomitis, posterior blepharitis or inflammation of the meibomian glands, is a chronic, diffuse abnormality of the meibomian glands, commonly characterized by terminal duct obstruction and/or qualitative/quantitative changes in the glandular secretion (Nelson J D, et al., *Invest Ophthalmol Vis Sci* 2011; 52:1930-7). It may result in alteration of the tear film, symptoms of eye irritation, clinically apparent inflammation, and ocular surface disease. MGD often causes dry eye, and may contribute to blepharitis. In some cases topical steroids and topical/oral antibiotics are also prescribed reduce inflammation. Intense pulsed light (IPL) treatments or other mechanical treatments that apply heat and pressure to express the glands (eg, LipiFlow) have also been shown to reduce inflammation and improve the gland function in patients.

In some embodiments, the subject to be treated suffers from graft-versus-host disease. Graft-versus-host disease (GVHD) is an inflammatory disease that is unique to allogeneic transplantation. It is an attack by transplanted leukocytes against the recipient's tissues that can occur even if the donor and recipient are HLA-identical. Acute graft-versus-host disease typically occurs in the first 3 months after transplantation and may involve the skin, intestine, or the liver. Corticosteroids such as prednisone are a standard treatment. Chronic graft-versus-host disease may also develop after allogeneic transplant and is the major source of late complications. In addition to inflammation, chronic graft-versus-host disease may lead to the development of fibrosis, or scar tissue, similar to scleroderma or other autoimmune diseases and may cause functional disability, and the need for prolonged immunosuppressive therapy.

In some embodiments, the subject to be treated suffers from ocular graft versus host disease. GVHD occurs in patients who have undergone allogenic hematological stem cell transplantation. It can occur in patients who have acute or chronic GVHD, though it is more common in patients with the chronic form. Approximately 40-90% of patients with chronic GVHD will develop ocular symptoms. Ocular manifestations can include moderate to severe keratoconjuncitvitis sicca, bilateral marginal keratitis, anterior uveitis, corneal ulceration or neovascularization. Treatment includes topical lubricants including preservative free artificial tears, autologous serum tears and other topical and systemic immunosuppressive treatments; systemic steroids; topical cyclosporine 0.5%.

EXAMPLES

The following examples are included to demonstrate non-limiting embodiments of the present invention. Those of skill in the art will appreciate that changes to the specific embodiments described herein can be made and still obtain a like result without departing from the spirit and scope of the invention.

Example 1. Solubility of Compound I

As noted above, compound I is sparingly soluble in various media. The solubility of compound I in various solvents is shown in Table 1.

TABLE 1

| Solubility of compound I in Solvents | |
|---|---|
| Solvent | Solubility |
| Water | 0.01 |
| Ethanol | 0.79 |
| Polyethylene Glycol 200 | 1.62 |
| Polyethylene Glycol 300 | 2.04 |
| Polyethylene Glycol 400 | 1.66 |
| Propylene Glycol | 1.68 |
| Isosorbide | 0.34 |
| Propylene Carbonate | 0.40 |
| Hexylene Glycol | 0.28 |
| Isopropanol | 0.33 |
| Isopropyl Myrisate | 0.09 |
| Diisopropyl Adipate | 0.16 |
| Oleyl Alcohol | 0.12 |
| Mineral Oil | 0.03 |
| Medium-Chain Triglycerides (Miglyol 812) | 0.10 |

Example 2. Exploratory Formulations for Stability Testing

Based on the limited solubility of compound I in various solvents and in water, a suspension formulation was explored for development. The following five formulations were prepared and tested for stability. Formulations were stored in crimp-sealed glass vials at room temperature and at 40° C. At 6, 8 and 12 weeks, samples were evaluated for compound I stability.

TABLE 2

| Compound I Formulations for Exploratory Stability | | | | | |
|---|---|---|---|---|---|
| | Percent w/w | | | | |
| Component | FID 121522 | FID 121511 | FID 121512 | FID 121513[a] | Lot 17307:087B |
| Compound I | 0.5 | 0.5 | 0.5 | 0.00135 | 0.5 |
| Tyloxapol | 0.1 | 0.1 | 0.1 | 0.1 | 0.1 |
| Poloxamer 407 | 17.5 | — | — | — | — |
| Hypromellose | — | 0.5 | 0.5 | — | — |
| Carbomer Homopolymer Type B | — | — | — | — | 0.4 |
| Polyethylene Glycol 6000 | 2 | — | — | — | — |
| Polyethylene Glycol 400 | — | — | 7 | 7 | — |
| Benzalkonium Chloride | 0.02 | 0.02 | 0.02 | 0.02 | 0.02 |
| Edetate Disodium | 0.02 | 0.02 | 0.02 | 0.02 | 0.02 |
| Boric Acid | 0.3 | 0.3 | 0.3 | 0.3 | 0.3 |
| Mannitol | 0.3 | 4.5 | 0.3 | 0.3 | 4.5 |
| Monobasic Sodium Phosphate monohydrate | 0.13 | 0.13 | 0.13 | 0.13 | 0.13 |
| Dibasic sodium phosphate anhydrous | 0.01 | 0.01 | 0.01 | 0.01 | 0.01 |
| Sodium Hydroxide | qs pH 6 | qs pH 6 | qs pH 6 | qs pH 6 | qs pH 6 |
| Hydrochloric Acid | qs pH 6 | qs pH 6 | qs pH 6 | qs pH 6 | qs pH 6 |
| Purified Water | qs 100 | qs 100 | qs 100 | qs 100 | qs 100 |

[a]FID 121513 is the filtered supernatant of FID 121512 and is a solution. The other four formulations in the table are suspensions.

The formulations prepared in Table 2 were assayed using an exploratory UPLC method developed for the assay of compound I as shown in Table 3.

TABLE 3

Exploratory Compound I UPLC Method

| | |
|---|---|
| Column | ACQUITY UPLC BEH Shield RP18, 1.7 μm, 2.1 × 100 mm |
| Column temperature | 65° C. UV detector wavelength 254 nm |
| Injection volume | 2 μL |
| Mobile phase A | 0.1% Formic Acid B Acetonitrile |

| Gradient | Tim (min) | Flow Rate (mL/min) | % A | % B | Curve |
|---|---|---|---|---|---|
| | 0 | 0.8 | 70 | 30 | |
| | 1.0 | 0.8 | 30 | 70 | 6 |
| | 1.5 | 0.8 | 20 | 80 | 6 |
| | 2 | 0.8 | 70 | 30 | 6 |

| | |
|---|---|
| Run time | 3 |
| Relative retention | 0.9 |

Figure 1B:
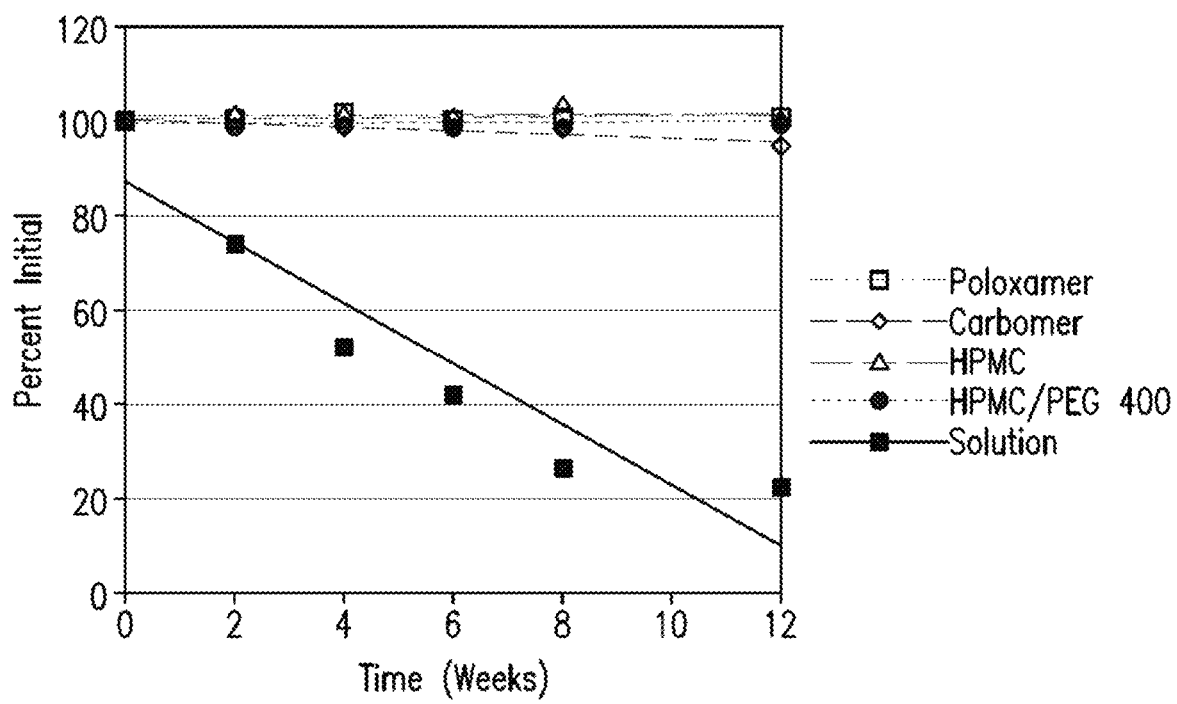
FIG. 1B shows the percent of compound I in the exploratory formulations after 12 weeks at 40° C.

Results from the testing for compound I stability at room temperature and 40° C. are shown in FIG. 1A and FIG. 1B, respectively. In FIG. 1A, the formulation with percent of compound I at about 70% of original at 12 weeks is the formulation of compound I as a solution. In FIG. 1B, the formulation with percent of compound I at about 20% of original at 12 weeks is the formulation of compound I as a solution. As seen in FIGS. 1A and 1B compound I remains in stable form in the suspensions, without significant degradation even at 12 weeks at 40° C. In contrast, the part of compound I in solution in the supernatant (FID121513) degrades to about 20% of initial amount after 12 weeks at 40° C.

Figure 2:
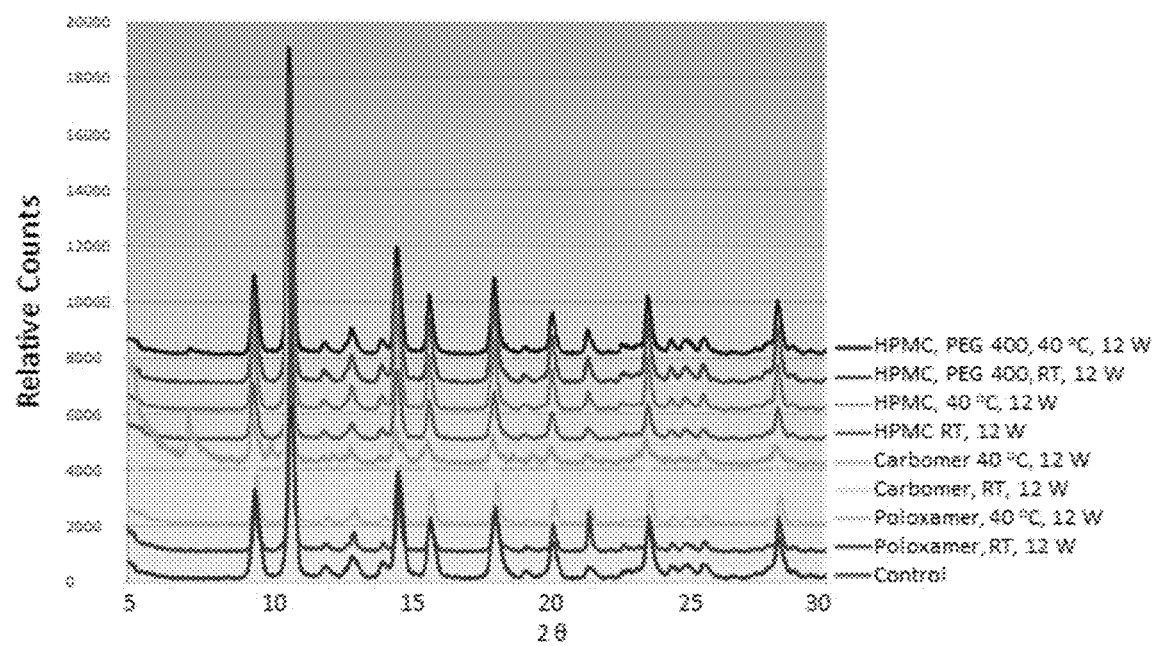
FIG. 2 shows the X-ray Powder Diffraction Patterns of compound I Recovered from 12-Week Stability Samples versus Control.

At the end of the study, compound I was recovered from the four suspensions and evaluated for changes in crystalline form by x-ray powder diffraction. The x-ray diffraction patterns of compound I recovered from the 12-week stability samples and that of compound I stored at room temperature (control) are presented in FIG. 2. As seen in FIG. 2, compound I in each of the four exploratory formulations maintains its polymorphic form even after storage at room temperature or 40° C. for 12 weeks.

In addition, the suspension FID 121744 (shown below in Table 6) and a 10% compound I slurry in 1% tyloxapol were subjected to heat sterilization 171° C. for 1 hour. The X-ray diffraction pattern of compound I after sterilization was identical to an untreated sample.

Example 3. Viscosity Range Finding Studies of Compound I Suspensions

Various suspension formulations of compound I were evaluated for viscosity and settling of compound I. A series of unpreserved compound I suspensions were prepared containing varying amounts of carbopol (Carbomer homopolymer Type B) and varying amounts of sodium chloride. The compositions of the formulations are shown in Table 4.

TABLE 4

Compositions of compound I unpreserved suspensions of compound I for viscosity range finding studies

| | FID: | | | | |
|---|---|---|---|---|---|
| | 121845 | 121724 | 121846 | 121847 | 121848 |
| Component | | | Percent w/w | | |
| Compound I | 0.5 | 0.5 | 0.5 | 0.5 | 0.5 |
| Tyloxapol | 0.05 | 0.05 | 0.05 | 0.05 | 0.05 |
| Carbopol 974P [a] | 0.1 | 0.2 | 0.3 | 0.4 | 0.5 |
| Glycerin | 2.0 | 2.0 | 2.0 | 2.0 | 2.0 |
| Sodium Chloride | — | — | — | — | — |
| Tromethamine | qs pH 7.4 | qs pH 7.4 | qs pH 7.4 | qs pH 7.4 | qs pH 7.4 |
| Hydrochloric Acid | qs pH 7.4 | qs pH 7.4 | qs pH 7.4 | qs pH 7.4 | qs pH 7.4 |
| Purified Water | qs 100 | qs 100 | qs 100 | qs 100 | qs 100 |

[a] Carbomer homopolymer Type B

The suspensions were evaluated visually for uniformity. The suspension which contained only 0.1% Carbomer, FID 121845, was not uniform and therefore was not evaluated further. Sodium chloride is known to reduce the viscosity of Carbomer-containing suspensions, so sodium chloride was added to aliquots of the remaining four suspensions to obtain a total of 28 suspensions with concentrations of 0.2, 0.3, 0.4 and 0.5% Carbomer and 0, 0.05, 0.1, 0.15, 0.2, 0.25 and 0.3% sodium chloride.

Results from the viscosity testing of 28 suspensions are shown in Table 5.

TABLE 5

Viscosities (cP) of compound I unpreserved suspensions from Table 4 (CP52, 60 RPM @ 25° C.)

| FID | Sodium chloride (% w/w) | | | | | | |
|---|---|---|---|---|---|---|---|
| (% carbomer) | 0 | 0.05 | 0.1 | 0.15 | 0.2 | 0.25 | 0.3 |
| 121724 (0.2) | Out of range | 64.5 | 23.9 | 14.6 | 10.4 | 7.59 | 7.44 |
| 121846 (0.3) | Out of range | Out of range | 101.2 | 59.8 | 38.0 | 25.6 | 18.9 |
| 121847 (0.4) | Out of range | Out of range | Out of range | Out of range | 121.1 | 84.0 | 63.7 |
| 121848 (0.5) | Out of range | Out of range | Out of range | Out of range | Out of range | Out of range | 150.8 |

As seen from Table 5, the relationship between the amounts of carbomer and sodium chloride affect the viscosity of the suspension.

A further set of unpreserved suspensions of compound I containing carbopol as a suspending agent were prepared for viscosity range finding and settling studies. The compositions, their viscosities and settling times of 10 ml of suspension after 6 months are shown in Table 6.

TABLE 6

Unpreserved suspensions of compound I and their viscosities and settling properties

| Component | FID: 121744 | 121896 | 121897 | 121898 | 121899 |
|---|---|---|---|---|---|
| | Percent w/w | | | | |
| Compound I | 0.5 | 0.5 | 0.5 | 0.5 | 0.5 |
| Tyloxapol | 0.05 | 0.05 | 0.05 | 0.05 | 0.05 |
| Carbopol 974P $^a$ | 0.2 | 0.2 | 0.2 | 0.2 | 0.2 |
| Glycerin | 2.0 | 2.0 | 2.0 | 2.0 | 2.0 |
| Sodium Chloride | 0.05 | 0.06 | 0.07 | 0.08 | 0.09 |
| Tromethamine | qs pH 7.4 | qs pH 7.4 | qs pH 7.4 | qs pH 7.4 | qs pH 7.4 |
| Hydrochloric Acid | qs pH 7.4 | qs pH 7.4 | qs pH 7.4 | qs pH 7.4 | qs pH 7.4 |
| Purified Water | qs 100 | qs 100 | qs 100 | qs 100 | qs 100 |
| Viscosity (cP) | 153.4 | 113.2 | 84.8 | 66.4 | 49.8 |
| Settling, ml (%) | <0.2 (<2%) | <0.2 (<2%) | <0.2 (<2%) | — | <0.2 (<2%) |

$^a$ Carbomer Homopolymer Type B

A further series of preserved suspensions containing hypromellose as the suspending agent were prepared and their viscosities measured. The settling properties were measured as follows: well mixed aliquots of the suspensions were filled into 10 ml glass graduated cylinders. The graduated cylinders were sealed with ground glass stoppers and Parafilm® and allowed to sit undisturbed for six months at room temperature. The settled suspension was estimated by visual inspection. The compositions, their viscosities and settling times of 10 ml of suspension after 6 months are shown in Table 7.

TABLE 7

Preserved suspensions of compound I and their viscosities and settling properties

| Component | FID: 121801 | 121901 | 121902 | 121903 |
|---|---|---|---|---|
| | Percent w/w | | | |
| Compound I | 0.5 | 0.5 | 0.5 | 0.5 |
| Tyloxapol | 0.05 | 0.05 | 0.05 | 0.05 |
| Hypromellose | 0.5 | 0.6 | 0.7 | 0.8 |
| Boric Acid | 0.3 | 0.3 | 0.3 | 0.3 |
| Mannitol | 0.3 | 0.3 | 0.3 | 0.3 |
| Propylene Glycol | 1.5 | 1.5 | 1.5 | 1.5 |
| Polyquaternium-1 | 0.001 | 0.001 | 0.001 | 0.001 |
| Sodium Hydroxide | qs pH 7.4 | qs pH 7.4 | qs pH 7.4 | qs pH 7.4 |
| Hydrochloric Acid | qs pH 7.4 | qs pH 7.4 | qs pH 7.4 | qs pH 7.4 |
| Purified Water | qs 100 | qs 100 | qs 100 | qs 100 |
| Viscosity (cP) | 20.0 | 32.0 | 50.2 | 76.4 |
| Settling, ml (%) | 0.6 (6%) | 0.4 (4%) | 0.2 (2%) | — |

Based on the results shown in Table 6 and Table 7, compound 1 suspensions that are preserved or unpreserved and that have either carbomer or hypromellose as a suspending agent were able to achieve acceptable viscosities and settling properties. As described supra, acceptable viscosities for the formulations of the present disclosure are in the range of about 20-200 cPs, measured using a CP52 spindle at 60 rpm and at room temperature.

Example 4. pH Dependent Stability Screening of Compound I Suspensions

In order to test the pH stability of compound I suspensions, the formulations listed in Table 8 below were prepared. All samples contain 0.1% compound I in order to keep drug concentration consistent. As this amount of drug was not soluble in any of the samples, 0.1% tyloxapol was used as a surfactant to aid in re-suspending the material in the samples. All samples (except the TRIS sample) contain an equivalent amount of phosphate buffer. All samples were placed in 20 mL glass vials and put on condition at 60° C. At each assay time point, samples were allowed to equilibrate to room temperature, vortexed to resuspend the drug, and samples were diluted to concentrations that fell within the linear range of the standard curve.

TABLE 8

Compound I stability sample compositions

| Component | pH 5 | pH 6 | pH 7 | pH 8 | Carbopol | HPMC | TRIS |
|---|---|---|---|---|---|---|---|
| | Percent w/w | | | | | | |
| Compound I | 0.1 | 0.1 | 0.1 | 0.1 | 0.1 | 0.1 | 0.1 |
| Tyloxapol | 0.1 | 0.1 | 0.1 | 0.1 | 0.1 | 0.1 | 0.1 |

TABLE 8-continued

Compound I stability sample compositions

| Component | pH 5 | pH 6 | pH 7 | pH 8 | Carbopol | HPMC | TRIS |
|---|---|---|---|---|---|---|---|
| | | | | | Percent w/w | | |
| Hypromellose | — | — | — | — | — | 0.5 | — |
| Carbopol | — | — | — | — | 0.4 | — | — |
| Monobasic sodium phosphate | 0.13 | 0.13 | 0.13 | 0.13 | 0.13 | 0.13 | — |
| Dibasic sodium phosphate | 0.01 | 0.01 | 0.01 | 0.01 | 0.01 | 0.01 | — |
| Tromethamine | — | — | — | — | — | — | 0.03 |
| Sodium hydroxide | pH 5.0 | pH 6.0 | pH 7.0 | pH 8.0 | pH 7.4 | pH 7.4 | pH 7.4 |
| Hydrochloric acid | pH 5.0 | pH 6.0 | pH 7.0 | pH 8.0 | pH 7.4 | pH 7.4 | pH 7.4 |
| Purified water | Qs 100 | Qs 100 | Qs 100 | Qs 100 | Qs 100 | Qs 100 | Qs 100 |

The amount of compound I in the stability samples was tested at 0, 4, 7, and 11 days by high performance liquid chromatography (HPMC), using a Waters XBridge Shield RP18 Column (3.5 μm, 3.0×150 mm, 30° C.), using a gradient of mobile phase A 0.1% TFA in water and mobile phase B 0.1% TFA in acetonitrile, with an injection volume of 10 μl and a flow rate of 0.8 ml/min. In addition, the major degradant appearing at a relative retention time (RRT) of 1.23 was tracked. Results from the stability testing are shown in Table 9.

The major degradant shown in Table 9 was observed to crystallize out to form large crystals as its concentration increases. The following formulations shown in Table 10 were therefore prepared and analyzed for degradant formation.

TABLE 10

Compound I stability sample compositions

| Component | 2% PVP | 5% HPβCD | 5% SBE-CD | 0.1% CaCl$_2$ | CaCl$_2$/HPMC | 0.5% HPMC | 1% TRIS |
|---|---|---|---|---|---|---|---|
| | | | | Percent w/v | | | |
| Compound I | 0.1 | 0.1 | 0.1 | 0.1 | 0.1 | 0.1 | 0.1 |
| Tyloxapol | 0.1 | 0.1 | 0.1 | 0.1 | 0.1 | 0.1 | 0.1 |
| Povidone K30 | 2 | — | — | — | — | — | — |
| Hypromellose | — | — | — | — | 0.5 | 0.5 | — |
| HP-β-cyclodextrin | — | 5 | — | — | — | — | — |
| Sulfobutyl-cyclodextrin | — | — | 5 | — | — | — | — |
| Calcium chloride | — | — | — | 0.1 | 0.1 | — | — |
| Sodium citrate | 0.05 | 0.05 | 0.05 | 0.05 | 0.05 | 0.05 | 0.05 |
| Tromethamine | pH 6.0 | pH 6.0 | pH 6.0 | pH 6.0 | pH 6.0 | pH 6.0 | 1.0 |
| HCl | pH 6.0 | pH 6.0 | pH 6.0 | pH 6.0 | pH 6.0 | pH 6.0 | pH 6.0 |
| Purified water | Qs 100 | Qs 100 | Qs 100 | Qs 100 | Qs 100 | Qs 100 | Qs 100 |

Data on the stability of compound I in compositions shown in Table 10 is shown below in Table 11.

TABLE 9

Stability of compound I and degradant growth at 60° C.

| Condition | Compound I stability (% initial) | | | | % Degradant @ RRT 1.23 | | | |
|---|---|---|---|---|---|---|---|---|
| | Initial | Day 4 | Day 7 | Day 11 | Initial | Day 4 | Day 7 | Day 11 |
| pH 5 | 100 | 95.5 | 91.2 | 85.6 | 0 | 2.3 | 2.8 | 3.9 |
| pH 6 | 100 | 97.5 | 95.3 | 93.0 | 0 | 1.2 | 2.1 | 2.2 |
| pH 7 | 100 | 95.7 | 92.3 | 87.8 | 0 | 2.0 | 2.2 | 4.0 |
| pH 8 | 100 | 79.9 | 63.4 | 40.9 | 0 | 5.7 | 13.5 | 29.1 |
| Carbopol (pH 7.4) | 100 | 93.2 | 86.2 | 75.4 | 0 | 3.3 | 6.5 | 11.0 |
| HPMC (pH 7.4) | 100 | 94.4 | 89.8 | 83.3 | 0 | 2.9 | 5.1 | 8.2 |
| TRIS (pH 7.4) | 100 | 98.6 | 96.2 | 94.4 | 0 | 1.1 | 2.0 | 2.6 |

TABLE 11

Stability of Compound I in Suspension at 40° C. and 60° C.

| 0.1% Compound I | % Initial of compound I at 40° C. | | | | % Initial of compound I at 60° C. | | |
|---|---|---|---|---|---|---|---|
| | Initial | Day 15 | Day 35 | Day 56 | Initial | Day 7 | Day 15 |
| 2% PVP | 100 | 98.5 | 97.0 | 95.4 | 100 | 94.5 | 87.6 |
| 5% HP-β-CD | 100 | 97.3 | 95.2 | 92.9 | 100 | 91.4 | 82.0 |
| 5% SBE-CD | 100 | 92.4 | 87.1 | 84.0 | 100 | 83.3 | 66.9 |
| 0.1% CaCl$_2$ | 100 | 98.4 | 97.6 | 96.3 | 100 | 94.7 | 87.3 |
| CaCl$_2$/HPMC | 100 | 97.7 | 97.0 | 94.7 | 100 | 93.4 | 87.4 |
| 0.5% HPMC | 100 | 97.7 | 96.4 | 95.7 | 100 | 93.1 | 89.9 |
| 1% TRIS | 100 | 97.4 | 95.9 | 93.7 | 100 | 89.8 | 79.5 |

Data on the degradant growth is shown in Table 12.

TABLE 12

Compound I degradant growth in suspension at 40° C. and 60° C.

| 0.1% Compound I | % Deg @ RRT 1.23 at 40° C. | | | % Deg @ RRT 1.23 at 60° C. | | |
|---|---|---|---|---|---|---|
| | Initial | Day 15 | Day 35 | Day 56 | Initial | Day 7 | Day 15 |
| 2% PVP | 0 | 0.6 | 1.4 | 1.7 | 0 | 2.5 | 2.4 |
| 5% HP-β-CD | 0 | 0.9 | 2.0 | 2.9 | 0 | 3.6 | 7.7 |
| 5% SBE-CD | 0 | 2.5 | 5.5 | 7.1 | 0 | 7.4 | 12.5 |
| 0.1% CaCl$_2$ | 0 | 0.4 | 0.9 | 1.5 | 0 | 2.2 | 2.4 |
| CaCl$_2$/HPMC | 0 | 0.6 | 1.4 | 1.9 | 0 | 2.5 | 5.5 |
| 0.5% HPMC | 0 | 0.5 | 1.1 | 1.5 | 0 | 2.0 | 4.1 |
| 1% TRIS | 0 | 0.7 | 1.6 | 1.7 | 0 | 3.0 | 7.8 |

Based on the stability data in the above Tables, it was concluded that the stability of compound I varies greatly over the pH range of 5-8. Further, increasing the solubility of compound I in SBE-cyclodextrin resulted in a decrease in the stability.

Example 5. Stability of 2.5%, 1.5%, 0.5% and 1.5% Ophthalmic Suspensions of Compound I The stability of a number of lots of compound I ophthalmic suspensions 0.15%, 0.5%, 1.5% and 2.5% (initial pH of 7.34-7.7) as described below in Table 18 were evaluated by monitoring the chemical, physical and microbiological stability characteristics of the product over time. The chemical stability was evaluated by monitoring compound I and its impurities. The physical stability was evaluated by monitoring the pH, osmolality, viscosity, appearance, identity by X-ray Powder Diffraction (XRPD), and particle size. The microbiological stability was evaluated by conducting sterility tests. A summary of the results (in ranges from different lots and various sampling times over the testing period) from the tests and stability monitoring limits for compound I ophthalmic suspensions are presented in Table 13.

In addition to the above parameters, viscosity was monitored and found to be within 10% of the initial viscosity at each tested time point under each storage condition. Particle size measurements and sterility were also within stability monitoring limits. Further, the inventors unexpectedly found that compound I that were micronized by ball milling in the final step of manufacturing maintained polymorphic form B without changing crystalline character.

Example 6. Acute Toxicology Study of Exploratory Formulations

The four formulations from the exploratory stability studies in Table 2, FID 121522, FID 121511, FID 121512, FID 121513 were dosed in male NZW rabbits 5 times in one day, using a sterile irrigating solution as a control. No toxicity was observed for the four exploratory formulations or the control.

Example 7. Pharmacokinetic Study of Exploratory Formulations

A pharmacokinetics study was conducted to determine the ocular uptake of compound I following single bilateral topical ocular dosing of male NZW rabbits with the four exploratory formulations provided in Table 2: FID 121522, FID 121511, FID 121512, FID 121513. Results are shown in Table 14.

TABLE 14

Summary of compound I $C_{max}$ and $C_{min}$ Results from pharmacokinetic study

| Matrix | | FID: 121522 | 121511 | 121512 | 121513 |
|---|---|---|---|---|---|
| | | Concentration (nM) | | | |
| Cornea | $C_{max}$ | 34700 | 15760 | 16400 | 901 |
| | $C_{min}$ | 3900 | 4520 | 1470 | BLQ* |
| Conjunctiva | $C_{max}$ | 24500 | 4680 | 5270 | 165 |
| | $C_{min}$ | 1570 | 1420 | 2770 | BLQ |
| Aqueous Humor | $C_{max}$ | 3730 | 1780 | 1940 | 185 |
| | $C_{min}$ | 98.9 | 55.4 | 20.1 | BLQ |

TABLE 13

Stability testing data for ophthalmic suspensions of compound I

| | | Condition monitored | | | |
|---|---|---|---|---|---|
| Storage condition | Compound I suspension (w/v) | % compound I of label | Total impurities (No more than 6.0%) | Impurity at RRT of 1.2 (No more than 4.5%) | pH Range: 6.8-8.0 | Osmolality Range: 200-350 mOsm/kg (initial 231-251) |
| 25 ± 2° C./ 40% ± 5% RH (up to 26 weeks) | 2.5% | 98-100 | 0.0-0.2 | <0.1-0.2 | 7.53-7.61 | 231-247 |
| | 1.5% | 99-100 | 0.1-0.2 | 0.1-0.2 | 7.52-7.63 | 243-244 |
| | 0.5% | 96-98 | 0.2-0.5 | 0.2-0.5 | 7.49-7.51 | 242-243 |
| | 0.15% | 95-99 | 0.3-1.6 | 0.3-1.6 | 7.54-7.60 | 236-244 |
| 40 ± 2° C./ <25% ± 5% RH (up to 26 weeks) | 2.5% | 98-103 | 0.2-0.6 | 0.2-0.6 | 7.52-7.58 | 235-240 |
| | 1.5% | 100-102 | 0.3-0.9 | 0.3-0.9 | 7.52-7.59 | 244-255 |
| | 0.5% | 97-97 | 0.7-2.4 | 0.7-2.4 | 7.48-7.52 | 246-251 |
| | 0.15% | 85-95 | 1.2-8.6 | 1.2-8.6 | 7.45-7.56 | 239-252 |
| 5 ± 2° C./ 35% ± 5% RH (up to 104 weeks) | 2.5% | 96-102 | 0.1-0.4 | <0.1-0.2 | 7.45-7.59 | 230-245 |
| | 1.5% | 98-102 | 0.2-0.2 | 0.0-2.2 | 7.46-7.60 | 241-244 |
| | 0.5% | 97-98 | 0.2-0.2 | 0.2-0.2 | 7.54 | 240 |
| | 0.15% | 96-102 | 0.1-0.4 | 0.2-0.4 | 7.54-7.62 | 238-242 |

TABLE 14-continued

Summary of compound I $C_{max}$ and $C_{min}$
Results from pharmacokinetic study

| Matrix | | FID: | | | |
|---|---|---|---|---|---|
| | | 121522 | 121511 | 121512 | 121513 |
| | | Concentration (nM) | | | |
| Iris-Ciliary Body | $C_{max}$ | 3640 | 1480 | 1800 | 153 |
| | $C_{min}$ | 223 | 169 | 65 | BLQ |
| Plasma | $C_{max}$ | 63 | 30.2 | 43.5 | 0.834 |
| | $C_{min}$ | 2.18 | 1.00 | 0.741 | BLQ |
| | $IC_{50}$ | 30 | 30 | 30 | 30 |

*BLQ = Below Limit of Quantitation
Cmin determined at 4 hours after administration.

As seen in Table 14, the highest exposures of compound I was in the cornea, which was approximately 1.5 to 3 times the levels observed in the conjunctiva, and approximately 10 times the levels observed in the aqueous humor and iris-ciliary body and approximately 500 times the levels observed in plasma. In the cornea, $C_{max}$ for the suspension with Poloxamer 407 was approximately 2 times the $C_{max}$ for the two suspensions with hypromellose and approximately 38 times the $C_{max}$ for the solution formulation. For the three suspensions, $C_{max}$ in the cornea ranged from approximately 500 to 1200 times the $IC_{50}$ of 30 nM, while $C_{min}$ ranged from approximately 50 to 130 times the $IC_{50}$.

Example 8. Pharmacokinetic Study of Further Formulations

Based on the results from the exploratory formulations, further formulations were prepared for additional pharmacokinetic studies on the corneal and aqueous humor concentrations of compound I following single bilateral topical ocular dosing in male pigmented rabbits. These formulations are shown in Table 15.

TABLE 15

Unpreserved Suspension Formulations of Compound I for PK Study

| | FID: | | |
|---|---|---|---|
| | 121746 | 121745 | 121744 |
| Component | Percent w/w | | |
| Compound I | 0.01 | 0.05 | 0.5 |
| Tyloxapol | 0.05 | 0.05 | 0.05 |
| Carbomer Homopolymer Type B | 0.2 | 0.2 | 0.2 |
| Glycerin | 2.0 | 2.0 | 2.0 |
| Sodium Chloride | 0.05 | 0.05 | 0.05 |
| Tromethamine | qs pH 7.4 | qs pH 7.4 | qs pH 7.4 |
| Hydrochloric Acid | qs pH 7.4 | qs pH 7.4 | qs pH 7.4 |
| Purified Water | qs 100 | qs 100 | qs 100 |

Results from the pharmacokinetic study are shown in Table 16.

TABLE 16

Summary of Cmax and Cmin Results from PK Study

| | | FID: | | |
|---|---|---|---|---|
| | | 121746 | 121745 | 121744 |
| Matrix | | Concentration (nM) | | |
| Cornea | $C_{max}$ | 1150 | 5550 | 18500 |
| | $C_{min}$ | 14 | 20 | 223 |

TABLE 16-continued

Summary of Cmax and Cmin Results from PK Study

| | | FID: | | |
|---|---|---|---|---|
| | | 121746 | 121745 | 121744 |
| Matrix | | Concentration (nM) | | |
| Aqueous Humor | $C_{max}$ | 314 | 950 | 2990 |
| | $C_{min}$ | BLQ* | BLQ | 11.1 |
| | $IC_{50}$ | 30 | 30 | 30 |

*Below limit of quantitation
Cmin results obtained at 8 hours after dosing

As seen in Table 16, $C_{max}$ and $C_{min}$ for compound I show that the highest exposures of compound I were in the cornea, with levels approximately 3 to 6 times the levels observed in the aqueous humor. In the cornea, $C_{max}$ for the 0.5% suspension was approximately 3 times that of the 0.05% suspension and approximately 16 times that of the 0.01% suspension. In the aqueous humor, $C_{max}$ for the 0.5% suspension was approximately 3 times that of the 0.05% suspension and approximately 9 times that of the 0.01% suspension. For the three suspensions, $C_{max}$ in the cornea ranged from approximately 38 to 600 times the $IC_{50}$ of 30 nM, while $C_{min}$ ranged from approximately 0.5 to 7 times the $IC_{50}$.

A pharmacokinetics study was conducted to determine the corneal and aqueous humor concentrations of compound I following single bilateral topical ocular dosing in intact eyes and following anterior keratectomy with and without bandage contact lenses in male pigmented rabbits using the formulations described in Table 15, FID121746, FID121745, and FID121744.

Results from the pharmacokinetic study are shown in Table 17.

TABLE 17

Summary of $C_{max}$ and $AUC_{0-8\ h}$ Results from PK Study of rabbits following anterior keratectomy

| | | FID: | | | | |
|---|---|---|---|---|---|---|
| | | 121746 | 121745 | | 121744 | |
| | | w/o CL[a] | w/o CL[a] | w/CL[b] | w/o CL[a] | w/CL[b] |
| Corneas | | Concentration (nM; AUC: nM · h) | | | | |
| Intact | $C_{max}$ | 1147 | 5550 | | 18500 | |
| | $AUC_{0-8\ h}$ | 1433 | 4550 | | 31700 | |
| Anterior | $C_{max}$ | | 1910 | 1490 | | 10700 |
| Keratectomy | $AUC_{0-8\ h}$ | | 1770 | 4400 | | 26700 |
| | $IC_{50}$[c] | 27 | 27 | 27 | 27 | 27 |

[a]Without bandage contact lenses
[b]With bandage contact lenses
[c]IC50 for N-arachidonoyl dopamine (NADA)

Example 9. Toxicology Wound Healing Study with Compound I Suspension Formulations A toxicology wound healing study was conducted to evaluate corneal wound healing following QID bilateral topical ocular dosing of compound I after unilateral laser photorefractive keratectomy in rabbits with and without bandage contact lenses. The compound I formulations used in the study are described in Table 18. For comparator purposes, ketorolac tromethamine (ACULAR LS®) and dexamethasone (MAXIDEX®) formulations were used.

TABLE 18

Compositions of Compound I Vehicle and
Suspensions for Wound Healing Study

| | FID: | | | |
|---|---|---|---|---|
| Component | 121830 | 121744 | 121816 | 121814 |
| | Percent w/w | | | |
| Compound I | | 0.5 | 1.5 | 2.5 |
| Tyloxapol | 0.05 | 0.05 | 0.05 | 0.05 |
| Carbomer Homopolymer Type B | 0.2 | 0.2 | 0.2 | 0.2 |
| Glycerin | 2.0 | 2.0 | 2.0 | 2.0 |
| Sodium Chloride | 0.05 | 0.05 | 0.05 | 0.05 |
| Tromethamine | qs pH 7.4 | qs pH 7.4 | qs pH 7.4 | qs pH 7.4 |
| Hydrochloric Acid | qs pH 7.4 | qs pH 7.4 | qs pH 7.4 | qs pH 7.4 |
| Purified Water | qs 100 | qs 100 | qs 100 | qs 100 |

The study results demonstrated that after 3 days, the mean wound areas for the corneas treated with 0.5, 1.5 and 2.5% compound I suspensions with bandage contact lenses were smaller than those for the corneas treated with ACULAR LS and MAXIDEX with bandage contact lenses, vehicle without bandage contact lenses and for untreated corneas. The mean wound areas for the corneas treated with 0.5, 1.5 and 2.5% compound I suspensions with bandage contact lenses were comparable to those for the corneas treated with vehicle with bandage contact lenses and 2.5% compound I without bandage contact lenses.

Example 10. Bacteriostasis/Stability Studies of Exemplary Compound I Suspensions A series of five prototype sterile suspension formulations containing 0.5% compound I were prepared and screened for bacteriostasis/fungistasis with five compendia) organisms: *S. aureus, P. aeruginosa, E. coli, C. albicans* and *A. brasiliensis*. The criterion for stasis was no more than 0.5 log increase in microbial counts (CFU/mL). All the tested formulations demonstrated an acceptable level of bacteriostasis/fungistasis. In addition, a 2.5% compound I suspension (otherwise identical to FID 121744), and suspension vehicle were also prepared and screened for bacteriostasis/fungistasis screening. Bacteriostasis/fungistasis was observed through 3 days with an inoculum of ~$10^6$ and/or an inoculum of ~$10^5$.

Example 11. First in Human Study of Compound I

This example describes a first-in-human study of compound I conducted in healthy volunteers. A total of 54 subjects were administered to study medication. Part 1 of the first in human study administered single ascending doses of 0.15%, 1.5%, 2.5% w/v (1 drop) of compound I in an eye drop.

Part 2 tested multiple ascending doses (MAD) of compound I, administering (i) 1 drop of 0.15%, 1.5%, 2.5%, 4 times daily (every 6 hours) for 7 days or (ii) 1 drop of 2.5%, 8 times daily (every 3 hours) for 7 days (supra-therapeutic dose) as eye drops.

Part 3 was an esthesiometry assessment to evaluate the anesthetic properties of compound I. Part 3 of the study had four arms, with compound I, vehicle, tetracaine (0.5% ophthalmic solution, used as a positive control) and diclofenac sodium (0.1% ophthalmic solution, used as the active NSAID comparator). Ocular anesthetic was selected because of its established anesthetic effect; however it is not the standard of care due to its negative effect on wound healing. NSAID is the current standard of care for corneal pain after PRK with minimal anesthetic but significant pain control properties. Vehicle eye drops were used as a negative control to enable better determination of the potential anesthetic effect. Twelve healthy subjects, who met the eligibility criteria, were randomized to receive a single eye drop of 4 study treatments, each during 1 of 4 different study days (Days 1, 4, 7 and 10). Each subject was randomized to receive the study treatment according to one of the following four sequences:

Sequence 1: Anesthetic, NSAID, compound I 2.5%, Vehicle

Sequence 2: NSAID, Vehicle, Anesthetic, compound I 2.5%

Sequence 3: Vehicle, compound I 2.5%, NSAID, Anesthetic

Sequence 4: compound I 2.5%, Anesthetic, Vehicle, NSAID

Safety assessments: Safety assessments consisted of collecting all adverse events (AEs), serious adverse events (SAEs), including systemic and ocular adverse events, along with their severity and relationship to study drug. Systemic safety assessments included regular monitoring of hematology, blood chemistry and urinalysis performed at study center and regular assessments of physical examination, vital signs (systolic and diastolic blood pressure, pulse rate, and body temperature), ECG, pregnancy and assessments of fertility and hand immersion test at 49° C. during MAD part. Ocular safety assessments included early treatment diabetic retinopathy study (ETDRS) visual acuity, intraocular pressure, slit-lamp biomicroscopy, corneal staining and dilated fundus exam.

Subjects were selected based on the following inclusion and exclusion criteria.

Inclusion Criteria:

Written informed consent was obtained before any assessment was performed.

Healthy male and female subjects aged 18 to 50 years (inclusive), and in good health as determined by past medical history, physical examination, vital signs, ECG, and laboratory tests at Screening.

At Screening, and Baseline, vital signs (systolic and diastolic blood pressure (BP) and pulse rate) were assessed in the sitting position after the subject had rested for at least 3 minutes and again after 3 minutes in the standing position. Sitting vital signs were required to be within the normal range the following ranges:

oral body temperature between 35.0-37.5° C.

systolic blood pressure (SBP), 90-150 mmHg diastolic blood pressure (DBP), 50-90 mmHg pulse rate, 40-100 bpm Subjects were required to weigh at least 50 kg to participate in the study, with a body mass index (BMI) within the range of 18-29 kg/m2. BMI=Body weight (kg)/[Height (m)]$^2$ Subjects who were able to communicate well with the Investigator, to understand and comply with the requirements of the study.

For Part 3, subjects Baseline levels of eye sensitivity were to be in the range of 50 to 60 mm (inclusive) as measured by the Cochet-Bonnet esthesiometer.

Exclusion Criteria:

Women of child-bearing potential, defined as all women physiologically capable of becoming pregnant, unless they were using effective methods of contraception during dosing of study treatment.

Subjects, who demonstrated any medical condition (systemic or ophthalmic) that was, in the opinion of the Investigator, and based on the content of the Investigator brochure, preclude the safe administration of test article or safe participation in this study.

Part 3 (esthesiometry): subjects who were using contact lenses at the time of the study or had used in the past 3 years were excluded to minimize variability in corneal sensitivity because of contact lens use.

History of any ocular surgery or laser within the past 6 months prior to Screening. History of any chronic eye disease other than refractive error, incipient cataract, strabismic amblyopia, or anisometropic amblyopia. Subjects with a history of acute eye disease (such as infection, corneal abrasion or allergy) within the past 6 months from Screening were eligible if the disease was not active.

Any currently active ocular condition that required use of topical eye drops.

Subjects using continuous positive airway pressure or other sleep apnea devices.

Safety Results from the First in Human Study

Based on results from Parts 1, 2, and 3, the Maximum Tolerated Dose (MTD) was identified as the maximum feasible concentration of 2.5%, 8 times daily for 7 days. No dose limiting adverse events were identified at this dose level. All adverse events of suspected causality to compound I were of mild severity, except for moderate severity eye irritation that lead to discontinuation of treatment in one patient of the 2.5% 4 times daily cohort. The most frequent ocular adverse events in the compound I treated patients were corneal staining, hyperemia and mild anterior chamber inflammation, in levels similar to placebo. A summary of the adverse events from the SAD study are shown in Table 19.

TABLE 19

Overall incidence of AEs - number of events and number of subjects (Part 1: SAD) (Safety analysis set)

| | Compound I 0.15% N = 6 nE, nS (%) | Compound I 1.5% N = 6 nE, nS (%) | Compound I 2.5% N = 6 nE, nS (%) | Vehicle N = 6 nE, nS (%) | Total N = 24 nE,nS(%) |
|---|---|---|---|---|---|
| AEs, Subjects with AEs | 3, 1 (16.7) | 3, 2 (33.3) | 0, 0 (0.0) | 4, 3 (50.0) | 10, 6 (25.0) |
| AEs of Mild severity | 3, 1 (16.7) | 3, 2 (33.3) | 0, 0 (0.0) | 3, 2 (33.3) | 9, 5 (20.8) |
| AEs of Moderate severity | 0, 0 (0.0) | 0, 0 (0.0) | 0, 0 (0.0) | 1, 1 (16.7) | 1, 1 (4.2) |
| Study drug-related AEs | 3, 1 (16.7) | 3, 2 (33.3) | 0, 0 (0.0) | 3, 2 (33.3) | 9, 5 (20.8) |
| Serious AEs | 0, 0 (0.0) | 0, 0 (0.0) | 0, 0 (0.0) | 0, 0 (0.0) | 0, 0 (0.0) |
| AEs leading to discontinuation of study | 0, 0 (0.0) | 0, 0 (0.0) | 0, 0 (0.0) | 1, 1 (16.7) | 1, 1 (4.2) |
| Study-drug related AEs leading to discontinuation of study | 0, 0 (0.0) | 0, 0 (0.0) | 0, 0 (0.0) | 1, 1 (16.7) | 1, 1 (4.2) |

N = number of subjects enrolled and received the study drug
nE = number of treatment emergent AE events in the category
nS = number of subjects with at least one treatment emergent AE in the category Percent is based on the number of subjects A summary of the adverse events from the SAD study are shown in Table 20.

TABLE 20

Overall incidence of AEs - number of events and number of subjects (Part 2: MAD) (Safety analysis set)

| | Compound I 0.15% 4 times daily N = 6 nE, nS (%) | Compound I 1.5% 4 times daily N = 6 nE, nS (%) | Compound I 2.5% 4 times daily N = 6 nE, nS (%) | Compound I 2.5% 8 times daily N = 6 nE, nS (%) | Vehicle N = 8 nE, nS | Total N = 32 nE, nS (%) |
|---|---|---|---|---|---|---|
| AEs, Subjects with AEs | 6, 3 (50.0) | 12, 5 (83.3) | 4, 2 (33.3) | 3, 2 (33.3) | 13, 3 (37.5) | 38, 15 (46.9) |
| AEs of Mild severity | 6, 3 (50.0) | 11, 5 (83.3) | 3, 2 (33.3) | 3, 2 (33.3) | 12, 3 (37.5) | 35, 15 (46.9) |
| AEs of Moderate severity | 0, 0 (0.0) | 1, 1 (16.7) | 1, 1 (16.7) | 0, 0 (0.0) | 1, 1 (12.5) | 3, 3 (9.4) |
| Study drug-related AEs | 5, 2 (33.3) | 9, 3 (50.0) | 4, 2 (33.3) | 2, 1 (16.7) | 10, 3 (37.5) | 30, 11 (34.4) |
| Serious AEs (0.0) | 0, 0 | 0, 0 (0.0) | 0, 0 (0.0) | 0, 0 (0.0) | 0, 0 (0.0) | 0, 0 (0.0) |
| AEs leading to discontinuation of study | 0, 0 (0.0) | 0, 0 (0.0) | 1, 1 (16.7)[a] | 0, 0 (0.0) | 0, 0 (0.0) | 1, 1 (3.1) |
| Study-drug related AEs | 0, 0 (0.0) | 0, 0 (0.0) | 1, 1 (16.7) | 0, 0 (0.0) | 0, 0 (0.0) | 1, 1 (3.1) |

N = number of subjects enrolled and received the study drug
nE = number of treatment emergent AE events in the category
nS = number of subjects with at least one treatment emergent AE in the category Percent is based on the number of subjects
[a]Subject treated with compound I 2.5% 4 times daily experienced eye discharge, ocular hyperemia (both of mild severity) and eye irritation (moderate severity) in the left eye on Day 6., leading to discontinuation of the administration of study drug.

For the hand immersion test, all subjects in the treatment cohorts withdrew their hand from water at 49° C. at a time interval between 0 to ≤50 secs. No subjects lasted longer than 22 secs and no meaningful change in immersion time was observed between compound I and vehicle-treated subjects. The results therefore indicate that compound I does not alter temperature sensitivity of the subjects.

Esthesiometry Study (Part 3)

The first-in-human study further evaluated potential anesthetic effect of topical ocular 2.5% compound I by esthesiometry testing, i.e. measurement of the filament length (cm) when the threshold of cornea touch is perceived.

An analysis of the results showed that tetracaine 0.5% had an anesthetic effect with approximately 10 minutes of duration of action (positive control). Both diclofenac 0.1% and vehicle had no anesthetic effect on the cornea, as expected based on known clinical experience with diclofenac. Compound I 2.50% showed no anesthetic effect at any time point after treatment.

For measures of corneal sensitivity, statistical and clinical significance were observed while comparing least squares means (Test vs Ref) for the following:

Tetracaine 0.5% (N=12) vs Vehicle (N=12) at 2.5 minutes, 10 minutes and 20 minutes post-dose;

Tetracaine 0.5% (N=12) vs Diclofenac 0.1% (N=12) at 2.5 minutes, 10 minutes and 20 minutes post-dose;

Compound I 2.5% (N=11) vs Tetracaine 0.5% (N=12) at 2.5 minutes and 10 minutes post-dose No difference was seen in corneal sensitivity between compound I 2.5% and vehicle, with all p-values greater than or equal to 0.395 at scheduled time points up to 30 minutes post-dose. This study demonstrated a lack of anesthetic effect of 2.5% compound I when compared to tetracaine 0.5% (drug with anesthetic effect as positive control) and vehicle (placebo).

Pharmacokinetic Summary from First in Human Study

After both single and multiple topical ocular suspension doses of compound I 0.15%, 1.5%, and 2.5%, plasma PK profile showed rapid absorption of compound I into systemic circulation and low concentration exposures achieved with moderate variability across subjects. Increase in dose from 0.15% to 2.5% resulted in less than dose-proportional increase in systemic exposure. Accumulation of compound I at steady-state was minor (~1.7-fold) following administration of 0.15%, 1.5% or 2.5% suspension 4 times daily and also minor (—0.1.3-fold) following 2.5% 8 times daily for 7 days.

Example 12. Clinical Study of Compound I for Treatment of Postoperative Pain

This example describes a clinical study of compound I (4-(7-hydroxy-2-isopropyl-4-oxo-4H-quinazolin-3-yl)-benzonitrile) in the treatment of postoperative ocular pain in patients undergoing photorefractive keratectomy (PRK) surgery. The formulation used is illustrated in Table 18.

| Primary objective | Endpoints related to primary objective |
| --- | --- |
| To evaluate pain control in the immediate post-operative period. | Visual analog scale (VAS) pre-dose pain assessment at 6 hours post-operatively<br>Average ocular pain VAS assessments from the first post-operative assessment up to the pre-dose 12 hour assessment |
| Secondary objectives | Endpoints related to secondary objectives |
| To evaluate the efficacy of compound I 2.5% eye drops four times daily for reducing use of oral analgesics following PRK procedure | Incidence and amount of rescue oral analgesics needed in 6 hours, 12 hours, 24 hours, 2 days, and 3 days post-operatively after each PRK surgery. |
| To assess safety and tolerability of compound I 2.5% eye drops four times daily | Adverse events (AEs) and serious adverse events (SAEs)<br>Visual acuity, intraocular pressure (IOP), dilated fundus exam, ocular hyperemia<br>Size of epithelial defect by slit lamp exam<br>Blink rate, tear production<br>Vital signs (blood pressure, pulse rate, and body temperature) |
| To evaluate pain severity post-operatively | All VAS measurements during the first 3 days after surgery |
| To assess the systemic exposure after ocular dosing of compound I 2.5% eye drops four times daily at various time points in PRK patients | Plasma concentration of compound I |
| Exploratory objectives | Endpoints related to exploratory objectives |
| To explore wound healing rate | Size of epithelial defect by anterior segment Optical coherence tomography (OCT) |
| To explore effect on pain relief of compound I versus Vehicle after instillation of eye drop | VAS scores before and after instillation of eye drop (three time points) |
| To explore effect of compound I on ocular pain and quality of life | Ocular Pain Assessment Survey (OPAS) |
| compound I exposure in the bandage contact lens (BCL) | Residual compound I amount after treatment |

Study Objectives

Study Design

The study was a proof of concept, double-masked, randomized, vehicle-controlled study of compound I administered as eye drops in addition to standard of care treatment in patients after PRK surgery. PRK surgery was performed as an outpatient procedure under topical anesthesia with removal of the corneal epithelium to expose the stroma for the laser ablation. Compound I dosing was as single eye drop of 2.5% (0.925 mg/drop), administered four times daily (every six hours) in one eye from immediate post-op (time 0) to last dose at 72 hours.

Vehicle dosing was as a single drop, administered four times daily (every six hours) in one eye from immediate post-operative (time 0) to last dose at 72 hours.

The study consisted of 2 treatment periods using a crossover design. Patients underwent PRK surgery on 2 separate occasions (periods), one eye at a time. Patients were randomized to receive either compound 1 or vehicle following procedure 1 and the alternate following procedure 2.

Forty patients were randomized in a 1:1 ratio to two sequences: compound I during period 1, followed by vehicle in period 2, or vehicle during period 1 followed by compound I during period 2. Each patient was administered one drop four times daily for 72 hours following PRK surgery on their study eye (Day 1, Periods 1 and 2). The initial study eye was the non-dominant eye as established at screening and in agreement of the patient and the investigator. The patients returned for follow-up visits on Days 2, 3, 4 and 8 of Period 1 after surgery in the first eye, with optional daily visits to follow the patient until wound healing was complete. The second eye surgery was not performed if any complications were noticed.

The patients underwent PRK surgery on their second study eye (dominant eye) on Period 2, Day 1. The PRK surgery was performed after the epithelial defect of the first eye was resolved and at the discretion of the Investigator. Following the PRK surgery, the patients received the opposing treatment four times daily for 72 hours. Patients returned daily for the first 3 postoperative days (Period 2, Days 2-4) and at one week after the second surgery (Period 2, Day 8), with optional daily visits to follow the patient until wound healing was complete. An end of study (EOS) visit took place 30 days after the second eye surgery (or after final dose of investigational product when the patient ended treatment early in Period 1).

All patients received standard of care treatment during periods 1 and 2 of the study, including application of a bandage contact lens (Air Optix® Night and Day® Aqua or equivalent) following the PRK procedure and before receiving study drops for pain. A course of topical ocular antibiotic (Moxifloxacin or equivalent 1 eye drop four times daily) was started after application of first dose of study drops and was continued for 4-7 days. Prednisolone acetate ophthalmic one eye drop four times daily was administered for one week after PRK, followed by taper. Preservative-free unit-dose artificial tears were used as needed. The first dose of study drops after each PRK procedure was administered by site staff. Subsequent doses were self-administered. A gap of 5 minutes was allowed between eye drop administrations in sequence. To summarize, patients underwent PRK procedure, bandage lens was placed on the cornea, compound I or Vehicle was administered; after approximately 5 minutes antibiotic was administered, and after another 5 minutes, prednisolone was administered.

Rescue medication consisted of oral analgesic (acetaminophen 300 mg+codeine 30 mg) as needed up to a total of 10 tabs/day or 1-2 tabs every 4 hours.

Additional Study Treatment

All patients received standard of care ancillary treatment following PRK surgery, including:

Bandage contact lens (Air Optix® Night and Day® Aqua or equivalent)

A course of topical ocular antibiotic (Moxifloxacin or equivalent 1 eye drop four times daily) was started right after PRK surgery, and after application of first dose of study eye drop and continued for 4-7 days, per managing physician.

Prednisolone acetate ophthalmic: one eye drop four times daily was started immediately following PRK surgery and after instillation of antibiotic eye drop and was administered for 1 week after PRK, followed by taper per local procedures.

Preservative-free unit-dose artificial tears were used as needed. Artificial tears were not allowed to be chilled for analgesic effect.

The drops were administered in sequence, with a gap of at least 5 minutes between eye drop administrations.

Inclusion Criteria

Population eligible for inclusion in this study had to fulfill all of the following criteria:

Male and female patients aged 18 to 75 years eligible for bilateral PRK surgery.

Normal eye exam except for refractive error at Baseline.

Planned myopia correction was required not to exceed −4.00 Diopters (sphere) and 3.00 diopters of astigmatism, with spherical equivalent not higher than −4.50, confirmed by manifest refraction at Baseline. Monovision treatment (such as correction for far distance in one eye and for intermediate distance in the fellow eye) was allowed.

Written informed consent was obtained before any assessment was performed.

Exclusion Criteria

Monocular patient (including amblyopia) or best corrected visual acuity (BCVA) score worse than 20/80 (Snellen) or 55 letters [early treatment diabetic retinopathy study (EDTRS)] at Baseline.

Any systemic or ocular disease that affected wound healing (such as severe rheumatoid arthritis or diabetes or history of keloid formation) or a history of ocular trauma, uveitis, infection, or inflammation in the 6 months prior to Baseline. Especially for diabetes: Patients with severe diabetes, uncontrolled diabetes, diabetic keratopathy, diabetic retinopathy, diabetic macular edema, diabetic nephropathy, diabetic foot ulcers or other systemic complications of diabetes were excluded. Patients with mild, well-controlled diabetes with no evidence of ocular or systemic complications of diabetes were included.

Patients with active inflammatory or infectious ocular conditions, severe or progressive retinal disease, and use of topical or systemic steroids, or use of Coumadin or similar drugs within the last 6 months prior to Baseline.

Patients with any corneal dystrophy (epithelial, stromal or endothelial) or any cornea disease (including significant scarring (at the discretion of the Investigator), ocular herpes or pterygium).

Previous refractive or corneal surgery (such as LASIK, PRK, radial keratotomy, pterygium removal, corneal transplantation).

History of allergic or hypersensitivity reaction or significant AEs to any of the drugs used in this study including tetracaine or similar topical ocular anesthetic, NSAIDs and aspirin, oral analgesic (including acetaminophen and codeine), antibiotics, steroids and inability to tolerate or wear bandage contact lens Concurrent therapy or history of chronic therapy or abuse of systemic or ocular NSAIDs, analgesics, pain medication (including gabapentin or pregabalin and similar), opiates or *cannabis*.

Patients who used any topical eye medication except for lubricating eye drops within two weeks prior to surgery in the study eye were excluded. Patients meeting any of the following were excluded:

Usage of topical NSAIDs during 30 days before Baseline, OR

Systematic/chronic usage of systemic NSAIDS within 30 days prior to Baseline, OR Occasional usage of systemic NSAIDS within 3 days prior to Baseline, OR Usage of ocular cyclosporine (or similar medication) within the 3 months prior to surgery.

Patients with body weight<50 kg, or who do not have a body mass index (BMI) within the range of 18-35 kg/m$^2$. BMI=Body weight (kg)/[Height (m)]$^2$ Pregnant or nursing (lactating) women. Women of childbearing potential, defined as all women physiologically capable of becoming pregnant, unless they are using basic methods of contraception during dosing of investigational drug.

No additional exclusions were applied by the Investigator, in order that the study population was the representative of all eligible patients.

Study Population

The study population was comprised of male and female patients eligible for PRK surgery between 18 and 75 years old (inclusive). A total of 40 patients were planned. A total of 44 patients were screened and of them 40 patients were enrolled in the study and randomized.

Patient selection was established based on a review of all eligibility criteria at Screening and Baseline. A relevant record (e.g. checklist) of the eligibility criteria was stored with the source documentation at the study site. Deviation from any entry criterion excluded a patient from enrollment into the study.

Patient demographics are provided in Table 21.

TABLE 21

Patient demographics by treatment sequence (Safety analysis set)

| | | Vehicle/ compound I 2.5% N = 20 | compound I 2.5%/ Vehicle N = 20 | Total N = 40 |
|---|---|---|---|---|
| Age (years) | Mean (SD) | 34.4 (10.77) | 33.7 (8.94) | 34.0 (9.78) |
| | Median | 33.5 | 32.0 | 33.0 |
| | Range | 20-54 | 23-56 | 20-56 |
| Sex - n (%) | Male | 11 (55%) | 10 (50%) | 21 (53%) |
| | Female | 9 (45%) | 10 (50%) | 19(48%) |
| Race - n (%) | White | 18 (90%) | 17 (85%) | 35 (88%) |
| | Asian | 2 (10%) | 1 (5%) | 3 (8%) |
| | Black Or African American | 0 | 1 (5%) | 1 (3%) |
| | Multiple | 0 | 1 (5%) | 1 (3%) |
| Ethnicity - n (%) | Not Hispanic Or Latino | 19 (95%) | 18 (90%) | 37 (93%) |
| | Hispanic Or Latino | 1 (5%) | 2 (10%) | 3 (8%) |
| Weight (kg) | Mean (SD) | 84.1 (14.86) | 78.8 (14.07) | 81.5 (14.53) |
| | Median | 84.7 | 76.1 | 79.2 |
| | Range | 60-119 | 57-107 | 57-119 |

TABLE 21-continued

Patient demographics by treatment sequence (Safety analysis set)

| | | Vehicle/ compound I 2.5% N = 20 | compound I 2.5%/ Vehicle N = 20 | Total N = 40 |
|---|---|---|---|---|
| Height (cm) | Mean (SD) | 170.4 (7.40) | 173.2 (6.96) | 171.8 (7.23) |
| | Median | 171.3 | 174.1 | 172.7 |
| | Range | 155-184 | 161-185 | 155-185 |
| BMI (kg/m$^2$) | Mean (SD) | 28.9 (3.98) | 26.2 (3.73) | 27.5 (4.04) |
| | Median | 29.7 | 26.0 | 27.5 |
| | Range | 21-35 | 21-35 | 21-35 |

Treatment Arms

Patients were assigned to one of the following 2 treatment sequences in a ratio of 1:1 lasting 3 days per period.

| Sequence | Period 1 | Period 2 |
|---|---|---|
| 1 | Compound I 2.5% 4 times daily (every 6 hours) for 72 hours (inclusive) | Vehicle control 4 times daily (every 6 hours) for 72 hours (inclusive) |
| 2 | Vehicle control 4 times daily (every 6 hours) for 72 hours (inclusive) | Compound I 2.5% 4 times daily (every 6 hours) for 72 hours (inclusive) |

Compound I was administered to the patient as ocular drops. Drops were administered at the study site by the study personnel during the day of PRK surgery. During the daily follow-up postoperative visits, when the patient was at the site during the expected time for eye drop administration, the study personnel was required to administer the eye drops. The remainder of drops were home administered by the patient, or when the patient was present at the study site for a visit (e.g., at 24, 48 and 72 hours post-surgery).

Visual Acuity Scale

Patient subjective experience of pain was recorded using VAS, a numeric assessment of pain between 0 and 100, with 0 representing no pain, and 100 representing worst imaginable pain. Previous studies of pain in PRK showed that the most intense pain was experienced within the first 12 hours after surgery with the peak around 4-6 hours after surgery (Sher et al., Refract Corneal Surg. November-December; 9(6):425-36 (1993)), and these were the time points selected for primary endpoint analysis. Since it was important clinically to both decrease the maximum pain as well as the overall pain that the patient experiences during the immediate postoperative period, the two periods of 6 hours and up to 12 hours postoperatively, were evaluated as primary endpoints. All evaluable VAS data was collected using an ePRO, which was an electronic device (cell phone with software application), on which patients marked their pain levels at the appropriate time points.

Rescue oral analgesics: It is not ethical to refuse pain control medication to patients postoperatively as part of a clinical trial. A review of pror clinical trials indicated that NSAIDs are used for postoperative pain after PRK as rescue oral analgesics, similar to the Standard of care after PRK. Because the use of oral rescue medication may be a potential confounder of the pain VAS evaluation, three approaches were used when analyzing pain VAS scores to account for the influence of pain meds (assuming 4 hours of rescue medication effect): (1) any recorded VAS score within 4 hours after use of rescue medication was considered missing; (2) all the recorded VAS scores was used; and (3) any recorded VAS scores within 4 hours after rescue medication use was imputed by the record taken prior to the rescue medication.

Primary Efficacy Results

Figure 3:
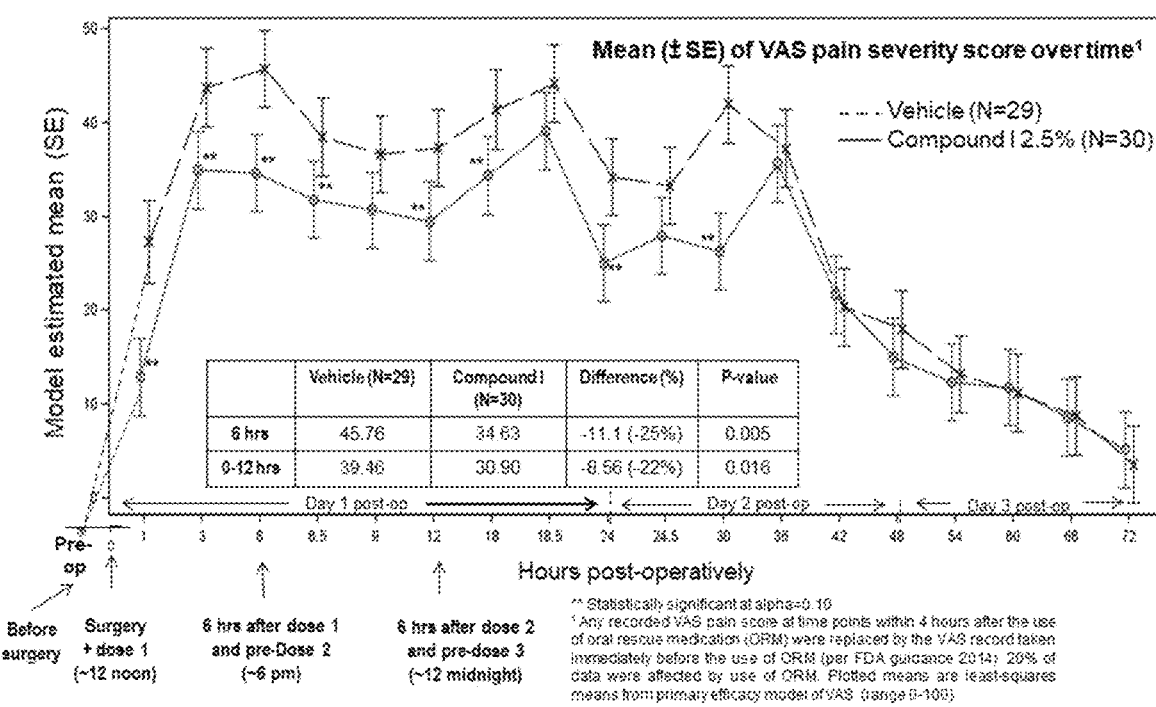
FIG. 3 shows the model estimated mean (+/− SE) of visual analog scale (VAS) pain assessment over time (Primary PD analysis set).

The mean VAS pain severity scores at 6 hours and 0-12 hours post-operatively are presented in Table 22 and Table 23, respectively, and shown in FIG. 3. The primary analysis was performed using the Primary PD analysis set.

The treatment differences in mean VAS pain severity scores at 6 hours and over 0-12 hours period post-operatively between compound I and Vehicle were statistically significant with p-values less than 0.10.

The model based means treatment difference (compound I—Vehicle) in VAS pain severity scores at 6 hours post-operatively was −11.1 (90% CI: (−17.54, −4.71; p=0.005) and at 0-12 hours period post-operatively was −8.56 (90% CI: (−14.29, −2.83; p=0.016). Thus, the primary efficacy objective of the study was met.

The treatment differences in mean VAS pain severity scores at 6 hours and over 0-12 hours period post-operatively between compound I and Vehicle were statistically significant with p-values less than 0.10.

TABLE 22

Mean VAS pain severity scores at 6-hours post-operatively (Primary PD analysis set)

| Model estimated mean* | | Comparison of model based means: compound I vs. Vehicle | | | |
|---|---|---|---|---|---|
| (SE) | | Diff | | | |
| compound I (N = 30)# | Vehicle (N = 29) | (compound I − Vehicle) | % Diff | 90% CI | P-value |
| 34.63 (4.05) | 45.76 (4.10) | −11.1 | −25% | (−17.54, −4.71) | 0.005 |

*To account for oral rescue medication (ORM) use, any recorded VAS pain scores taken up to 4 hours after the use of ORM was replaced with the VAS score recorded just before use of ORM, per FDA guidance 2014. # ePRO data from the first 10 patients (out 40 total) were not evaluable due to failure of the first vendor/ePRO device

TABLE 23

Mean VAS pain severity scores 0-12 hours post-operatively (Primary PD analysis set)

| Model estimated mean* | | Comparison of model based means: compound I vs. Vehicle | | | |
|---|---|---|---|---|---|
| (90% CI) | | Diff | | | |
| compound I (N = 30) | Vehicle (N = 29) | (compound I − Vehicle) | % Diff | 90% CI | P-value |
| 30.90 (24.04, 37.76) | 39.46 (32.54, 46.39) | −8.56 | −22% | (−14.29, −2.83) | 0.016 |

*To account for oral rescue medication (ORM) use, any recorded VAS pain scores taken up to 4 hours after the use of ORM was replaced with the VAS score recorded just before use of ORM, per FDA guidance 2014.

Secondary Efficacy Results

The number of patients who did not use oral rescue medication (ORM) was higher in compound I-treated eye compared to the Vehicle-treated eye at 0-6 hours, 0-12 hours and 0-24 hours post-operatively. After 36 hours post-operation, the same number of patients took ORM in compound I vs. Vehicle (Table 24).

TABLE 24

Summary of oral rescue medication use incidence (number of patients who did not use oral rescue medication) (Secondary PD analysis set)

| Time interval | compound I 2.5% N = 40 n (%) | Vehicle N = 40 n (%) | p-value |
|---|---|---|---|
| 0-6 hours post-operatively | 23 (57.5%) | 19 (47.5%) | 0.2891 |
| 0-12 hours post-operatively | 19 (47.5%) | 16 (40.0%) | 0.5811 |
| 0-24 hours post-operatively | 16 (40.0%) | 12 (30.0%) | 0.3438 |
| 0-2 days post-operatively | 11 (27.5%) | 11 (27.5%) | 1.0000 |
| 0-3 days post-operatively | 11 (27.5%) | 11 (27.5%) | 1.0000 | n: Number of patients who did not use oral rescue medication (ORM)
* For the both treatment sequences column, n represents the number of patients who did not use oral rescue medication (ORM) in any treatment group.

Figure 4:
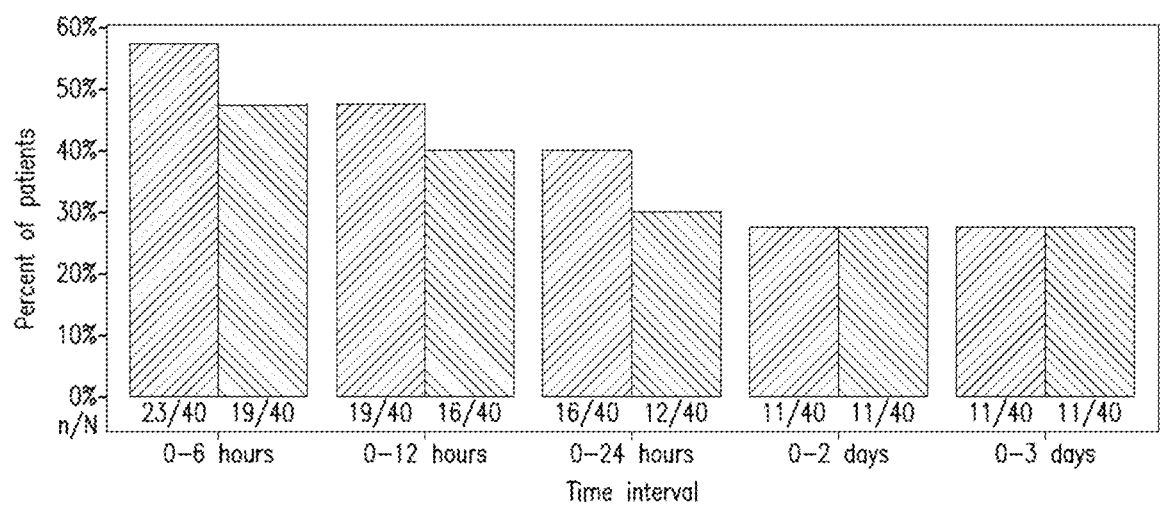
FIG. 4 shows a histogram of oral rescue medication use incidence (number of patients who did not use oral rescue medication) (Secondary PD analysis set). For each of the time periods, the right bar represents subjects who were administered compound I, while the left bar represents subjects who were administered vehicle. The percent of patients who did not use oral rescue medication (ORM) is presented in the y-axis. n/N represents the count/total number of patients at each treatment.

Histogram of oral rescue medication (ORM) use incidence (number of patients who did not use ORM) is displayed in FIG. 4.

The summary and analysis of amount of ORM (number of pills per patient) is presented in Table 25.

TABLE 25

Summary of amount of oral rescue medication (Number of pills) (Secondary PD analysis set)

| Time interval | Statistics | compound I N = 40 | Vehicle N = 40 | % Change (Compound I − Vehicle)/ Vehicle |
|---|---|---|---|---|
| 0-6 hours post-operatively | Mean (SD) Range p-value | 0.75 (1.032) 0.0-4.0 0.10* | 1.00 (1.132) 0.0-4.0 | −25% |
| 0-12 hours post-operatively | Mean (SD) Range p-value | 1.40 (1.780) 0.0-6.0 0.26 | 1.65 (1.847) 0.0-6.0 | −15% |
| 0-24 hours post-operatively | Mean (SD) Range p-value | 2.35 (2.751) 0.0-10.0 0.05* | 2.80 (3.006) 0.0-12.0 | −16% |
| 0-48 hours post-operatively | Mean (SD) Range p-value | 4.05 (4.466) 0.0-16.0 0.05* | 4.68 (5.225) 0.0-20.0 | −13% |
| 0-72 hours post-operatively | Mean (SD) Range p-value | 4.33 (4.896) 0.0-21.0 0.07* | 5.05 (5.574) 0.0-22.0 | −14% |

*Obtained from a Wilcoxon signed rank test
N = total number of patients at each treatment
*Statistical significance with p ≤ 0.10 (per primary endpoint power calculation)

As seen in Table 25 and FIG. 4, in every time interval during the study there was less ORM taken during compound I vs. Vehicle treatment The summary and analysis of amount of ORM (mg/kg of body weight) is presented in Table 26.

In every time interval, amount of ORM (mg/kg of body weight) was less during compound I vs. Vehicle treatment (Table 26). During the periods 0-6 hours, 0-24 hours, 0-48 hours and 0-72 hours post-operatively the difference in milligrams per kilogram of body weight was statistically significant (p≤0.10).

TABLE 26

Summary of amount of oral rescue medication (mg/kg of body weight) (Secondary PD analysis set)

| Time interval | Statistics | Compound I N = 40 | Vehicle N = 40 | % Change (Compound I – Vehicle)/ Vehicle |
|---|---|---|---|---|
| 0-6 hours post-operatively | Mean (SD) Range p-value | 3.32 (4.684) 0.0-19.2 0.09* | 4.41 (5.038) 0.0-17.1 | −25% |
| 0-12 hours post-operatively | Mean (SD) Range p-value | 6.10 (8.062) 0.0-28.7 0.21 | 7.39 (8.478) 0.0-28.7 | −17% |
| 0-24 hours post-operatively | Mean (SD) Range p-value | 10.17 (12.335) 0.0-47.9 0.05* | 12.41 (14.130) 0.0-57.5 | −18% |
| 0-48 hours post-operatively | Mean (SD) Range p-value | 17.59 (19.850) 0.0-76.6 0.05* | 20.51 (23.991) 0.0-95.8 | −14% |
| 0-72 hours post-operatively | Mean (SD) Range p-value | 18.70 (21.509) 0.0-87.4 0.06* | 22.06 (25.527) 0.0-105.4 | −15% |

*Obtained from a Wilcoxon signed rank test
N = total number of patients at each treatment
*Statistical significance with p ≤ 0.10 (per primary endpoint power calculation)
Each acetaminophen/codeine tablet is considered as 330 mg in the calculation of amount (mg/kg of body weight).

VAS Pain Severity During the First 3 Days after PRK Surgery

After PRK surgery, patients reported statistically significantly lower VAS pain severity scores after treatment with compound I compared to Vehicle at p-value threshold 0.10 in 6 out of the 7 time points checked during the first 18 hours after surgery, starting with the hour 1 after surgery. The VAS pain severity scores were lower for compound I than Vehicle at all scheduled time points up to and including 36 hours after surgery. At all-time points from 36 hours until the end of the VAS collection period at 72 hours after PRK surgery, the difference between compound I VAS scores and Vehicle VAS scores was only marginally different, and there was no statistically significant difference between the scores at the p-value threshold of 0.10.

VAS Pain Severity Scores Before and After Instillation of Study Eye Drop

The mean changes in VAS scores from time points 6.5, 18.5 and 24.5 hours post-operative compared one-half hour prior to that and immediately before instillation of eye drops (namely at hours 6, 18 and 24) were −3.1, 2.8 and 1.3, respectively for compound I-treated eyes. For Vehicle-treated eyes the same differences were −5.6, 2.2 and −0.2, respectively.

Ocular Pain Assessment Survey (OPAS)

The OPAS is a validated instrument for quantifying and monitoring corneal and ocular surface pain and quality of life, developed in response to an identified need from a National Eye Institute Workshop in 2010. See Qazi et al., *Ophthalmology* July 123(7):1458-1468 (2016). The rating scale of the overall pain severity in the OPAS from Qazi et al. rated from 0 (no pain) to 10 (severe pain) or for frequency of symptoms from 0% (never) to 100% (all the time), as per the survey. The patients were asked to fill out the OPAS survey/questionnaire at Day 2, Day 4 (at the end of treatment period with study drug) and Day 8. Statistical analysis of OPAS results was not performed. Of the total of 27 OPAS questions, the results of seven questions are presented below.

Figure 5A:
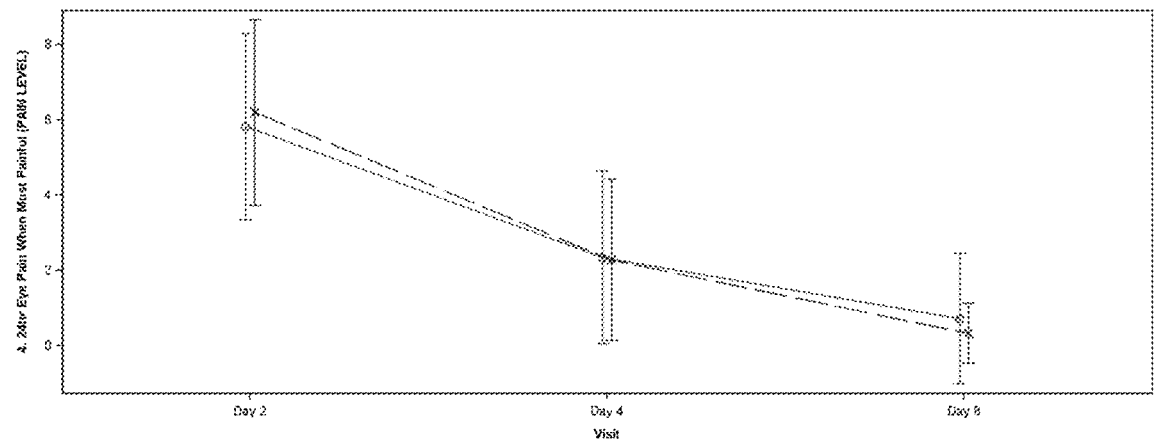
FIGS. 5A-C provide the arithmetic mean (+/− SD) of ocular pain assessment survey (OPAS) over time for questions 4, 5, and 6 (Secondary PD analysis set).
Figure 5B:
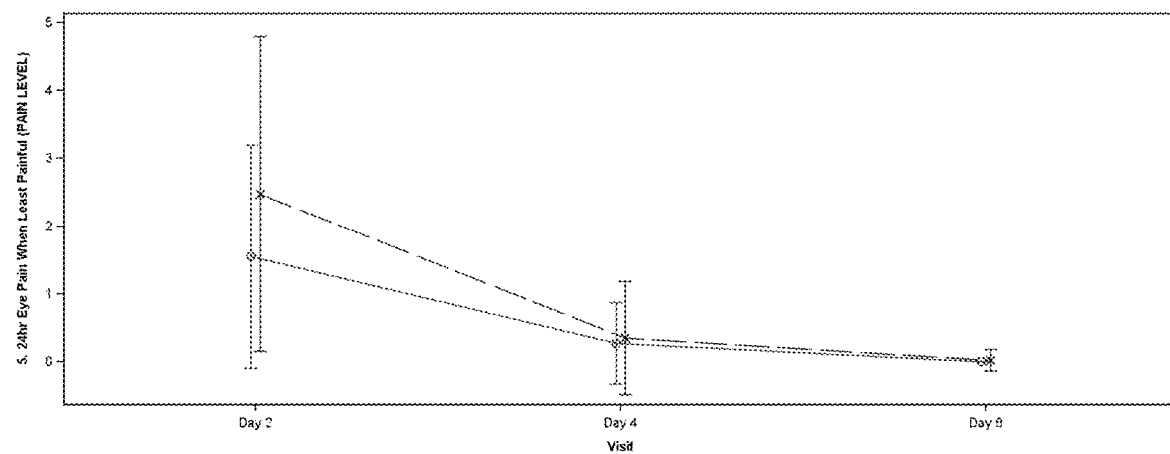
Figure 5C:
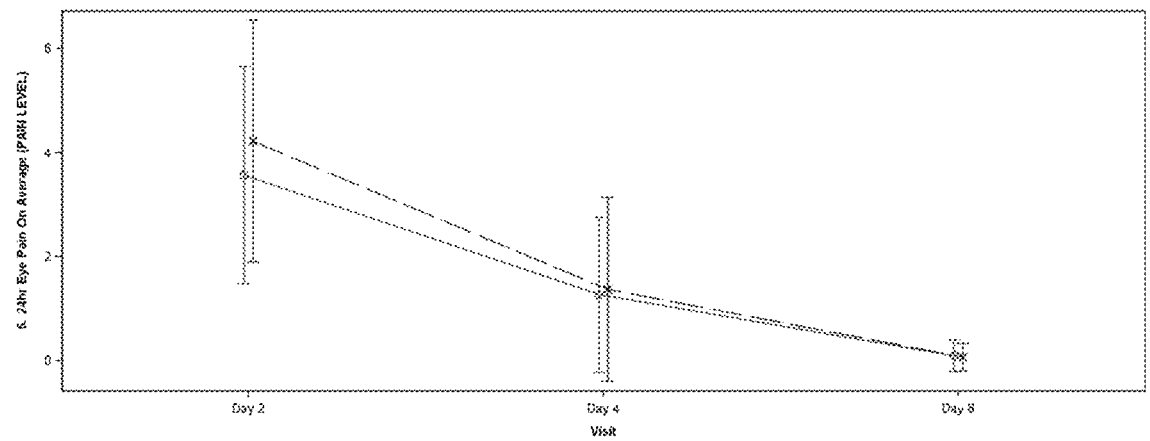
Figure 6A:
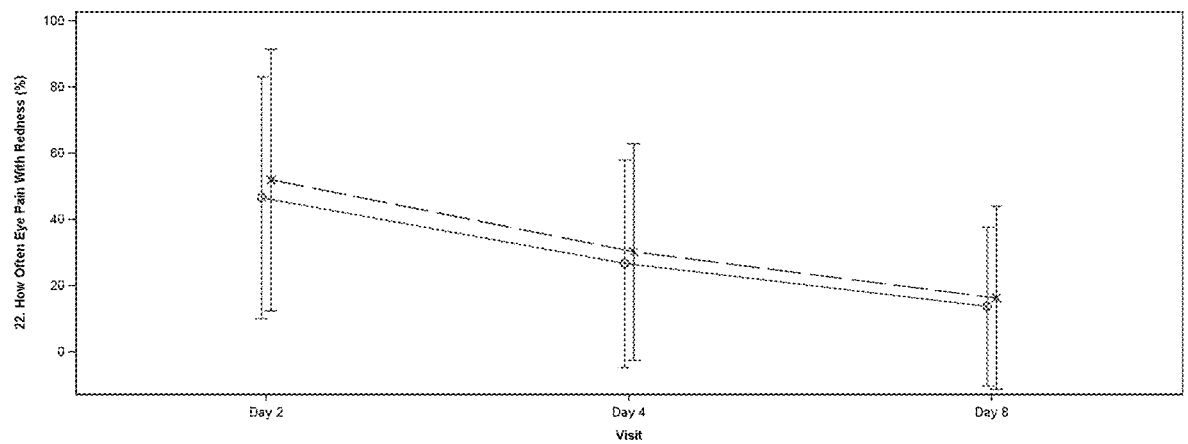
FIGS. 6A-D provide the arithmetic mean (+/− SD) of ocular pain assessment survey (OPAS) over time for questions 22, 23, 24 and 25 (Secondary PD analysis set).
Figure 6B:
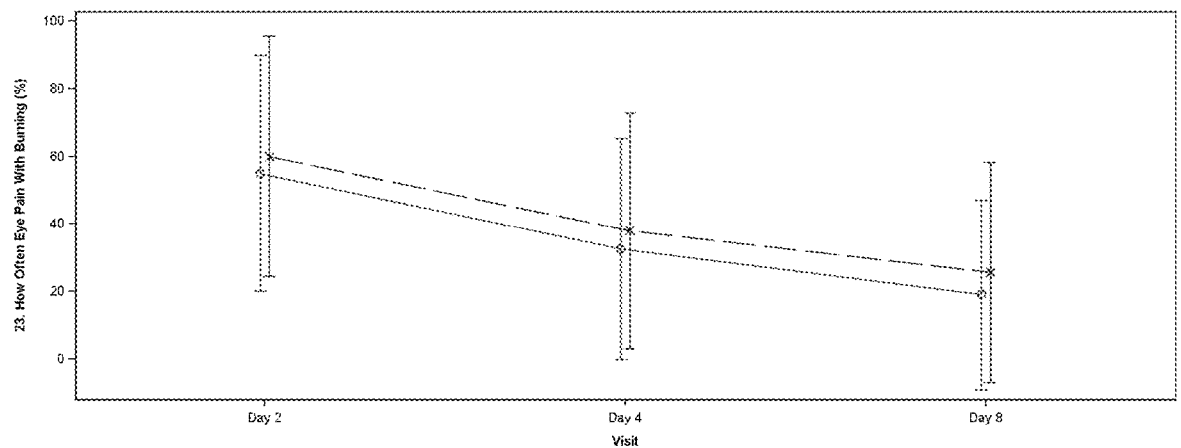
Figure 6C:
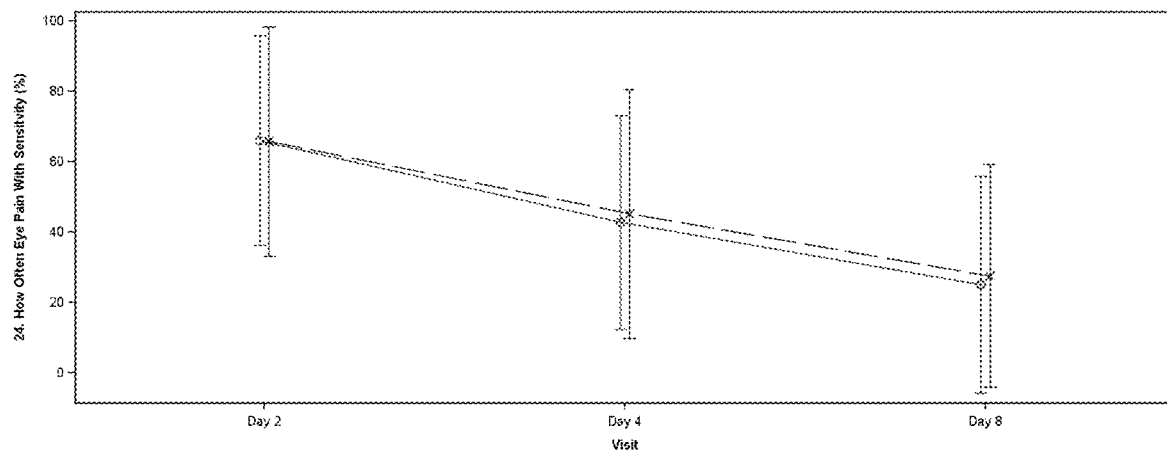
Figure 6D:
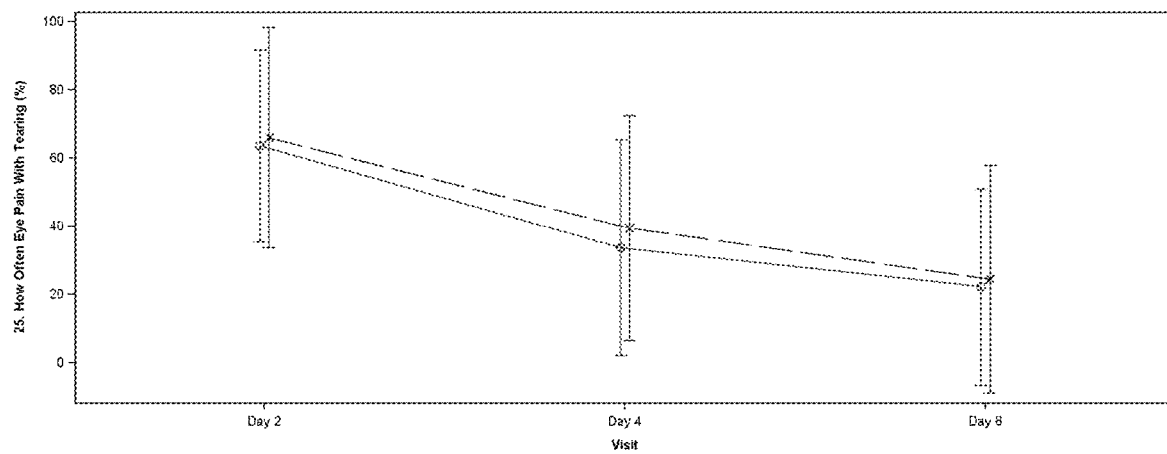

In the questions of eye pain intensity during the previous 24 hours at the level of eye pain that is the most painful (question 4), level of pain that is the least painful (question 5) and level of eye pain in average (question 6) at Day 2 all 3 answers numerically favored compound I compared to Vehicle (FIG. 5A, FIG. 5B, FIG. 5C).

In the questions of how often eye pain was associated by the following symptoms: redness (question 22), burning (question 23), sensitivity to light (question 24) and tearing (question 25), all answers favored compound I compared to Vehicle (FIGS. 6A, 6B, 6C, and 4D). Thus, patients administered compound I exhibited lower levels of eye pain associated with redness, burning, sensitivity to light (photophobia), and tearing compared to patients administered placebo.

Summary Exploratory Ocular Results

Ocular Pain Assessment Survey (OPAS) showed better pain control and quality of life patients during the compound I vs. the Vehicle treatment period.

In the questions of eye pain intensity during the previous 24 hours at the level of eye pain that is the most painful (question 4), level of pain that is the least painful (question 5) and level of eye pain in average (question 6) at day 2 all 3 answers favored compound I compared to Vehicle (FIG. 5A-5C).

In the questions of how often eye pain was associated by the following symptoms: redness (question 22), burning (question 23), sensitivity to light (question 24) and tearing (question 25), all answers favored compound I compared to Vehicle (FIG. 6A-6D).

The VAS scores from time points 6.5, 18.5 and 24.5 hours post-operatively compared one-half hour prior to that and immediately before instillation of eye drops (namely at hours 6, 18 and 24) were −3.1, 2.8 and 1.3, respectively for compound I-treated eyes. For Vehicle-treated eyes the same differences were −5.6, 2.2 and −0.2, respectively.

Pharmacokinetics

Pharmacokinetic Assessments

Pharmacokinetic (PK) samples were collected at the time points defined in the visit schedule supra, with PK blood collection windows shown in Table 27.

TABLE 27

Permitted time window for PK blood collection

| Pre-dose | Post-dose |
|---|---|
| Within 90 min prior to dosing (sample numbers 101. 106, 107, 112, 117 and 118) | Within ±5 min of expected time point relative to dose, up to 2 hours post-dose |
| | Within ±5 min from 72.25 to 74 hours (0.25 to 2 hours relative to timing of last dose) |

All blood samples (3 mL) were taken from the arm by either direct venipuncture or an indwelling catheter inserted in a forearm vein. After each tube of blood was drawn, it was immediately inverted gently 8-10 times to ensure the mixing of tube contents with anticoagulant (3 mL K2 EDTA). Prolonged sample contact with the rubber stopper was avoided and the tubes were placed upright in a test tube rack surrounded by wet ice until centrifugation.

Within 30 minutes, the sample was centrifuged at about 5° C. for 10 minutes at approximately 2000 G (or the sample was placed on ice and centrifuged at room temperature). Immediately after centrifugation, the whole supernatant (approx. 1.5 mL) was transferred in the first 1.8 mL NUNC 2D barcoded cryovial. After mixing the plasma thoroughly, half of the plasma was transferred from the first cryovial to the second cryovial and the caps were secured. Appropriate PK cryolabels were attached to each cryovial and the labels were secured with clear tape. The cryovials were frozen immediately over dry ice then, kept frozen at ≤—20° C. until shipment to the central lab. The vials were shipped in biweekly batches.

Compound I was quantified in plasma using a validated LC-MS/MS method; the lower limit of quantification (LLOQ) was 0.05 ng/mL. Concentrations were expressed in ng per mL units. When feasible, bandage contact lenses (BCL) exposed to study drug were collected and analyzed for residual drug exposure after treatment (LLOQ: 5.00 ng/mL in 0.55 mL of extraction fluid, or 2.75 ng/BCL). Concentrations below the LLOQ were reported as "zero" and missing data were labeled as such.

The following PK parameters were determined as relevant using the actual recorded sampling times and non-compartmental method with Phoenix™ WinNonlin® (Version 6.4): Cmax, Tmax, AUClast (calculated), Clast and Tlast from the plasma concentration-time data. Pre-dose concentrations were determined by inspection at nominal 0, 24 and 72 hours. The linear trapezoidal rule was used for AUClast calculation. No PK parameters were calculated from the bandage contact lenses compound I concentration data.

Plasma Pharmacokinetics of Compound I

Figure 7A:
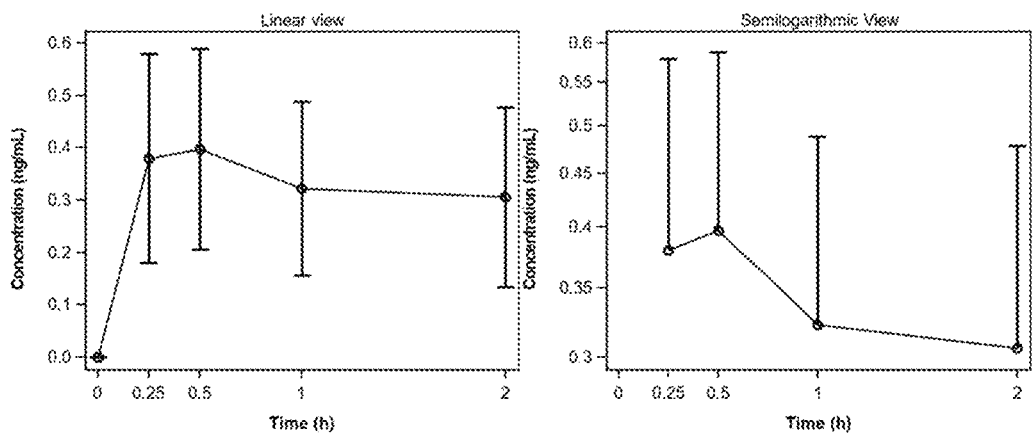
FIG. 7A provides the arithmetic mean (SD) plasma concentrations of compound I following topical ocular administration of 2.5% compound I (PK analysis set) on Day 1.
Figure 7B:
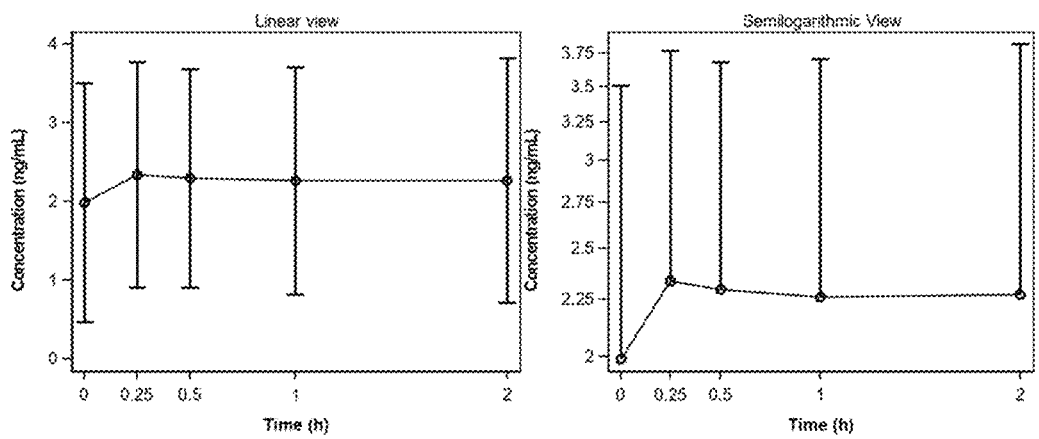
FIG. 7B provides the arithmetic mean (SD) plasma concentrations of compound I following topical ocular administration of 2.5% compound I (PK analysis set) on Day 4.

Arithmetic mean plasma concentration-time profiles and PK parameters of compound I are presented in FIG. 7A and FIG. 7B and Table 28.

After the unilateral topical ocular dose of compound I, absorption into the systemic circulation was rapid, with median Tmax of 0.459 hr and 0.467 hr after the first (Day 1; range 0.167-2.00 hr, FIG. 7A) and 13th (Day 4; range 0.00-2.08, FIG. 7B) doses, respectively. Cmax was determined and AUClast calculated for 34/40 patients on Day 1 and 33/40 (Cmax) or 31/40 (AUClast) patients on Day 4. All Day 1 pre-dose concentrations were below the limit of quantitation and imputed as 0.00 ng/mL. Trough (end of 6-hour dose interval and prior to next dose) mean concentration (CV %) prior to the 5th dose on Day 2 (24 hr post 1st dose; Day 2 time point of 0 h) was 1.25 ng/mL (54.9%), and slightly higher at 1.99 ng/mL (76.3%) prior to the 13th dose on Day 4 (72 hr post 1st dose; Day 4 time point of 0 h).

Concentrations were generally low, with observed Cmax ranging from 0.195 to 7.56 ng/mL, and AUClast from 0.261 to 14.5 ng*hr/mL, across 4 days of repeated QID dosing. Arithmetic mean Cmax (CV %) following the first dose on Day 1 was 0.454 ng/mL (49.9%) and 2.40 ng/mL (63.5%), i.e. 5.3-fold higher, after the 13th dose on Day 4. Corresponding mean AUClast (CV %) values were 0.638 ng*hr/mL (46.0%) and 4.38 ng*hr/mL (67.0%), representing a 6.9-fold increase over the 4 days.

TABLE 28

Summary statistics of compound I PK parameters after topical ocular administration of 2.5% compound I (PK analysis set)

| Profile day | Statistic | Cmax (ng/mL) | Tmax (hr) | AUClast (ng*hr/mL)[1] |
|---|---|---|---|---|
| 1 | N | 34 | 34 | 34 |
|   | Mean (SD) | 0.454 (0.227) | — | 0.638 (0.293) |

TABLE 28-continued

Summary statistics of compound I PK parameters after topical ocular administration of 2.5% compound I (PK analysis set)

| Profile day | Statistic | Cmax (ng/mL) | Tmax (hr) | AUClast (ng*hr/mL)[1] |
|---|---|---|---|---|
|   | CV % | 49.9 | — | 46.0 |
|   | Median | 0.375 | 0.459 | 0.569 |
|   | Min, Max | 0.195, 1.05 | 0.167, 2.00 | 0.261, 1.58 |
| 4 | N | 33 | 33 | 31 |
|   | Mean (SD) | 2.40 (1.53) | — | 4.38 (2.94) |
|   | CV % | 63.5 | — | 67.0 |
|   | Median | 2.07 | 0.467 | 3.42 |
|   | Min, Max | 0.639, 7.56 | 0.00, 2.08 | 1.18, 14.5 |

[1]Median Tlast (range): Day 1, 2.00 hr (1.95-2.05 hr); Day 4, 2.00 hr (1.77-2.10 hr) Clast is not shown.

Bandage Contact Lens

Bandage Contact Lens (BCL) was collected from 40 patients on Day 4 of the dose administration and analyzed for compound I. Values from the three IMP non-compliant patients were excluded from BCL summary statistics, leaving 37 values evaluable, including one value from a patient without available plasma PK. The mean concentration of compound I (CV %) in 0.55 mL extraction fluid was 8500 ng/mL (73.1%), with a wide range of 284 to 22600 ng/mL. These concentrations translate to an estimated mean of 4680 ng/lens (0.55 mL×8500 ng/mL), and a range of 156 to 12400 ng/lens. The amount in BCL was very small in relation to the 0.925 mg dose of compound I administered: mean 0.51%, and range of 0.017% to 1.3% of dose. This indicates that the BCL absorbs and retains topical ocular compound I, but at negligible amounts compared to the topical ocular dose.

Summary Pharmacokinetic Results

Absorption of compound I into the systemic circulation was rapid (median plasma Tmax was approximately 0.5 hours) after either single (first dose) or repeated 4 times daily topical ocular administration.

After both single and multiple topical ocular dose administration of compound I, the systemic exposure was low, ranging from 0.195 ng/mL to 7.56 ng/mL across 4 days of repeated QID dosing, and showed moderate variability. Mean Cmax was 0.454 ng/mL after the first dose on Day 1 and 2.40 ng/mL after the 13$^{th}$ dose on Day 4.

The CV % values for Cmax and AUClast following single dose were 49.9% and 46.0%, respectively. The corresponding values after repeated administration were 63.5% and 67.0%.

Mean Cmax after repeated administration (2.40 ng/mL) was 5.3-fold higher than after single dose on Day 1 (0.454 ng/mL). Similarly, mean AUC last was 6.9-fold higher after repeated versus single administration (4.38 versus 0.638 ng*hr/mL). These data indicated accumulation over the 4 day period of 2.5% compound I administration 4 times daily.

Bandage Contact Lens (BCL) was collected from 40 patients on Day 4 of dose administration. The mean concentration (CV %) in 0.55 mL extraction fluid was 8500 ng/mL (73.1%), which converts to an estimated 4680 ng/lens. The amount in BCL was very small in relation to the 0.925 mg dose of compound I administered: 0.51%, and range of 0.017% to 1.3% of dose. This indicates that the BCL absorbs and retains topical ocular compound I, but at negligible amounts compared to the topical ocular dose.

Safety

Safety assessments consisted of collecting all AEs, SAEs, with their severity and relationship to study drug. Table 29 includes a list of signs and symptoms which are common in the post-PRK surgery setting. Only signs and symptoms greater than the listed ranges of either severity or duration were reported as AEs.

TABLE 29

Signs and symptoms of PRK surgery which do not require reporting

| Sign/symptom | Expected severity | Expected duration after PRK surgery |
| --- | --- | --- |
| Corneal epithelial defect | Mild to moderate | 1 week |
| Eye Edema | Mild to moderate | 1 week |
| Eyelid Edema | Mild to moderate | 1 week |
| Punctate Keratitis | Mild to moderate | 1 week |
| Conjunctival Hyperemia | Mild to moderate | 1 week |
| Reduction in BCVA of 10 letters or more from baseline | Mild to moderate | 1 month |
| Eye pain | Mild to moderate | 1 week |
| Ocular irritation/discomfort | Mild to moderate | 1 month |
| Foreign body sensation | Mild to moderate | 1 month |
| Lid margin irritation/crusting | Mild to moderate | 1 month |
| Increased Lacrimation | Mild to moderate | 1 month |
| Vision that is shadowy | Mild to moderate | 1 month |
| Vision that is hazy | Mild to moderate | 1 month |
| Blurred vision | Mild to moderate | 1 month |
| Photophobia | Mild to moderate | 1 month |
| Dry eye | Mild to moderate | 1 month |
| Glare | Mild to moderate | 1 month |
| Halos | Mild to moderate | 1 month |

One week indicates resolution by the Day 8 post-op visit (Visit 6 in treatment period 1 or Visit 11 in period 2), including the allowable window. The table was constructed before initiating the study and with feedback from all primary investigators and surgeons based on their compiled experience with commonly encountered and expected clinical manifestations after standard PRK surgery.

One month indicates resolution by the EOS visit, or within 37 days post-surgery in cases where an EOS visit is not performed or there is more than one week between study surgeries.

Adverse events and serious adverse events included an assessment of both systemic and ocular assessments. Systemic safety assessments included regular assessments of height and weight, vital signs, reporting medication errors including misuse/abuse, pregnancy reporting and early phase safety monitoring. The misuse/abuse, pregnancy reporting and early phase safety monitoring were not assessed for the study. Ocular safety assessments included the following:

Best-corrected visual acuity (BCVA) and uncorrected visual acuity (UCVA): Was measured at each visit using an ETDRS visual acuity chart at 4 meters (13 feet) or 1 meter (for patients that cannot read the 4 meter chart). The BCVA scoring was done based on the number of correctly read letters plus 30. If visual acuity was so poor that the patient could not read any of the largest letters at 1 meter, count fingers and hand movement vision and light perception was tested.

Intraocular Pressure (IOP): IOP measurements were conducted with applanation tonometry or Tonopen.

Dilated fundus exam: The dilated fundus examination included ophthalmoscopic assessments of the vitreous, retina/macula/choroid, and optic nerve. Evaluations for retinal tear/detachment, retinal hemorrhage, vitreous hemorrhage density, vitreous haze grading and abnormal findings were done and scored according to grading criteria.

Ocular hyperemia: Conjunctival redness of the bulbar conjunctiva in each eye at the slit lamp according to the McMonnies redness scale was graded. Hyperemia was assessed in four regions (superior, inferior, temporal, nasal) of each eye with severity scored 0-5 in each region.

Size of epithelial defect by slit lamp exam: Using an oblique viewing angle relative to the source beam and a narrow slit beam, the cornea was sectioned to visualize the vertical and horizontal borders of the corneal wound. By adjusting the calibrated slit beam width and height, the maximum horizontal (wound width) and vertical dimensions (wound height) of the surgical epithelial wound was estimated. The evaluation was performed until wound closure and report of wound size as 0 horizontal and 0 vertical dimensions.

Slit-lamp biomicroscopy: Ocular signs (eyelids/conjunctiva, cornea, lens, and iris/anterior chamber) was assessed in both eyes by slit lamp biomicroscopy according to the grading criteria.

Blink rate: A blink was defined as a bilateral paroxysmal closure of the eyelids (duration<1 second) in the absence of a provoking external stimulus. Each blink assessment lasted for 2 min (or as close to 2 minutes as possible with minimum time 1 minute) and the obtained blink rate was averaged to calculate blink rate in blinks/min.

Tear production (Schirmer's test without anesthesia): The test was performed without anesthetic in both eyes simultaneously. Tear secretion was measured in millimeters of the length of strip wetted by tears. The measurement was made to the nearest whole number.

Corneal staining: This test was performed by gently touching the wet end of an impregnated sodium fluorescein strip to the inferior conjunctival sac. The strip was wetted with 1 drop of sterile saline and flicked to remove excess saline. The patient blinked several times to ensure dispersion of the dye throughout the tear film prior to grading on a scale of 0-3 (0=Normal, No staining; 1=Mild, Superficial stippling micropunctate staining; 2=Moderate, Macropunctate staining with some coalescent areas and 3=Severe, Numerous coalescent macropunctate areas and/or patches) for each of 5 zones (central plus 4 quadrants).

Safety Evaluation

There were no deaths or SAEs or discontinuation of the drug or discontinuation from the study due to AEs in the study. A total of 18 AEs were reported in 10 patients (25% of the 40 enrolled patients) of which twelve occurred after treatment with compound I, five after treatment with Vehicle and one occurred in one patient prior to dosing of the study drug. All AEs were either mild or moderate in severity.

A total of 10 patients (25%) experienced at least one treatment emergent AE, five patients experienced a single AE, and five patients experienced more than one AE. Five patients experienced an AE only during treatment with compound I, two patients experienced an AE only during treatment with Vehicle and three patients experienced an AE during treatment with both compound I and Vehicle. There was one AE (headache) that occurred prior to dosing of first study drug.

There were six ocular AEs in four patients (10% of the 40 enrolled patients), all of which were of mild severity (three eyes each treated with compound I and Vehicle). None of the AEs were suspected to be related to either study drug (compound I or Vehicle). Five of the six ocular AEs were thought to be related to the PRK procedure (two belonged to compound I treated eyes and 3 Vehicle treated eyes) by the Investigator.

There were twelve non-ocular AEs in seven patients (17.5%) (six eyes treated with compound I, two eyes treated with Vehicle and one patient during no drug period). Five AEs in four patients (10%) were of moderate severity (four eyes treated with compound I and one eye treated with Vehicle). The remaining AEs were of mild severity. None of the AEs were suspected to be related to compound I by the investigator.

Table 30 provides the overall incidence of adverse events.

TABLE 30

Overall incidence of AEs - number of events and number of patients (Safety analysis set)

| | Compound I 2.5%<br>N = 40<br>n (%) | Vehicle<br>N = 40<br>n (%) | No drug*<br>N = 40<br>n (%) | Total<br>N = 40<br>n (%) |
|---|---|---|---|---|
| Patients with at least one AE | 8 (20) | 5 (12.5) | 1 (2.5) | 10 (25) |
| Number of AEs | 12 | 5 | 1 | 18 |
| Patients with at least one ocular AE | 3 (7.5) | 3 (7.5) | 0 | 4 (10) |
| Number of ocular AEs | 3 | 3 | 0 | 6 |
| Patients with at least one non-ocular AE | 6 (15) | 2 (5) | 1 (2.5) | 7 (17.5) |
| Number of non-ocular AEs | 9 | 2 | 1 | 12 |
| Number of mild severity AEs | 8 | 4 | 1 | 13 |
| Number of moderate severity AEs | 4 | 1 | 0 | 5 |
| Number of severe AEs | 0 | 0 | 0 | 0 |
| Number of procedure-related AEs | 2 | 3 | 0 | 5 |
| Number of drug-related AEs | 0 | 0 | 0 | 0 |

An AE starting in one period and continuing into the next was counted only in the onset period.
N = number of patients studied.
*No drug, or baseline-emergent AE: AEs encountered after singing the informed consent and before the administration of any study drug (compound I or Vehicle).

Ocular Safety Assessments

Best-corrected visual acuity (BCVA) and uncorrected visual acuity (UCVA): The administration of compound I did not result in any trend or obvious difference between compound I and Vehicle-treated eyes throughout the study. The data therefore indicate that compound I reduces pain without adversely affecting BCVA and UCVA.

Intraocular pressure (1OP): No trend across the scheduled time points or obvious differences between compound I and Vehicle-treated eyes was observed throughout the study. At the end of study, there was slight increase (<5 mmHg) in mean IOP values compared to Baseline. The small change in mean scores during the study was not clinically significant.

Dilated fundus exam: No abnormal findings were reported by the Investigator across the scheduled time points for compound I and Vehicle-treated eyes.

Figure 8A:
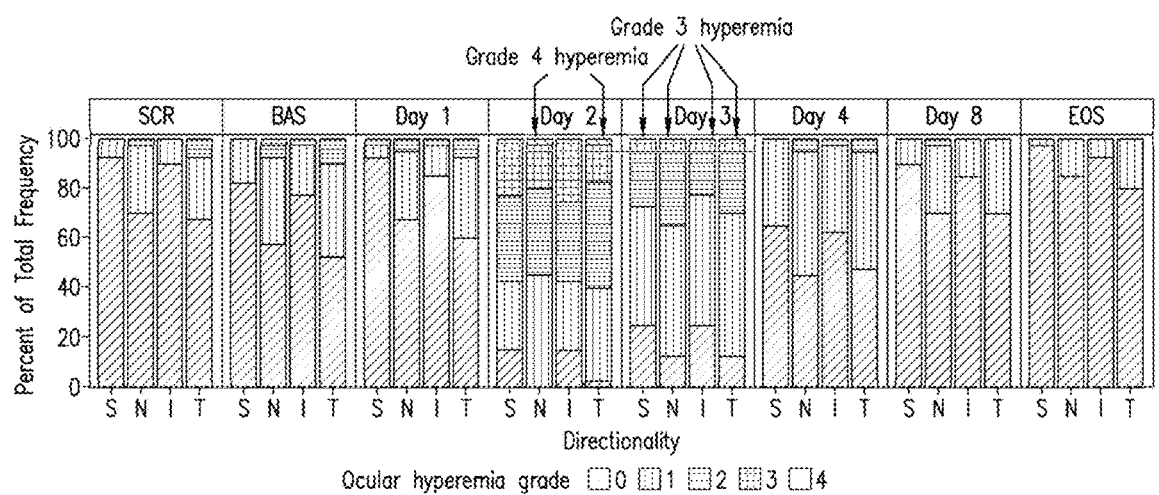
FIG. 8A provides a bar chart of ocular hyperemia over time for compound I, FIG. 8B provides a bar chart of ocular hyperemia over time for Vehicle. The quadrants are S: Superior, N: Nasal, I: Inferior, and T: Temporal.
Figure 8B:
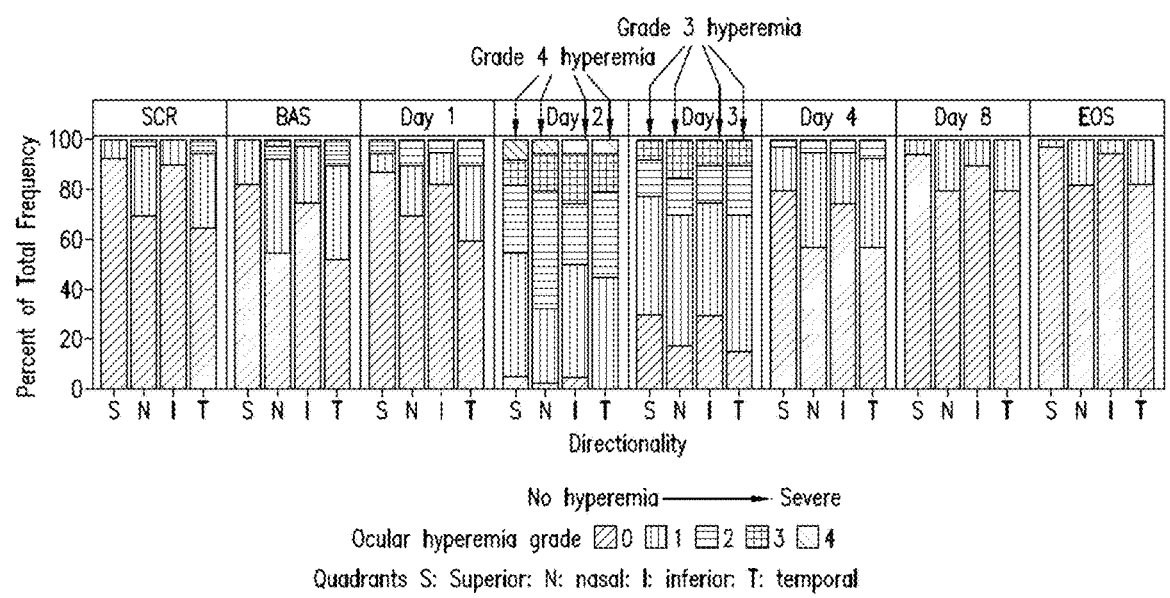

Ocular hyperemia: A bar chart of ocular hyperemia over time for compound I and placebo treated eyes is provided in FIG. 8A and FIG. 8B, respectively. FIGS. 8A and 8B indicate the Grade 4 and Grade 3 ocular hyperemia (as measured on the McMonnies scale) on Days 3 and 4, respectively. As seen in FIG. 8A, on Day 2 postoperatively (24 hours after PRK surgery) there was less grade 4 hyperemia (all quadrants) in compound I treated eyes compared to Vehicle treated eyes. In the superior quadrant the p-value for this difference was 0.04. On Day 3 (48 hours post-operative) less grade 3 hyperemia was observed in compound I treated eyes compared to Vehicle treated eyes. None of the observations were captured as AEs.

Size of epithelial defect by slit lamp exam: In order to assess the rate of wound healing after administration of compound I, the size of the epithelial defect in both compound I and Vehicle treated populations was measured. The elliptical area of epithelial wound size was calculated as follows: Area (mm2)=width×height×pi, from the width and height of the epithelial defect measured at the slit lamp. The difference in epithelial wound area between compound I and Vehicle was not noticeably different at any time point except at Day 2 post-PRK surgery (all p-values for the difference in area was >0.35). On Day 2 (24 hours post-operative), the difference in average epithelial defect area between patients treated with compound I vs. Vehicle was 11.23 mm$^2$ (p value=0.034). This difference was not clinically significant in the immediate post-operative period. By Day 3 (48 hours post-operative) there was no difference between the compound I-treated and the Vehicle-treated eyes and the area of the wound was very small. On Day 4 (48 hours post-operative) almost all eyes had healed and there was no difference between compound I-treated and Vehicle treated eyes. Compound I showed no delay in wound healing compared to Vehicle.

Figure 9:
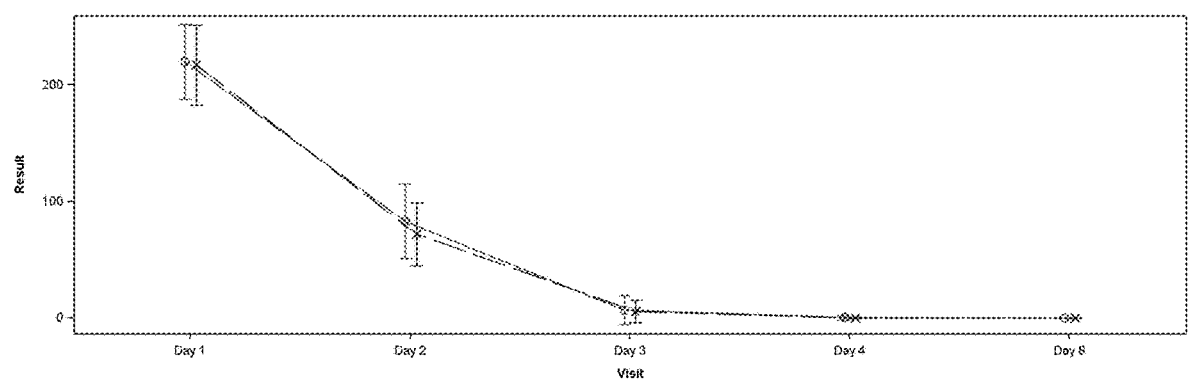
FIG. 9 provides the arithmetic mean (+/− SD) of epithelial defect size over time (Safety analysis set) Parameter (unit): Epithelial Wound Size (mm), Subcategory: Area (mm2). The dashed line with "x" represents vehicle, and the solid line with circles (o) represents compound I.

FIG. 9 and Table 31 provide a comparison of the epithelial size defect of compound I treated eyes versus Vehicle treated eyes.

TABLE 31

Statistical analysis of epithelial defect size (Safety analysis set)
Parameter (unit): Epithelial Wound Size (mm)
Subcategory: Area (mm$^2$)

| | Raw mean (SD) | | | |
|---|---|---|---|---|
| Visit | compound I | Vehicle | Difference compound I − Vehicle | p-value* |
| Day 1 | 220.15 (32.26) | 217.16 (34.72) | 2.98 (27.33) | 0.494 |
| Day 2 | 83.02 (32.08) | 71.79 (26.96) | 11.23 (32.30) | 0.034 |
| Day 3 | 6.75 (12.66) | 5.73 (9.73) | 1.02 (8.78) | 0.467 |
| Day 4 | 0.39 (2.04) | 0.08 (0.50) | 0.31 (2.11) | 0.352 |
| Day 8 | 0.00 (0.00) | 0.00 (0.00) | 0.00 (0.00) | |

*Obtained from a paired t-test
Epithelial defect size was calculated by slit lamp exam as the area of an ellipse calculated by maximum horizontal and vertical distance from center of epithelial defect.
Area (mm$^2$) = width*height*pi Slit-lamp biomicroscopy: The slit-lamp biomicroscopic examination consisted of examination of ocular structures (eyelids/conjunctiva, cornea, iris/anterior chamber, lens, aqueous flare and aqueous inflammatory cell grade). No abnormalities were observed in ocular structures of aqueous flare and aqueous inflammatory cell grade, iris/anterior chamber and lens in patients treated with both compound I and Vehicle across the scheduled time points.

Blink rate: There were fluctuations in the mean blink rate; however, no trend across the scheduled time points or obvious differences between blink rate after compound I and Vehicle treatment was observed throughout the study. At the end of study, no clinically relevant changes were observed in blink rate compared to Baseline.

Corneal staining: Most of the patients had normal (grade 0) degree of staining measured on Baseline, Day 8 and EOS visits. No clinical differences were observed in the corneal staining between the eyes treated with compound I versus Vehicle, at either the baseline, or the Day 8 or the EOS visit.

Vital signs, physical findings and other observations related to safety: The vital sign parameters (systolic and diastolic blood pressures, pulse rate and body temperature) were within the normal range for all patients during the study. No AEs related to vital signs were observed. Electrocardiogram and special safety topics were not conducted and assessed (as per protocol).

Summary of Safety Results
- There were no deaths, or serious or severe AEs, treatment discontinuations or study discontinuations reported in this study.
- No AEs were evaluated to be related to study drug (either compound I or Vehicle). Eight of 40 patients and five of 40 patients developed AEs after compound I and Vehicle treatment, respectively. All Ocular AEs were mild and balanced between compound I and Vehicle with the vast majority being well known AEs related to the PRK procedure.
- There were no observed clinically meaningful differences in safety between compound I and Vehicle.
- Compound I showed no delay in wound healing compared to Vehicle.
- Fewer compound I-treated eyes showed severe conjunctival hyperemia on Day 2 (24 hours post-operative) compared to Vehicle-treated eyes.
- There were no clinically relevant changes observed for BCVA, IOP, slit-lamp biomicroscopy, dilated eye exam, blink rate, tear production, corneal staining, or vital signs after compound I administration compared to Vehicle.

The incidence of AEs by preferred term is presented in Table 32.

ods, and/or steps described in the specification. Various modifications, substitutions, and variations can be made to the disclosed material without departing from the spirit and/or essential characteristics of the present invention. Accordingly, one of ordinary skill in the art will readily appreciate from the invention that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

What is claimed is:

1. A formulation, comprising:
a suspension of 4-(7-Hydroxy-2-isopropyl-4-oxo-4H-quinazolin-3-yl)-benzonitrile (compound I) or a salt, co-crystal, or polymorph thereof, in an amount of about 0.5% w/v to about 3.5% w/v,
tyloxapol in an amount of about 0.04% w/v to about 0.06% w/v;
carbomer homopolymer Type B in an amount from about 0.05% w/v to about 0.4% w/v;
a tonicity agent;
a buffer;

TABLE 32

Incidence of AEs by preferred term - n (percent) of patients (Safety analysis set)

| | | Compound I 2.5% N = 40 n (%) | | | Vehicle N = 40 n (%) | | | No drug (prior to drug)* N = 40 n (%) | | | Total N = 40 |
|---|---|---|---|---|---|---|---|---|---|---|---|
| AEs by preferred term | | n (%) | Severity | Procedure related | n (%) | Severity | Procedure related | n (%) | Severity | Procedure related | n (%) |
| Patients with at least one AE | | 8 (20.0) | | | 5 (12.5) | | | 1 (2.5) | | | 10 (25) |
| Ocular AEs | Corneal Infiltrate | 0 | | | 1 (2.5) | mild | yes | 0 | | | 1 (2.5) |
| | Corneal Opacity | 1 (2.5) | mild | yes | 1 (2.5) | mild | yes | 0 | | | 1 (2.5) |
| | Punctate Keratitis | 1 (2.5) | mild | yes | 1 (2.5) | mild | yes | 0 | | | 1 (2.5) |
| | Posterior Vitreous Detachment | 1 (2.5) | mild | no | 0 | | | 0 | | | 1 (2.5) |
| Non-ocular AEs | Headache | 1 (2.5) | mild | no | 1 (2.5) | moderate | no | 1 (2.5) | mild | no | 3 (7.5) |
| | Arthralgia | 1 (2.5) | mild | no | 0 | | | 0 | | | 1 (2.5) |
| | Nasopharyngitis | 2 (5.0) | mild, mild | no | 0 | | | 0 | | | 2 (5.0) |
| | Oropharyngeal Pain | 1 (2.5) | mild | no | 0 | | | 0 | | | 1 (2.5) |
| | Tinnitus | 0 | | | 1 (2.5) | mild | no | 0 | | | 1 (2.5) |
| | Sinus Congestion | 1 (2.5) | moderate | no | 0 | | | 0 | | | 1 (2.5) |
| | Sinusitis | 1 (2.5) | moderate | no | 0 | | | 0 | | | 1 (2.5) |
| | Pyrexia | 1 (2.5) | moderate | no | 0 | | | 0 | | | 1 (2.5) |
| | Vomiting | 1 (2.5) | moderate | no | 0 | | | 0 | | | 1 (2.5) |

An adverse event starting in one period and continuing into the next is counted only in the onset period.
N = number of patients studied.
n = number of patients with at least one AE in the category.
*No drug, or baseline-emergent AE: AEs encountered after singing the informed consent and before the administration of any study drug (compound I or Vehicle).

All publications and patent documents cited herein are incorporated herein by reference as if each such publication or document was specifically and individually indicated to be incorporated herein by reference. The present invention and its embodiments have been described in detail. However, the scope of the present invention is not intended to be limited to the particular embodiments of any process, manufacture, composition of matter, compounds, means, methods, and/or steps described in the specification.

sodium chloride in an amount of from 0.01% w/v to about 1% w/v;
optionally, a preservative; and
water in quantity sufficient (qs) to 100%.

2. The formulation according to claim 1, wherein the tonicity agent is a polyol selected from the group selected from mannitol, glycerin, xylitol, sorbitol, propylene glycol, and combinations thereof.

3. The formulation according to claim 1, wherein the buffer is selected from the group consisting of acetate, ascorbate, borate, hydrogen carbonate, carbonate, citrate, edetate (EDTA) gluconate, lactate, phosphate, propionate and TRIS (tromethamine).

4. The formulation according to claim 1, wherein the pH of the formulation is about 5.0 to about 8.0, about 5.5 to about 8.0, about 5.5 to about 7.5, about 5.0 to about 7.4, about 5.5 to about 7.4, about 6.0 to about 8.0, about 6.5 to about 8.0, about 6.0 to about 7.4, or about 6.5 to about 7.4.

5. The formulation according to claim 1, further comprising an additional agent selected from the group consisting of polyvinylprrolidone, hydroxypropylβcyclodextrin, and sulfoalkylether β-cyclodextrin in an amount of at least about 1.5 w/v %, at least about 3.0 w/v %, at least about 3.5 w/v % or at least about 4.5 w/v, but no greater than about 10.0 w/v %, no greater than about 8.0% w/v, no greater than about 6.5 w/v %, or no greater than about 5.5 w/v.

6. The formulation according to claim 1, further comprising an additional agent selected from the group consisting of cyclodextrins in an amount of at least about 1.5 w/v %, at least about 3.0 w/v %, at least about 3.5 w/v % or at least about 4.5 w/v, but no greater than about 10.0 w/v %, no greater than about 8.0% w/v, no greater than about 6.5 w/v %, or no greater than about 5.5 w/v.

7. A formulation according to claim 1, wherein compound I is in polymorphic form B.

8. The formulation according to claim 7, wherein the polymorphic form B is characterized by an X-ray diffraction pattern having three or more peaks at 2θ values selected from 9.3, 10.6 and 14.4.+−.0.2° 2θ.

9. The formulations according to claim 1, having a osmolality of about 200 to about 450 milliosmoles per kilogram (mOsm/kg).

10. The formulation according to claim 1, wherein the formulation comprises no more than about 10% of a degradation product after 6 months under refrigeration, wherein the degradation product has a relative retention time of 1.23, compared to compound I, when analyzed by HPMC using a gradient 0.1% trifluoroacetic acid (TFA) water/acetonitrile mobile phase.

11. A method of making a formulation, comprising mixing an amount of 4-(7-Hydroxy-2-isopropyl-4-oxo-4H-quinazolin-3-yl)-benzonitrile
(compound I) or a salt, co-crystal, or polymorph thereof,
a non-ionic surfactant;
a suspending agent;
a tonicity agent;
a buffer;
optionally, a salt;
optionally, a preservative; and
water qs to 100%, and
adjusting the pH to a range of from about 5.0 to about 8.0.

* * * * *

UNITED STATES PATENT AND TRADEMARK OFFICE
CERTIFICATE OF CORRECTION

| | |
|---|---|
| PATENT NO. | : 11,478,480 B2 |
| APPLICATION NO. | : 16/789976 |
| DATED | : October 25, 2022 |
| INVENTOR(S) | : Bullock et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 149 days.

Signed and Sealed this
Twelfth Day of August, 2025

Coke Morgan Stewart
*Acting Director of the United States Patent and Trademark Office*